United States Patent
Verkhusha et al.

(10) Patent No.: US 12,134,634 B2
(45) Date of Patent: Nov. 5, 2024

(54) SMALL NEAR-INFRARED FLUORESCENT PROTEINS DEVELOPED FROM CYANOBACTERIOCHROME

(71) Applicants: Vladislav V. Verkhusha, Bronx, NY (US); Olena S. Oliinyk, Helsinki (FI)

(72) Inventors: Vladislav V. Verkhusha, Bronx, NY (US); Olena S. Oliinyk, Helsinki (FI)

(*) Notice: Subject to any disclaimer, the term of this patent is extended or adjusted under 35 U.S.C. 154(b) by 551 days.

(21) Appl. No.: 17/115,223

(22) Filed: Dec. 8, 2020

(65) Prior Publication Data

US 2021/0179675 A1 Jun. 17, 2021

Related U.S. Application Data

(60) Provisional application No. 62/947,155, filed on Dec. 12, 2019.

(51) Int. Cl.
| | | |
|---|---|---|
| *C07K 14/405* | (2006.01) | |
| *A61K 49/00* | (2006.01) | |
| *C12Q 1/6816* | (2018.01) | |

(52) U.S. Cl.
CPC ........ *C07K 14/405* (2013.01); *A61K 49/0045* (2013.01); *C12Q 1/6816* (2013.01)

(58) Field of Classification Search
None
See application file for complete search history.

(56) References Cited

U.S. PATENT DOCUMENTS

| | | | |
|---|---|---|---|
| 2021/0121582 A1* | 4/2021 | Krishnamani | ... C07K 14/43595 |
| 2022/0155309 A1* | 5/2022 | Terada | ...... C07K 1/13 |

FOREIGN PATENT DOCUMENTS

| | | | | |
|---|---|---|---|---|
| CN | 111269941 A | * | 6/2020 | ............ C12N 15/65 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Rockwell et al., "NpR3784 is the prototype for a distinctive group of red/green cyanobacteriochromes using alternative Phe residues for photoproduct tuning", Photochem. Photobiol. Sci. 14:258-269, 2015 (Year: 2015).*
UniProt Database Accession No. B2J457, Dec. 2018, 3 pages (Year: 2018).*
Oliinyk et al., Supplementary Information for "Smallest near-infrared fluorescent protein evolved from cyanobacteriochrome as versatile tag for spectral multiplexing", Jan. 2019, 18 pages (Year: 2019).*
Translation of CN111269941A, 20 pages, obtained from Google Patents on Jun. 12, 2023 (Year: 2023).*
Oliinyk et al., "Smallest near-infrared fluorescent protein evolved from cyanobacteriochrome as versatile tag for spectral multiplexing", Nat. Comm. 10:279, Jan. 2019, 13 pages (Year: 2019).*
Oliinyk et al., "Smallest near-infrared fluorescent protein evolved from cyanobacteriochrome as versatile tag for spectral multiplexing", GenBank Database Accession No. MK176509, Feb. 2019, 1 page (Year: 2019).*

* cited by examiner

*Primary Examiner* — David Steadman
(74) *Attorney, Agent, or Firm* — Amster, Rothstein & Ebenstein LLP

(57) ABSTRACT

This invention provides the nucleic acid molecules encoding novel small monomeric near-infrared fluorescent protein miRFP670nano, variants and derivatives thereof as well as proteins and peptides encoded by these nucleic acids. The invention also relates to derivatives, homologues, or mutants of the specific proteins referenced above as well as fragments of the nucleic acids and the peptides encoded thereby. The invention further relates to host-cells, stable cell lines and transgenic organisms comprising above-referenced nucleic acid molecules. The present invention also refers to methods of making and using small monomeric near-infrared fluorescent proteins derived from cyanobacteriochromes. The presented protein and its derivatives find use in a variety of applications and approaches, including labeling of biomolecules, cells or cell organelles, detecting protein-protein interactions, and generation of genetically encoded fluorescent biosensors.

4 Claims, 22 Drawing Sheets
(19 of 22 Drawing Sheet(s) Filed in Color)

Specification includes a Sequence Listing.

```
miRFP670nano   (1) MANLDKMLNTTVTEVRQFLQVDRVCVFQFEEDYSGVVVVEAVDDRWISILKTQVRDRYFMETRGEEYSHGRYQA
miRFP670nano3  (1) MANLDKMLNTTVTEVRKFLQADRVCVFKFEEDYSGTVSHEAVDDRWISILKTQVQDRYFMETRGEEYVHGRYQA
miRFP704nano   (1) MANLDKMLNTIVTEVRQFLQVDRVCVFQFEEDYSGRVVVEAVDDRWNSILKTQVRDCYFMETRGEEYLHGRYQA
miRFP718nano   (1) MANLDKMLNTIVTEVRQFLQVDRLCVFKFEEDYSGNIIYEAVDDQWLSILKTRVRDCYFMETRGEEYLHGRYQA
NpR3784 (GAF)  (1) --NLDKVLNTTVTEVRQFLQVDRVFMYQFEPDYSGVVVVESVDDRWIAILNTQVQDTYFMETRGEEYSHGRIQA miRFP670nano  (75) IADIYTANLTECYRDLLTQFQVRAILAVPILQGKKLWGLLVAHQLAAPRQWQTWEIDFLKQAVYVGIAIQQS
miRFP670nano3 (75) IADIYTANLVECYRDLLIEFQVRAILAVPILQGKKLWGLLVAHQLAGPREWQTWEIDFLKQQAVVMGIAIQQS
miRFP704nano  (75) IADIYQANLLESYRDLLGQFQVRAILAVPIIKGKKLWGLLVAHQLAAPRSWQTWEIEFLKQQAVVMGIAIQQS
miRFP718nano  (75) IADIHQANLAESYRDFLTQYQVRAIVAVPILKGKKLWGLFSAHQLAAPRSWQAWEIEFLKQQAVVMGIAIQQS
NpR3784 (GAF) (75) IADIYTAGLTECHRDLLTQFQVRANLAVPILQGKKLWGLLVANQCAAPRQWQTWEIDFLKQLAVQVGIAIQQS
```

Fig. 10.

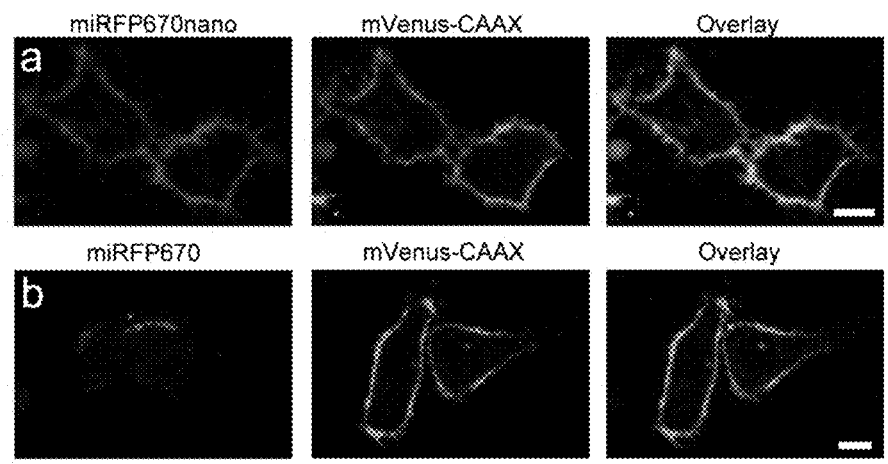
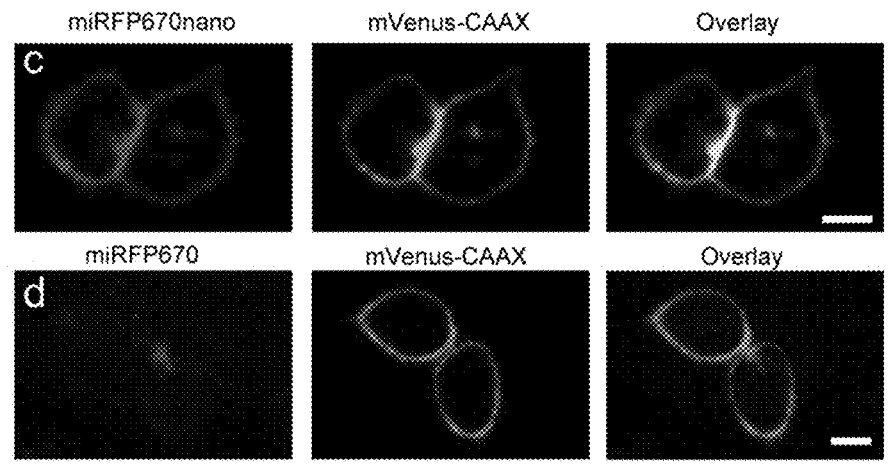
Fig. 14(a)-14(d).

SEQUENCE LISTING

```
<160> NUMBER OF SEQ ID NOS: 28

<210> SEQ ID NO 1
<211> LENGTH: 147
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 1

Met Ala Asn Leu Asp Lys Met Leu Asn Thr Thr Val Thr Glu Val Arg
1               5                   10                  15

Gln Phe Leu Gln Val Asp Arg Val Cys Val Phe Gln Phe Glu Glu Asp
            20                  25                  30

Tyr Ser Gly Val Val Val Val Glu Ala Val Asp Asp Arg Trp Ile Ser
        35                  40                  45

Ile Leu Lys Thr Gln Val Arg Asp Arg Tyr Phe Met Glu Thr Arg Gly
    50                  55                  60

Glu Glu Tyr Ser His Gly Arg Tyr Gln Ala Ile Ala Asp Ile Tyr Thr
65                  70                  75                  80

Ala Asn Leu Thr Glu Cys Tyr Arg Asp Leu Leu Thr Gln Phe Gln Val
                85                  90                  95

Arg Ala Ile Leu Ala Val Pro Ile Leu Gln Gly Lys Lys Leu Trp Gly
            100                 105                 110

Leu Leu Val Ala His Gln Leu Ala Ala Pro Arg Gln Trp Gln Thr Trp
        115                 120                 125

Glu Ile Asp Phe Leu Lys Gln Gln Ala Val Val Val Gly Ile Ala Ile
    130                 135                 140

Gln Gln Ser
145

<210> SEQ ID NO 2
<211> LENGTH: 147
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 2

Met Ala Asn Leu Asp Lys Met Leu Asn Thr Thr Val Thr Glu Val Arg
1               5                   10                  15

Lys Phe Leu Gln Ala Asp Arg Val Cys Val Phe Lys Phe Glu Glu Asp
```

```
            20                  25                  30
Tyr Ser Gly Thr Val Ser His Glu Ala Val Asp Asp Arg Trp Ile Ser
        35                  40                  45

Ile Leu Lys Thr Gln Val Gln Asp Arg Tyr Phe Met Glu Thr Arg Gly
    50                  55                  60

Glu Glu Tyr Val His Gly Arg Tyr Gln Ala Ile Ala Asp Ile Tyr Thr
65                  70                  75                  80

Ala Asn Leu Val Glu Cys Tyr Arg Asp Leu Leu Ile Glu Phe Gln Val
                85                  90                  95

Arg Ala Ile Leu Ala Val Pro Ile Leu Gln Gly Lys Lys Leu Trp Gly
            100                 105                 110

Leu Leu Val Ala His Gln Leu Ala Gly Pro Arg Glu Trp Gln Thr Trp
        115                 120                 125

Glu Ile Asp Phe Leu Lys Gln Gln Ala Val Val Met Gly Ile Ala Ile
    130                 135                 140

Gln Gln Ser
145

<210> SEQ ID NO 3
<211> LENGTH: 147
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 3

Met Ala Asn Leu Asp Lys Met Leu Asn Thr Ile Val Thr Glu Val Arg
1               5                   10                  15

Gln Phe Leu Gln Val Asp Arg Val Cys Val Phe Gln Phe Glu Glu Asp
            20                  25                  30

Tyr Ser Gly Ser Val Val Glu Ala Val Asp Asp Arg Trp Asn Ser
        35                  40                  45

Ile Leu Lys Thr Gln Val Arg Asp Cys Tyr Phe Met Glu Thr Arg Gly
    50                  55                  60

Glu Glu Tyr Leu His Gly Arg Tyr Gln Ala Ile Ala Asp Ile Tyr Gln
65                  70                  75                  80

Ala Asn Leu Leu Glu Ser Tyr Arg Asp Leu Leu Gly Gln Phe Gln Val
                85                  90                  95

Arg Ala Ile Leu Ala Val Pro Ile Ile Lys Gly Lys Lys Leu Trp Gly
            100                 105                 110

Leu Leu Val Ala His Gln Leu Ala Ala Pro Arg Ser Trp Gln Thr Trp
        115                 120                 125

Glu Ile Glu Phe Leu Lys Gln Gln Ala Val Val Met Gly Ile Ala Ile
    130                 135                 140

Gln Gln Ser
145

<210> SEQ ID NO 4
<211> LENGTH: 147
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 4

Met Ala Asn Leu Asp Lys Met Leu Asn Thr Ile Val Thr Glu Val Arg
1               5                   10                  15
```

```
Gln Phe Leu Gln Val Asp Arg Leu Cys Val Phe Lys Phe Glu Asp
            20                  25                  30

Tyr Ser Gly Asn Ile Ile Tyr Glu Ala Val Asp Asp Gly Trp Leu Ser
        35                  40                  45

Ile Leu Lys Thr His Val Arg Asp Cys Tyr Phe Met Glu Thr Arg Gly
50                  55                  60

Glu Glu Tyr Leu His Gly Arg Tyr Gln Ala Ile Ala Asp Ile His Gln
65                  70                  75                  80

Ala Asn Leu Ala Glu Ser Tyr Arg Asp Phe Leu Thr Gln Tyr Gln Val
                85                  90                  95

Arg Ala Ile Val Ala Val Pro Ile Leu Lys Gly Lys Lys Leu Trp Gly
            100                 105                 110

Leu Phe Ser Ala His Gln Leu Ala Ala Pro Arg Ser Trp Gln Ala Trp
        115                 120                 125

Glu Ile Glu Phe Leu Lys Gln Gln Ala Val Val Met Gly Ile Ala Ile
    130                 135                 140

Gln Gln Ser
145

<210> SEQ ID NO 5
<211> LENGTH: 156
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 5

Met Ala Ser Gly Lys Lys Leu Trp Gly Leu Leu Val Ala His Gln Leu
1               5                   10                  15

Ala Ala Pro Arg Gln Trp Gln Thr Trp Glu Ile Asp Phe Leu Lys Gln
            20                  25                  30

Gln Ala Val Val Val Gly Ile Ala Ile Gln Gln Ser Gly Gly Gly Gly
        35                  40                  45

Ser Ala Asn Leu Asp Lys Met Leu Asn Thr Thr Val Thr Glu Val Arg
50                  55                  60

Gln Phe Leu Gln Val Asp Arg Val Cys Val Phe Gln Phe Glu Glu Asp
65                  70                  75                  80

Tyr Ser Gly Val Val Val Glu Ala Val Asp Asp Arg Trp Ile Ser
                85                  90                  95

Ile Leu Lys Thr Gln Val Arg Asp Arg Tyr Phe Met Glu Thr Arg Gly
            100                 105                 110

Glu Glu Tyr Ser His Gly Arg Tyr Gln Ala Ile Ala Asp Ile Tyr Thr
        115                 120                 125

Ala Asn Leu Thr Glu Cys Tyr Arg Asp Leu Leu Thr Gln Phe Gln Val
    130                 135                 140

Arg Ala Ile Leu Ala Val Pro Ile Leu Gln Gly Ser
145                 150                 155

<210> SEQ ID NO 6
<211> LENGTH: 156
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 6

Met Ala Ser Gly Lys Lys Leu Trp Gly Leu Leu Val Ala His Gln Leu
1               5                   10                  15
```

```
Ala Gly Pro Arg Glu Trp Gln Thr Trp Glu Ile Asp Phe Leu Lys Gln
            20                  25                  30

Gln Ala Val Val Met Gly Ile Ala Ile Gln Gln Ser Gly Gly Gly Gly
        35                  40                  45

Ser Ala Asn Leu Asp Lys Met Leu Asn Thr Thr Val Thr Glu Val Arg
 50                  55                  60

Lys Phe Leu Gln Ala Asp Arg Val Cys Val Phe Lys Phe Glu Glu Asp
 65                  70                  75                  80

Tyr Ser Gly Thr Val Ser His Glu Ala Val Asp Asp Arg Trp Ile Ser
                85                  90                  95

Ile Leu Lys Thr Gln Val Gln Asp Arg Tyr Phe Met Glu Thr Arg Gly
            100                 105                 110

Glu Glu Tyr Val His Gly Arg Tyr Gln Ala Ile Ala Asp Ile Tyr Thr
        115                 120                 125

Ala Asn Leu Val Glu Cys Tyr Arg Asp Leu Leu Ile Glu Phe Gln Val
    130                 135                 140

Arg Ala Ile Leu Ala Val Pro Ile Leu Gln Gly Ser
145                 150                 155

<210> SEQ ID NO 7
<211> LENGTH: 156
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 7

Met Ala Ser Gly Lys Lys Leu Trp Gly Leu Val Ala His Gln Leu
 1               5                  10                  15

Ala Ala Pro Arg Ser Trp Gln Thr Trp Glu Ile Glu Phe Leu Lys Gln
            20                  25                  30

Gln Ala Val Val Met Gly Ile Ala Ile Gln Gln Ser Gly Gly Gly Gly
        35                  40                  45

Ser Ala Asn Leu Asp Lys Met Leu Asn Thr Ile Val Thr Glu Val Arg
 50                  55                  60

Gln Phe Leu Gln Val Asp Arg Val Cys Val Phe Gln Phe Glu Glu Asp
 65                  70                  75                  80

Tyr Ser Gly Ser Val Val Glu Ala Val Asp Asp Arg Trp Asn Ser
                85                  90                  95

Ile Leu Lys Thr Gln Val Arg Asp Cys Tyr Phe Met Glu Thr Arg Gly
            100                 105                 110

Glu Glu Tyr Leu His Gly Arg Tyr Gln Ala Ile Ala Asp Ile Tyr Gln
        115                 120                 125

Ala Asn Leu Leu Glu Ser Tyr Arg Asp Leu Leu Gly Gln Phe Gln Val
    130                 135                 140

Arg Ala Ile Leu Ala Val Pro Ile Ile Lys Gly Ser
145                 150                 155

<210> SEQ ID NO 8
<211> LENGTH: 157
<212> TYPE: PRT
<213> ORGANISM: ARTIFICIAL SEQUENCE
<220> FEATURE:
<223> OTHER INFORMATION: BASED ON Nostoc punctiforme SEQUENCE

<400> SEQUENCE: 8

Met Ala Ser Gly Lys Lys Leu Trp Gly Leu Phe Ser Ala His Gln Leu
```

```
                1               5                  10                 15
            Ala Ala Pro Arg Ser Trp Gln Ala Trp Glu Ile Glu Phe Leu Lys Gln
                        20                  25                 30
            Gln Ala Val Val Met Gly Ile Ala Ile Gln Gln Ser Gly Gly Gly Gly
                        35                  40                 45
            Ser Met Ala Asn Leu Asp Lys Met Leu Asn Thr Ile Val Thr Glu Val
                50                      55                 60
            Arg Gln Phe Leu Gln Val Asp Arg Leu Cys Val Phe Lys Phe Glu Glu
             65                      70                  75                 80
            Asp Tyr Ser Gly Asn Ile Ile Tyr Glu Ala Val Asp Asp Gly Trp Leu
                            85                  90                 95
            Ser Ile Leu Lys Thr His Val Arg Asp Cys Tyr Phe Met Glu Thr Arg
                        100                 105                110
            Gly Glu Glu Tyr Leu His Gly Arg Tyr Gln Ala Ile Ala Asp Ile His
                        115                 120                125
            Gln Ala Asn Leu Ala Glu Ser Tyr Arg Asp Phe Leu Thr Gln Tyr Gln
                        130                 135                140
            Val Arg Ala Ile Val Ala Val Pro Ile Leu Lys Gly Ser
            145                     150                155

<210> SEQ ID NO 9
<211> LENGTH: 145
<212> TYPE: PRT
<213> ORGANISM: Nostoc punctiforme

<400> SEQUENCE: 9

Asn Leu Asp Lys Val Leu Asn Thr Thr Val Thr Glu Val Arg Gln Phe
             1               5                  10                 15
            Leu Gln Val Asp Arg Val Phe Met Tyr Gln Phe Glu Pro Asp Tyr Ser
                        20                  25                 30
            Gly Val Val Val Glu Ser Val Asp Asp Arg Trp Ile Ala Ile Leu
                        35                  40                 45
            Asn Thr Gln Val Gln Asp Thr Tyr Phe Met Glu Thr Arg Gly Glu Glu
                50                      55                 60
            Tyr Ser His Gly Arg Ile Gln Ala Ile Ala Asp Ile Tyr Thr Ala Gly
             65                      70                  75                 80
            Leu Thr Glu Cys His Arg Asp Leu Leu Thr Gln Phe Gln Val Arg Ala
                            85                  90                 95
            Asn Leu Ala Val Pro Ile Leu Gln Gly Lys Lys Leu Trp Gly Leu Leu
                        100                 105                110
            Val Ala Asn Gln Cys Ala Ala Pro Arg Gln Trp Gln Thr Trp Glu Ile
                        115                 120                125
            Asp Phe Leu Lys Gln Leu Ala Val Gln Val Gly Ile Ala Ile Gln Gln
                        130                 135                140
            Ser
            145

<210> SEQ ID NO 10
<211> LENGTH: 441
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 10
atggcaaacc tggacaagat gctgaatacc acagtaacag aggtgcggca gttcctgcag          60
```

```
gtggacagag tgtgcgtgtt ccagtttgag gaggattata gcggagtggt ggtggtggag      120
gccgtggacg ataggtggat ctccatcctg aagacccagg tgcgggatag atacttcatg      180
gagacaaggg gcgaggagta ttctcacggc cgctaccagg ccatcgccga catctacacc      240
gcaaacctga cagagtgcta cagggatctg ctgacacagt tcaggtgag agcaatcctg       300 gccgtgccca tcctgcaggg caagaagctg tggggcctgt tggtggcaca ccagctggcg      360 gccccctagac agtggcagac ctgggagatc gactttctga agcagcaggc cgtggtggtg     420
ggcatcgcca tccagcagag c                                                441

<210> SEQ ID NO 11
<211> LENGTH: 441
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 11
atggcaaacc tggacaagat gctgaacacc accgtgaccg aggtgcgcaa gttcctgcaa       60
gcggacagag tgtgcgtgtt caagttcgag gaagattact ccggcaccgt ctcgcacgaa      120
gccgtggacg acagatggat tagcatcctg aagacccagg tgcaggacag atacttcatg      180
gaaaccagag gcgaggaata cgtccacggc agataccagg ccatcgccga catctacaca      240
gccaatctgg tcgagtgcta cagagacctg ctgatcgagt tcaggtgcg ggccattctg       300 gctgtcccca tcctgcaagg caagaagctg tggggcctgc tggtggccca ccaactggcc      360
ggccctcggg agtggcagac ctgggaaatc gacttcctga acagcaagc cgtggtgatg      420 ggcatcgcca tccagcagag c                                                441

<210> SEQ ID NO 12
<211> LENGTH: 441
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 12
atggcaaacc tggacaagat gctgaacacc atcgtgaccg aggtgcgcca gttcctgcaa       60
gtggacagag tgtgcgtgtt ccagttcgag gaagattact ccggcagcgt cgtcgtggaa      120
gccgtggacg acagatggaa cagcatcctg aagacccagg tgcgggactg ctacttcatg      180
gaaaccagag gtgaggaata cttgcacggc agataccagg ccatcgccga catctaccag     240
gccaatctgc tggagagcta cagagacctg ctgggccagt tcaggtgcg ggccattctg       300 gctgtcccca tcatcaaggg caagaagctg tggggcctgc tggtggccca ccaactggct      360 gccccctcgga gctggcagac ctgggaaatc gagttcctga acagcaagc cgtggtgatg      420 ggcatcgcca tccagcagag c                                                441

<210> SEQ ID NO 13
<211> LENGTH: 441
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 13
atggcaaacc tggacaagat gctgaacacc atcgtgaccg aggtgcgcca gttcctgcaa       60
gtggacagac tctgcgtgtt caagttcgag gaagattact ccggcaacat catctacgaa      120
```

```
gccgtggacg acggatggtt gagcatcctg aagacccacg tgcgggactg ctacttcatg    180
gaaaccagag gcgaggaata cctgcacggc agataccagg ccatcgccga catccaccag    240
gccaatctgg cggagagcta tagagacttc ctgacccagt accaggtgcg ggccattgtg    300
gctgtcccca tcctgaaggg caagaagctg tggggcttgt tcagcgccca ccaactggcc    360
gcccctcgga gctggcaggc ctgggaaatc gagttcctga acagcaagc cgtggtgatg    420 ggcatcgcca tccagcagag c                                              441
```

<210> SEQ ID NO 14
<211> LENGTH: 468
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 14

```
atggcctccg gcaagaagct gtggggcctg ttggtggcac accagctggc ggcccctaga     60
cagtggcaga cctgggagat cgactttctg aagcagcagg ccgtggtggt gggcatcgcc    120
atccagcaga gcggcggcgg cggcagcgca aacctggaca gatgctgaa taccacagta    180 acagaggtgc ggcagttcct gcaggtggac agagtgtgcg tgttccagtt tgaggaggat    240
tatagcggag tggtggtggt ggaggccgtg gacgataggg ggatctccat cctgaagacc    300
caggtgcggg atagatactt catggagaca aggggcgagg agtattctca cggccgctac    360
caggccatcg ccgacatcta caccgcaaac ctgacagagt gctacaggga tctgctgaca    420
cagtttcagg tgagagcaat cctggccgtg cccatcctgc agggcagc                 468
```

<210> SEQ ID NO 15
<211> LENGTH: 468
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 15

```
atggcctccg gcaagaagct gtggggcctg ctggtggccc accaactggc cggccctcgg     60
gagtggcaga cctgggaaat cgacttcctg aaacagcaag ccgtggtgat gggcatcgcc    120
atccagcaga gcggcggcgg cggcagcgca aacctggaca gatgctgaa caccaccgtg    180 accgaggtgc gcaagttcct gcaagcggac agagtgtgcg tgttcaagtt cgaggaagat    240
tactccggca ccgtctcgca cgaagccgtg gacgacagat ggattagcat cctgaagacc    300
caggtgcagg acagatactt catggaaacc agaggcgagg aatacgtcca cggcagatac    360
caggccatcg ccgacatcta cacagccaat ctggtcgagt gctacagaga cctgctgatc    420
gagtttcagg tgcgggccat tctggctgtc cccatcctgc aaggcagc                 468
```

<210> SEQ ID NO 16
<211> LENGTH: 468
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 16

```
atggcctccg gcaagaagct gtggggcctg ctggtggccc accaactggc tgccctcgg      60 agctggcaga cctgggaaat cgagttcctg aaacagcaag ccgtggtgat gggcatcgcc    120
```

```
atccagcaga gcggcggcgg cggcagcgca aacctggaca agatgctgaa caccatcgtg      180
accgaggtgc gccagttcct gcaagtggac agagtgtgcg tgttccagtt cgaggaagat      240
tactccggca gcgtcgtcgt ggaagccgtg gacgacagat ggaacagcat cctgaagacc      300
caggtgcggg actgctactt catggaaacc agaggtgagg aatacttgca cggcagatac      360
caggccatcg ccgacatcta ccaggccaat ctgctggaga gctacagaga cctgctgggc      420
cagtttcagg tgcgggccat tctggctgtc cccatcatca agggcagc                   468
```

```
<210> SEQ ID NO 17
<211> LENGTH: 471
<212> TYPE: DNA
<213> ORGANISM: ARTIFICIAL SEQUENCE
<220> FEATURE:
<223> OTHER INFORMATION: BASED ON Nostoc punctiforme SEQUENCE

<400> SEQUENCE: 17
```

```
atggcctccg gcaagaagct gtggggcttg ttcagcgccc accaactggc cgcccctcgg       60
agctggcagg cctgggaaat cgagttcctg aaacagcaag ccgtggtgat gggcatcgcc      120
atccagcaga gcggcggcgg cggcagcatg gcaaacctgg acaagatgct gaacaccatc      180
gtgaccgagg tgcgccagtt cctgcaagtg gacagactct gcgtgttcaa gttcgaggaa      240
gattactccg gcaacatcat ctacgaagcc gtggacgacg atggttgag catcctgaag       300 acccacgtgc gggactgcta cttcatggaa accgaggcg aggaatacct gcacggcaga      360
taccaggcca tcgccgacat ccaccaggcc aatctggcgg agagctatag agacttcctg      420
acccagtacc aggtgcgggc cattgtggct gtccccatcc tgaagggcag c               471
```

```
<210> SEQ ID NO 18
<211> LENGTH: 435
<212> TYPE: DNA
<213> ORGANISM: Nostoc punctiforme

<400> SEQUENCE: 18
```

```
aatttggaca aggttctcaa cactaccgtt actgaagtcc gtcaattcct gcaagtagat       60
cgagtgttca tgtatcagtt tgaaccagac tacagtgggg tggtggtggt agagtctgtt      120
gatgatcgtt ggattgctat cctgaatacc caagttcaag acacttattt catggaaact      180
cgcggcgagg agtacagtca tgggcgcatc caagctattg cagatattta tacagcaggt      240
ctgactgaat gccatcgcga tttacttact cagtttcaag tcagggcaaa cttggcggtt      300
ccaattttgc aaggaaaaaa attgtgggga ttattagttg ctaaccagtg tgcagcaccc      360
cgccagtggc agacgtggga aatcgatttt ctcaaacaat tggcagtaca ggtgggcatt      420
gccatccagc aatct                                                       435
```

```
<210> SEQ ID NO 19
<211> LENGTH: 158
<212> TYPE: PRT
<213> ORGANISM: Escherichia coli

<400> SEQUENCE: 19
```

Met Ala Leu Gln Asn Ile Phe Arg Ala Thr Ser Asp Glu Val Arg His
1               5                   10                  15

Leu Leu Ser Ser Asp Arg Val Leu Val Tyr Arg Phe Asn Pro Asp Trp
            20                  25                  30

Ser Gly Glu Phe Ile His Glu Ser Val Ala Gln Met Trp Glu Pro Leu
        35                  40                  45

```
Lys Asp Leu Gln Asn Asn Phe Pro Leu Trp Gln Asp Thr Tyr Leu Gln
 50                  55                  60

Glu Asn Glu Gly Gly Arg Tyr Arg Asn His Glu Ser Leu Ala Val Gly
 65                  70                  75                  80

Asp Val Glu Thr Ala Gly Phe Thr Asp Cys His Leu Asp Asn Leu Arg
                 85                  90                  95

Arg Phe Glu Ile Arg Ala Phe Leu Thr Val Pro Val Phe Val Gly Glu
                100                 105                 110

Gln Leu Trp Gly Leu Leu Gly Ala Tyr Gln Leu Gly Ala Pro Arg His
                115                 120                 125

Trp Gln Ala Arg Glu Ile His Leu Leu His Gln Ile Ala Asn Gln Leu
 130                 135                 140

Gly Val Ala Val Tyr Gln Ala Gln Leu Leu Ala Arg Phe Gln
 145                 150                 155
```

<210> SEQ ID NO 20
<211> LENGTH: 158
<212> TYPE: PRT
<213> ORGANISM: Escherichia coli

<400> SEQUENCE: 20

```
Met Ala Asp Val Glu Glu Ile Phe Lys Thr Thr Thr Gln Glu Val Arg
 1                   5                  10                  15

Gln Leu Leu Arg Ala Asp Arg Val Ala Val Tyr Arg Phe Asn Pro Asn
                 20                  25                  30

Trp Thr Gly Glu Phe Val Ala Glu Ser Val Ala His Thr Trp Val Lys
             35                  40                  45

Leu Val Gly Pro Asp Ile Lys Thr Val Trp Glu Asp Thr His Leu Gln
 50                  55                  60

Glu Thr Gln Gly Gly Arg Tyr Ala Gln Gly Glu Asn Phe Val Val Asn
 65                  70                  75                  80

Asp Ile Tyr Gln Val Gly His Ser Pro Cys His Ile Glu Ile Leu Glu
                 85                  90                  95

Gln Phe Glu Val Lys Ala Tyr Val Ile Val Pro Val Phe Ala Gly Glu
                100                 105                 110

Gln Leu Trp Gly Leu Leu Ala Ala Tyr Gln Leu Ser Gly Thr Arg Asp
                115                 120                 125

Trp Asp Glu Ser Glu Val Thr Leu Leu Ala Arg Ile Gly Asn Gln Leu
 130                 135                 140

Gly Leu Ala Leu Gln Gln Thr Glu Tyr Leu Gln Gln Val Gln
 145                 150                 155
```

<210> SEQ ID NO 21
<211> LENGTH: 147
<212> TYPE: PRT
<213> ORGANISM: Escherichia coli

<400> SEQUENCE: 21

```
Met Ala Asp Ile Phe Arg Ala Thr Thr His Asp Val Arg Glu Ser Leu
 1                   5                  10                  15

Gly Ser Asp Arg Val Val Val Tyr Lys Phe Phe Pro Asp Trp Ser Gly
                 20                  25                  30

Glu Phe Leu Val Glu Ala Thr Ala Pro Asn Ile Leu Pro Leu Ser Glu
             35                  40                  45

Leu Glu Val Pro Met Val Trp Gln Asp Thr Tyr Leu Gln Glu Asn Gln
 50                  55                  60
```

```
Gly Gly Lys Tyr Arg Asp Asn Ala Thr Thr Val Ala Asp Ile Tyr
65                  70                  75                  80

Gln Glu Ser Tyr Arg Asp Cys His Leu Glu Ile Leu Glu Trp Tyr Lys
                85                  90                  95

Ile Arg Ala Tyr Met Val Val Pro Val Phe Ile Gly Glu Thr Leu Trp
            100                 105                 110

Gly Leu Leu Ala Ala Tyr Gln Leu Asn Val Pro Arg Gln Trp His Lys
            115                 120                 125

Val Glu Leu Tyr Leu Leu Lys Gln Ala Gly Ala Gln Leu Gly Val Ala
130                 135                 140

Leu Gln Gln
145
```

<210> SEQ ID NO 22
<211> LENGTH: 159
<212> TYPE: PRT
<213> ORGANISM: Escherichia coli

<400> SEQUENCE: 22

```
Met Ala Asp Leu Asp Thr Ile Phe Gln Thr Thr Thr Gln Glu Ala Gln
1               5                   10                  15

Arg Leu Leu Asp Val Asp His Val Ala Val Tyr Gln Phe Asp Glu Asn
                20                  25                  30

Trp Gly Gly Ser Phe Ile Asn Asn Phe Arg Ala Val Lys Pro Glu Trp
            35                  40                  45

Glu Glu Val Val Tyr Ser Thr Arg Asp Val Trp Asn Asp Ser His Leu
        50                  55                  60

Gln Glu Thr Lys Gly Gly Arg Tyr Arg His Asn His Val Ser Val Val
65                  70                  75                  80

Asn Asp Val Ser Lys Ala Gly Leu Ser Pro Cys His Leu Glu Thr Tyr
                85                  90                  95

His Tyr Tyr Gln Ile Lys Ala Phe Leu Ile Ala Pro Val Phe Val Gly
            100                 105                 110

Ser Arg Leu Trp Gly Leu Ile Gly Ala Tyr Gln Leu Ser Asn Pro Tyr
        115                 120                 125

Glu Trp Lys Pro Leu Glu Val Asp Phe Ile Thr Gln Leu Ala Thr His
    130                 135                 140

Leu Gly Val Ala Val Gln Gln Ala Gly Ala Thr Glu Lys Val Gln
145                 150                 155
```

<210> SEQ ID NO 23
<211> LENGTH: 147
<212> TYPE: PRT
<213> ORGANISM: Escherichia coli

<400> SEQUENCE: 23

```
Met Ala Asp Ile Phe Ile Ala Thr Thr Glu Lys Val Arg Ala Ser Leu
1               5                   10                  15

Glu Ser Asp Arg Val Val Val Tyr His Phe Leu Pro Asp Trp Ser Gly
                20                  25                  30

Glu Phe Met Phe Glu Ser Ser Asp Thr Ser Phe Pro Pro Leu Val Thr
            35                  40                  45

Ala Asn Ser Thr Thr Asn Trp Glu Asp Thr Tyr Leu Gln Glu Thr Gln
        50                  55                  60

Gly Gly His Tyr Arg His Gln Ala Thr Thr Val Val Ala Asp Ile Tyr
65                  70                  75                  80
```

```
Glu Gln Gly Tyr Thr Asp Cys His Leu Ala Met Leu Glu Arg Phe His
                85                  90                  95

Ile Arg Ala Phe Met Val Val Pro Val Phe Val Gly Glu Lys Leu Trp
            100                 105                 110

Gly Leu Leu Ala Thr Tyr Gln Leu Thr Gln Ile Arg His Trp Gln Asp
        115                 120                 125

Leu Glu Leu Lys Leu Leu Lys Lys Val Gly Ala Gln Leu Gly Val Ala
    130                 135                 140

Leu Gln Gln
145

<210> SEQ ID NO 24
<211> LENGTH: 147
<212> TYPE: PRT
<213> ORGANISM: Escherichia coli

<400> SEQUENCE: 24

Met Ala Asp Ile Phe Thr Ala Thr Thr Glu Lys Val Arg Ala Ser Leu
1               5                   10                  15

Glu Ser Asp Arg Val Val Val Tyr His Phe Leu Pro Asp Trp Ser Gly
            20                  25                  30

Glu Phe Ile Phe Glu Ala Ser Asp Ser Ser Phe Leu Pro Leu Val Thr
        35                  40                  45

Ala Asn Thr Thr Thr Asn Trp Glu Asp Thr Tyr Leu Gln Glu Thr Gln
    50                  55                  60

Gly Gly Arg Tyr Arg His Gln Ala Thr Val Val Ala Asp Ile Tyr
65                  70                  75                  80

Glu Gln Gly Tyr Thr Asp Cys His Leu Ala Met Leu Glu Arg Phe His
                85                  90                  95

Ile Arg Ala Phe Met Val Val Pro Val Phe Val Gly Glu Lys Leu Trp
            100                 105                 110

Gly Leu Leu Ala Ala Tyr Gln Leu Ser Gln Ile Arg His Trp Gln Asp
        115                 120                 125

Leu Glu Leu Lys Leu Leu Arg Lys Val Gly Ala Gln Leu Gly Val Ala
    130                 135                 140

Leu Gln Gln
145

<210> SEQ ID NO 25
<211> LENGTH: 159
<212> TYPE: PRT
<213> ORGANISM: Escherichia coli

<400> SEQUENCE: 25

Met Ala Lys Glu Ile Leu His Thr Thr Val Thr Glu Val Gln Arg Ile
1               5                   10                  15

Leu Gln Ala Asp Arg Val Leu Ile Tyr His Val Leu Pro Asp Gly Thr
            20                  25                  30

Gly Lys Thr Ile Ser Glu Ser Val Leu Pro Asp Tyr Pro Thr Leu Met
        35                  40                  45

Asp Leu Glu Phe Pro Gln Glu Val Phe Pro Gln Glu Tyr Gln Gln Leu
    50                  55                  60

Tyr Ala Gln Gly Arg Val Arg Ala Ile Ala Asp Val His Asp Pro Thr
65                  70                  75                  80

Ala Gly Leu Ala Glu Cys Leu Val Glu Phe Val Asp Gln Phe His Ile
                85                  90                  95
```

Lys Ala Lys Leu Ile Val Pro Ile Val Gln Asn Leu Asn Ala Asn Ser
                100                 105                 110

Gln Asn Gln Leu Trp Gly Leu Leu Ile Ala His Gln Leu Asp Ser Val
            115                 120                 125

Arg Gln Trp Val Asp Phe Glu Leu Glu Leu Met Gln Gln Leu Ala Asp
    130                 135                 140

Gln Ile Ser Ile Ala Leu Ser Gln Ala Gln Leu Leu Gly Arg Leu
145                 150                 155

<210> SEQ ID NO 26
<211> LENGTH: 147
<212> TYPE: PRT
<213> ORGANISM: Escherichia coli

<400> SEQUENCE: 26

Met Ala Thr Ile Phe Leu Asn Val Leu Pro Ser Leu Arg Lys Gln Leu
1               5                   10                  15

Gln Ser Asp Arg Leu Ala Val Phe Arg Phe His Pro Asp Trp Ser Val
            20                  25                  30

Glu Phe Val Ala Glu Ser Val Lys Asp Lys Trp Leu Ser Leu Ala Asp
        35                  40                  45

Ser Asp Ile Lys Thr Ile Trp Met Asp Glu His Leu Gln Glu Thr Gln
    50                  55                  60

Gly Gly Arg Tyr Arg Asn His Glu Thr Phe Val Val Asn Asp Ile Tyr
65                  70                  75                  80

Thr Val Gly His Val Gln Cys Tyr Leu Glu Ile Leu Glu Lys Ile Gln
                85                  90                  95

Ala Lys Ala Tyr Ala Ile Ala Pro Ile Phe Ile Gly Asn Lys Leu Trp
            100                 105                 110

Gly Phe Ile Gly Ala Tyr Gln Leu Thr Gly Pro Arg Glu Trp Lys Ser
        115                 120                 125

Lys Asp Val Gln Leu Leu Arg Lys Val Ala Val Gln Met Gly Ile Gly
    130                 135                 140

Leu Gln Gln
145

<210> SEQ ID NO 27
<211> LENGTH: 164
<212> TYPE: PRT
<213> ORGANISM: Escherichia coli

<400> SEQUENCE: 27

Met Ala Asp Ile Ile Thr Ala Thr Thr Ala Glu Val Arg Ala Leu Leu
1               5                   10                  15

Gly Thr Asp Arg Val Met Ile Tyr Lys Phe His Pro Asp Gly Ser Gly
            20                  25                  30

Gln Val Ile Ala Glu Ser Ile Tyr Glu Asn Arg Leu Pro Ser Leu Leu
        35                  40                  45

Gly Leu Asn Phe Pro Ala Asp Asp Ile Pro Gln Ala Arg Glu Leu
    50                  55                  60

Leu Val Lys Ser Lys Val Arg Ser Ile Val Asp Val Ala Thr Gly Met
65                  70                  75                  80

Ile Gly Gln Ser Pro Val His Asp Leu Glu Thr Gly Glu Leu Ile Ser
                85                  90                  95

Glu Asp Ile Cys Tyr Arg Pro Val Asp Ser Cys His Val Glu Tyr Leu
            100                 105                 110

```
Thr Ala Met Gly Val Lys Ser Ser Val Val Ala Pro Ile Phe Cys Gln
            115                 120                 125

Asp Glu Leu Trp Gly Leu Leu Val Ser His His Leu Glu Asn Arg Thr
    130                 135                 140

Val Ser Glu Asp Glu Leu Glu Ala Met Gln Met Ile Val Asp Gln Leu
145                 150                 155                 160

Ala Val Ala Ile

<210> SEQ ID NO 28
<211> LENGTH: 149
<212> TYPE: PRT
<213> ORGANISM: Escherichia coli

<400> SEQUENCE: 28

Met Ala Asn Leu Asp Lys Val Leu Asn Thr Thr Val Thr Glu Val Arg
1               5                   10                  15

Gln Phe Leu Gln Val Asp Arg Val Phe Met Tyr Gln Phe Glu Pro Asp
                20                  25                  30

Tyr Ser Gly Val Val Val Val Glu Ser Val Asp Asp Arg Trp Ile Ala
            35                  40                  45

Ile Leu Asn Thr Gln Val Gln Asp Thr Tyr Phe Met Glu Thr Arg Gly
        50                  55                  60

Glu Glu Tyr Ser His Gly Arg Ile Gln Ala Ile Ala Asp Ile Tyr Thr
65                  70                  75                  80

Ala Gly Leu Thr Glu Cys His Arg Asp Leu Leu Thr Gln Phe Gln Val
                85                  90                  95

Arg Ala Asn Leu Ala Val Pro Ile Leu Gln Gly Lys Lys Leu Trp Gly
                100                 105                 110

Leu Leu Val Ala Asn Gln Leu Ala Ala Pro Arg Gln Trp Gln Thr Trp
            115                 120                 125

Glu Ile Asp Phe Leu Lys Gln Leu Ala Val Gln Val Gly Ile Ala Ile
        130                 135                 140

Gln Gln Ser Gln Leu
145
```

SMALL NEAR-INFRARED FLUORESCENT PROTEINS DEVELOPED FROM CYANOBACTERIOCHROME

CROSS-REFERENCE TO RELATED APPLICATIONS

This application claims the benefit of U.S. Provisional Patent Application No. 62/947,155, filed on Dec. 12, 2019, the contents of which are incorporated herein by reference in their entirety.

This application incorporates by reference nucleotide sequences which are present in the file named "00070-0005.txt", which is 33000 bytes in size, and which was created on Sep. 7, 2023 in the IBM-PC machine format, having an operating system compatibility with MS-Windows, which is contained in the text file filed Sep. 7, 2023 as part of this application.

STATEMENT OF GOVERNMENT SUPPORT

This invention was made with government support under grant GM122567 awarded by the National Institutes of Health. The government has certain rights in the invention.

FIELD OF THE INVENTION

Fluorescent proteins and nucleic acids that encode small monomeric fluorescent proteins derived from cyanobacteriochrome are provided. Also presented are methods of making and using such fluorescent proteins, including reagents, devices and kits for use in these methods.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Light absorption and fluorescence of GFP-like fluorescent proteins (FPs) are limited to a visible range of optical spectrum. Therefore, near-infrared (NIR) FPs and NIR biosensors are in high demand not only for deep-tissue in vivo imaging (1) but, even more importantly, for spectral multiplexing with biosensors based on GFP-like FPs and common optogenetic tools based on opsins, LOV and CRY domains that are activatable with blue-green light (2).

Bacterial photoreceptors have absorbance spectra in the near-infrared range due to covalently attached heme-derived linear tetrapyrrole compounds and allow engineering NIR FPs (1). Several photoreceptors from a class of bacterial phytochrome photoreceptors (BphPs) were developed into bright monomeric NIR FPs, which efficiently bind endogenous biliverdin (BV) tetrapyrrole in mammalian cells (3-5). However, the BphP-derived NIR FPs minimally require two domains, a PAS and a GAF, to covalently attach a BV chromophore and also possess a complex 'figure-of-eight knot' structure topologically linking the GAF and PAS domains, which affects their folding (1). The only example of a single-domain BphP-based FP, 20-kDa monomeric GAF-FP is dim in mammalian cells (6). Another class of bacterial photoreceptors, allophycocyanins (APCs), was also used to engineer NIR FPs, such as several BDFPs from ApcF and smURFP from TeAPC. Although the APC-based NIR FPs are smaller, they have low efficiency of BV binding, resulting in significantly lower brightness in mammalian cells than the BphP-derived NIR FPs (7-9).

To overcome the drawbacks of the BphP- and APC-based NIR FPs, we turned our attention to a class of cyanobacteriochrome (CBCR) photoreceptors found in cyanobacteria (10). Typical CBCRs consist of one or more GAF domains and effector domains (1, 10). GAF domains of CBCRs have several unique properties to consider them for engineering of NIR FPs. First, a single CBCR GAF domain is sufficient for autocatalytic binding of tetrapyrrole chromophore (11), potentially allowing to engineer single-domain FPs, twice smaller than BphP-derived FPs. This binding occurs via a conserved Cys residue located in the GAF domain, in contrast to the Cys in the PAS domain in BphPs. Second, GAF domains of CBCRs are naturally monomeric (12, 13), unlike typically dimeric BphPs and oligomeric APCs (1). Third, in contrast to BphPs and APCs, various CBCR subclasses exhibit a large spectral diversity and, moreover, a variety of photocycles in which GAF domains reversibly photoconvert between UV/blue, blue/green, green/red and red/NIR absorbing forms (14, 15). Fourth, CBCR GAF domains are also found as components of complex signaling proteins (16), suggesting that their structural fold is naturally optimized to use in fusion constructs (15).

Despite these advantages, CBCRs typically utilize phycocyanobilin (PCB) tetrapyrrole as a chromophore. PCB is naturally present in plant and cyanobacteria but not in mammalian cells, which produce BV (3, 17, 18). Therefore, to be used in live mammalian cells PCB-binding CBCRs require engineering into BV-binding proteins. Similar to BphPs, CBCRs are light-sensing signaling molecules, which use absorbed light energy to trigger photoisomerization of linear tetrapyrrole chromophore. Fluorescence and signaling compete in both CBCRs and BphPs. Suppression of chromophore photoisomerization leads to significant increase of BphPs fluorescence quantum yield and convert them to the bright fluorescence proteins (19). Hence, engineering of CBCR-based NIR FPs also require suppression of chromophore photoisomerization (1).

Recently, three CBCR GAF domains from *Acaryochloris marina* were shown to bind both PCB and BV (20-22). However, they demonstrated weak fluorescence in mammalian cells and only in the presence of exogenous PCB chromophore (22).

Also, for development of NIR reporters and biosensors and for multi-color NIR protein labeling spectrally distinct versions of small monomeric NIR FPs are necessary.

Thus, there is a need in the art for the development of small bright monomeric spectrally distinct NIR FPs that find use in scientific applications without technical limitations due to oligomerization and complex structure. There exists also a need for methods to produce such FPs.

Here we report a bright NIR FP, called miRFP670nano, which was engineered from a single domain of cyanobacteriochrome. We also report a set of three bright spectrally distinct NIR FPs miRFP670nano3, miRFP704nano and miRFP718nano. miRFPnanos are monomeric FPs with molecular weight of 17 kDa that is 2-fold smaller than bacterial phytochrome (BphP)-based NIR FPs and 1.6-fold smaller than GFP-like FPs. We demonstrated that similar to BphP-based proteins, the CBCR-derived NIR FPs brightly fluoresce in mammalian cells without supplementation of exogenous BV chromophore. Characterization of the developed NIR FPs showed their numerous advantages over NIR FPs developed from other photoreceptors, including mono-

SUMMARY OF THE INVENTION

The present invention provides a method to convert PCB-binding CBCR GAF domain into BV binding NIR FP.

The present invention also describes a method, to obtain spectrally distinct mutants of miRFP670nano.

The present invention satisfies the needs stated above and provides additional advantages.

The present invention addresses the need for bright spectrally distinct genetically encoded small near-infrared FPs, uses thereof, and methods to produce these FPs.

The present invention also provides NIR fluorescent reporters based on the engineered small monomeric NIR FPs and uses thereof.

This invention provides non-naturally occurring mutants of a CBCR NpR3784 GAF domain, from the cyanobacterium *Nostoc punctiforme*. Being expressed in any cell containing BV, these mutant CBCR GAF domains spontaneously incorporate BV and become fluorescent in the NIR region. Notably, BV is abundant in mammalian tissues as an intermediate in heme metabolism. The mutants vary in their spectral properties that is important for their applications.

This invention provides an isolated protein comprising consecutive amino acid residues having the sequence set forth in miRFP670nano (SEQ ID NO:1), miRFP670nano3 (SEQ ID NO:2), miRFP704nano (SEQ ID NO:3), or miRFP718nano (SEQ ID NO:4), or having 90% or greater identity to one of SEQ ID NO:1, SEQ ID NO:2, SEQ ID NO:3, or SEQ ID NO:4.

This invention also provides an isolated nucleic acid encoding a protein comprising consecutive amino acid residues having the sequence set forth in miRFP670nano (SEQ ID NO:1), miRFP670nano3 (SEQ ID NO:2), miRFP704nano (SEQ ID NO:3), or miRFP718nano (SEQ ID NO:4). This invention also provides an isolated nucleic acid encoding a protein comprising consecutive amino acid residues having 90% or greater identity to one of SEQ ID NO:1, SEQ ID NO:2, SEQ ID NO:3, or SEQ ID NO:4.

In another embodiment, the invention provides an isolated nucleic acid encoding a protein comprising, wherein the protein comprises at least one amino acid residue selected from the group consisting of M7, I11, K17, A21, L24, C25, V26, F27, K28, E31, T36, S36, N36, I37, I38, S38, Y39, H39, A41, G45, L47, N47, S48, K51, H53, R55, C57, R57, V68, L68, Y72, H79, Q80, N82, A84, L84, V84, S86, Y87, F90, G92, I92, E93, Y94, I99, V100, I105, K106, F114, S115, H117, L119, G121, S124, E124, A127, E131, Q136, V139, M140 of SEQ ID NOs:1-4.

This invention also provides circular permutated variants of FPs having the sequence set forth in miRFP670nano (SEQ ID NO:1), miRFP670nano3 (SEQ ID NO:2), miRFP704nano (SEQ ID NO:3), or miRFP718nano (SEQ ID NO:4), or having 90% or greater identity to one of SEQ ID NO:1, SEQ ID NO:2, SEQ ID NO:3, or SEQ ID NO:4.

This invention provides an isolated protein comprising consecutive amino acid residues having the sequences of circular permutated variants of miRFP670nano (SEQ ID NO:5): miRFP670nano3 (SEQ ID NO:6), miRFP704nano (SEQ ID NO:7), or miRFP718nano (SEQ ID NO:8), or having 90% or greater identity to one of SEQ ID NO:5, SEQ ID NO:6, SEQ ID NO:7, or SEQ ID NO:8.

This invention also provides an isolated nucleic acid encoding a protein comprising consecutive amino acid residues having the sequences of circular permutated variants of miRFP670nano (SEQ ID NO:5): miRFP670nano3 (SEQ ID NO:6), miRFP704nano (SEQ ID NO:7), or miRFP718nano (SEQ ID NO:8). This invention also provides an isolated nucleic acid encoding a protein comprising consecutive amino acid residues having 90% or greater identity to one of SEQ ID NO:5, SEQ ID NO:6, SEQ ID NO:7, SEQ ID NO:8.

This invention provides insertion mutants of miRFP670nano (SEQ ID NO:1), miRFP670nano3 (SEQ ID NO:2), miRFP704nano (SEQ ID NO:3), or miRFP718nano (SEQ ID NO:4), such as having the sequences of calmodulin-M13 pair (23, 24) at positions 50, 51, 52, 53, 54, 55, wherein the amino acid positions correspond to amino acid residue number positions in SEQ ID NO:1, or having 90% or greater identity to those insertions mutants.

In another embodiment, the invention provides a method for the generation of BV-binding variants of a FP derived from a CBCR GAF domain, comprising the mutagenesis of amino acid residues in the FP to produce a BV-binding FP variant.

Also provided is a composition comprising any one or more of the isolated proteins, isolated nucleic acids, or the nucleic acid constructs described herein.

The invention also provides a host cell comprising any one or more of the isolated proteins, isolated nucleic acids, or the nucleic acid constructs described herein, wherein the host cell is not a cell in a human.

The invention also provides a host cell comprising a nucleic acid construct, said nucleic acid construct comprising at least a portion encoding one of the proteins as described herein, wherein the host cell is not a cell in a human.

The invention provides a kit, said kit comprising a nucleic acid as described herein, or a nucleic acid construct as described herein, and instructions for use thereof.

The invention provides a method of optical imaging, the method comprising the step of expressing in a cell a nucleic acid sequence encoding one of the proteins as described herein and detecting or quantifying fluorescence therefrom.

Also provided is a fusion protein comprising (i) consecutive amino acid residues having the sequence set forth in miRFP670nano (SEQ ID NO:1), miRFP670nano3 (SEQ ID NO:2), miRFP704nano (SEQ ID NO:3), miRFP718nano (SEQ ID NO:4), circular permutated variants of miRFP670nano (SEQ ID NO:5): miRFP670nano3 (SEQ ID NO:6), miRFP704nano (SEQ ID NO:7), and miRFP718nano (SEQ ID NO:8) or a protein with 90% or greater identity to one of SEQ ID NOS:1-8, joined at a terminus thereof to a peptide, polypeptide, or protein of interest by a peptide bond.

The invention provides a method of detecting the changes in the Forster resonance energy transfer (FRET) between the disclosed FPs comprising consecutive amino acid residues having the sequence set forth in miRFP670nano (SEQ ID NO:1), miRFP670nano3 (SEQ ID NO:2), miRFP704nano (SEQ ID NO:3), miRFP718nano (SEQ ID NO:4), circular permutated variants of miRFP670nano (SEQ ID NO:5): miRFP670nano3 (SEQ ID NO:6), miRFP704nano (SEQ ID NO:7), and miRFP718nano (SEQ ID NO:8) or a protein with 90% or greater identity to one of SEQ ID NOS:1-8, and its partner in a variety of FRET-based biosensors, including NIR PKA and JNK biosensors and caspase sensor.

The present invention relates to a diagnostic composition as well as a kit and to methods of detecting the expression of a gene of interest, detecting the activity of a promoter of interest, detecting the presence of a protein of interest, detecting the localization of a polypeptide or a fusion protein of the invention in a cell or tissue, detecting the changes in the protein level of a polypeptide or a fusion protein as a reporter of a process of interest, detecting the changes in the FRET between the disclosed FP and its partner in a variety of FRET-based biosensors, including NIR PKA and JNK biosensors and caspase sensor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10. Alignment of the amino acid sequences of NIR FPs miRFP670nano (SEQ ID NO:1), miRFP670nano3 (SEQ ID NO:2), miRFP704nano (SEQ ID NO:3) and miRFP718nano (SEQ ID NO:4) with wild-type GAF domain of parental CBCR NpR3784 (SEQ ID NO:9). The amino acid substitutions highlighted in yellow are mutations relative to parental CBCR NpR3784 GAF domain.

FIG. 14(a)-14(d). miRFP670nano as internally inserted fluorescent tag. (a) miRFP670nano and (b) miRFP670 inserted between the helical and GTPase domains of the G protein α subunit. (c) miRFP670nano and (d) miRFP670 inserted into the intracellular loop 3 of the β2 adrenergic receptor. mVenus with membrane targeting CAAX motif used for membrane visualization. Scale bars, 10 µm.

DETAILED DESCRIPTION OF THE INVENTION

Figures 1A, 1B, 1C:
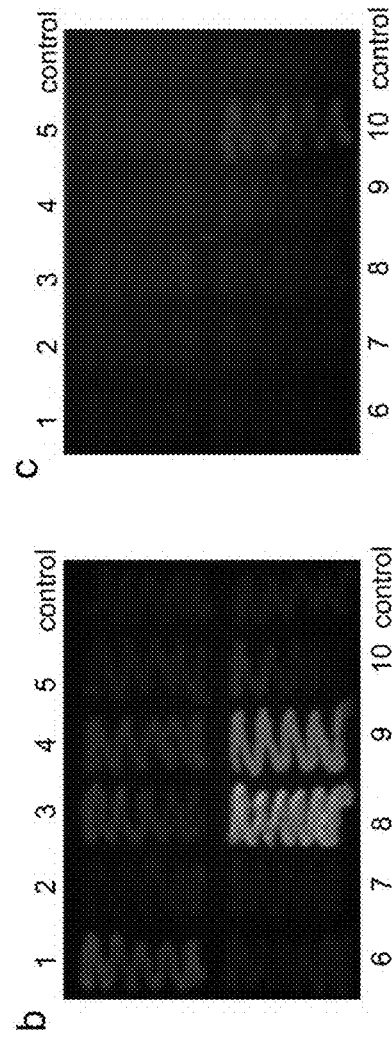
FIG. 1(a)-1(c). Evaluation of CBCR GAF domains as templates for NIR FP. (a) Alignment of the amino acid sequences of evaluated CBCR GAF domains. Identical amino acid residues are highlighted in yellow, conserved amino acid residues are highlighted in green. Met and Ala added to N-terminus and introduced Leu are highlighted in blue. Numbering follows that for NpR3784 sequence. SEQ ID NOS:19 to 28, respectively. (b) CBCR GAF domains expressed in PCB-producing E. coli. (c) CBCR GAF domains expressed in BV-producing E. coli. 1-slr1393g3 (a.a. 441-596); 2-Npr6012g4 (a.a. 600-755); 3-AM1_1557g2 (a.a. 220-364); 4-AM1_1870g3 (a.a. 513-668); 5-AM1_6305g2 (a.a. 240-384); 6-WP_010470102g2 (a.a. 254-398); 7-RcaEg (a.a. 115-271); 8-NpF2164g5 (a.a. 873-1017); 9-all2699g1 (a.a. 34-195); 10-NpR3784g (a.a. 44-189); control-bacteria transformed with empty plasmid.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In embodiments, the fluorescent protein does not consist of SEQ ID NO:9, where SEQ ID NO:9 is the NpR3784 GAF domain. In embodiments, the fluorescent protein does not comprise SEQ ID NO:9, where SEQ ID NO:9 is the NpR3784 GAF domain.

As summarized above, this disclosure provides nucleic acid molecules encoded FPs miRFP670nano, miRFP670nano3, miRFP704nano, miRFP718nano, their circular permutated variants, mutants and derivatives thereof, and proteins and peptides encoded by these nucleic acids. The invention also relates to vectors and expression cassettes comprising these nucleic acids, and stable cell lines, transgenic animals, and transgenic plants comprising these nucleic acids, vectors or expression cassettes. The invention also relates to methods of producing these FPs and mutants thereof, and antibodies specifically binding to these FPs and mutants or fragments thereof. Also provided are methods that use a FP of the present invention or the nucleic acid encoding it. The invention also relates to kits comprising nucleic acids or vectors or expression cassettes harboring the nucleic acids, or proteins of the present invention are provided.

Definitions

Various terms relating to the biological molecules of the present invention are used herein above and also throughout the specifications and claims.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a FP variant of the invention linked to a polypeptide of interest. The term "recombinant host cell" refers to a cell that contains a recombinant nucleic acid molecule. As such, a recombinant host cell can express a polypeptide from a "gene" that is not found within the native (nonrecombinant) form of the cell.

As used herein the term "FP" means a protein that is fluorescent; e.g., it may exhibit low, medium or intense fluorescence upon irradiation with light of the appropriate excitation wavelength. The fluorescent characteristic of FP is one that arises from the chromophore wherein the chromophore results from autocatalytic cyclization of two or more amino acid residues in the polypeptide backbone. As such, the FPs of the present invention do not include proteins that exhibit fluorescence only from residues that act by themselves as intrinsic fluors, i.e., tryptophan, tyrosine and phenylalanine.

The term "cyanobacteriochromes" refers to phytochrome-related photoreceptor proteins found in the cyanobacteria which require only a GAF domain for attachment of a tetrapyrrole chromophore.

As used herein the term "isolated" means a molecule or a cell that is an environment different from that in which the molecule or the cell naturally occurs, or which is non-naturally occurring.

As used herein, unless otherwise contradicted by context, the terms "mutant" or "derivatives" or "variant" refer to protein disclosed in the present invention, in which one or more amino acids are added and/or substituted and/or deleted and/or inserted at the N-terminus, and/or the C-terminus, and/or within the native amino acid sequences of the proteins of the present invention. As used herein the term "mutant" refers to a nucleic acid molecule that encodes a mutant protein. Moreover, the term "mutant" refers to any shorter or longer version of the protein or nucleic acid herein.

As used herein, "homologue" or "homology" is a term used in the art to describe the relatedness of a nucleotide or peptide sequence to another nucleotide or peptide sequence, which is determined by the degree of identity and/or similarity between said sequences compared.

As used herein, an amino acid sequence or a nucleotide sequence is "substantially the same as" or "substantially similar to" a reference sequence if the amino acid sequence or nucleotide sequence has at least 80% sequence identity with the reference sequence over a given comparison window. Thus, substantially similar sequences include those having, for example, at least 80% sequence identity, at least 90% sequence identity, at least 95% sequence identity or at least 99% sequence identity. Two sequences that are identical to each other are also substantially similar. For purposes of this invention, the length of comparison sequences of FP will generally be at least 105 amino acids, preferably at least 200 amino acids. For nucleic acids, the length of comparison sequences will generally be at least 315 nucleotides, preferably at least 600 nucleotides.

Sequence identity is calculated based on a reference sequence. Algorithms for sequence analysis are known in the art, such as BLAST, described in (25). For purposes of this invention comparisons of nucleic acid or amino acid sequences are performed with Blast software provided by the National Center for Biotechnology Information using a gapped alignment with default parameters, may be used to determine the level of identity and similarity between nucleic acid sequences and amino acid sequences.

As used herein, the term "related FP" refers to a FP that has a substantially same amino acid sequence when compared to a reference FP. In general, a related FP, when compared to the reference FP sequence, has a contiguous sequence of at least about 125 amino acids that shares at least 85% sequence identity with the reference FP.

As used herein the term "miRFPnano-related protein" refers to the protein of SEQ ID NOS: 1-8, and functional mutants thereof. The term "miRFPnano-related nucleic acid" refers to a nucleic acid that encodes an miRFPnano-related protein (e.g. SEQ ID NOs: 1-8). As used herein miRFPnano-related protein comprises an amino acid sequence that is substantially the same as or identical to the sequences SEQ ID NOs: 1-8. The terms "miRFPnano-related protein" and "miRFPnano-related nucleic acid" also refers to shorter or longer variants of miRFPnanos and their mutants and nucleic acids encoding them.

As used herein, the term "functional" implies that the nucleic or amino acid sequence is functional for the recited assay or purpose. The term "functional" when used to describe FPs means that the protein has useful excitation and emission spectra (i.e., possesses detectable fluorescence).

As used herein, "biochemical property" refers to the protein folding and maturation rate, half-life before degradation, aggregation capacity, pH or temperature stability and optimum, and other like properties.

As used herein, "fluorescent property" or "spectral property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

As used herein, the term "effective brightness" in cells refers to the fluorescent signal corresponding to the cell expressing a specific FP. In contrast to molecular brightness, which is well known in the art and that depends solely on extinction coefficient and quantum yield of the FP, effective brightness of a FP in mammalian cells depends on molecular brightness, intracellular stability, efficiency of BV incorporation, and cell expression level. In contrast to GFP-like FPs, the effective brightness of NIR FPs does not always correlate with their molecular brightness (26). Decreased cellular fluorescence of some NIR FPs results from a low specificity of BV binding and a competition between BV and other heme-derived compounds, including protoporphyrin IX, for binding to NIR FP apoproteins (27, 28).

The term "operatively linked" or "operably linked" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a FP of the present invention can be fused to a fusion partner of interest. In this case, the fusion molecule retains its fluorescence, and the polypeptide of interest retains its original biological activity. In some embodiments of the present invention, the activities of either the FP or the protein of interest can be reduced relative to their activities in isolation. Such fusions can also find use with the present invention.

As used herein the term "specifically hybridize" refers to the association between two single-stranded nucleic acid molecules of sufficiently complementary sequence to permit such hybridization under pre-determined conditions generally used in the art (sometimes termed "substantially complementary").

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a FP variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard tech niques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified. variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another: 1) Alanine (Ala, A), Serine (Ser, S), Threonine (Thr, T); 2) Aspartic acid (Asp, D), Glutamic acid (Glu, E); 3) Asparagine (Asn, N), Glutamine (Gln, Q); 4) Arginine (Arg, R), Lysine (Lys, K); 5) Isoleucine (Ile, I), Leucine (Leu, L), Methionine (Met, M), Valine (Val, V); and 6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

For miRFPnanos (SEQ ID NOs: 1-4) numeration of amino acid residues and substitutions follows that for miRFP670nano sequence (SEQ ID NO: 1). For mutant proteins, the position of the amino acid residue or substitution should be determined using protein alignment.

Nucleic Acid Molecules

The present invention provides nucleic acid molecules encoding FPs miRFP670nano, miRFP670nano3, miRFP704nano, miRFP718nano and their circular permutants, (SEQ ID NOs: 1-8) and mutants thereof. Nucleic acid molecules encoding shorter or longer variants of the miRFPnano-related proteins or their mutants are also in the scope of the invention. A nucleic acid molecule as used herein is DNA molecules, such as genomic DNA molecules or cDNA molecules, or RNA molecules, such as mRNA molecules. In particular, the nucleic acid molecule is a cDNA molecule having an open reading frame that encodes a FP of the invention and is capable, under appropriate conditions, of being expressed as a FP according to the invention. The invention also encompasses nucleic acids that are homologous, substantially similar to, identical to, derived from, or mimetics of the nucleic acids encoding proteins of the present invention. The subject nucleic acids are present in an environment other than their natural environment; e.g., they are isolated, present in enriched amounts, present or expressed in vitro or in a cell or organism other than their naturally occurring environment.

Specific nucleic acid molecules of interest include nucleic acid molecules that encode the following FPs, and homologs/derivates/mutants thereof: miRFP670nano (SEQ ID NO:1), miRFP670nano3 (SEQ ID NO:2), miRFP704nano (SEQ ID NO:3), or miRFP718nano (SEQ ID NO:4), circular permutated miRFP670nano (SEQ ID NO:5), circular permutated miRFP670nano3 (SEQ ID NO:6), circular permutated miRFP704nano (SEQ ID NO:7), circular permutated miRFP718nano (SEQ ID NO:8). Each of these particular types of nucleic acid molecules of interest is discussed below and in the experimental section.

Each of these particular types of nucleic acid molecules of interest is discussed below in more detail in the experimental part.

Nucleic acid molecules encoding the FPs of the invention may be synthesized from appropriate nucleotide triphosphates. The method of enables preparation of isolated nucleic acid molecules of the invention by oligonucleotide synthesis is well-known in the art. In the case of amino acid sequence information, a number of nucleic acids that differ from each other due to degenerate code may be synthesized. The methods to select codon usage variants for desired hosts are well known in the art.

In addition to the above described specific nucleic acid compositions, also of interest are homologues of the above sequences. With respect to homologues of the subject nucleic acids, the source of homologous genes may be any species of plant or animal or the sequence may be wholly or partially synthetic (e.g. genetically engineered). In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 contiguous nucleotides long, more usually at least about 30 contiguous nucleotides long, and may extend to the complete sequence that is being compared. Algorithms for sequence analysis are known in the art, such as BLAST, described in (25) (using default settings, i.e. parameters w=4 and T=17). The sequences provided herein are essential for recognizing related and homologous nucleic acids in database searches. Also of interest are nucleic acids of substantially the same length as the nucleic acid identified as SEQ ID NOS:1-8, where by substantially the same length is meant that any difference in length does not exceed about 10%, usually does not exceed about 5%; and have sequence identity to any of these sequences of about 90% or more, usually at least about 95% and more, usually at least about 99% over the entire length of the nucleic acid. In many embodiments, the nucleic acids have a sequence that is substantially similar (i.e. the same as) or identical to the sequences of SEQ ID NOS:1-8. By substantially similar is meant that sequence identity will generally be at least about 90%, usually at least about 95% and often at least about 96%, 97%, 98%, or even 99%.

Mutants or derivatives can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any convenient method, including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and combinations thereof, e.g., (29-31) and Sambrook et al., Molecular Cloning: A Laboratory Manual, (1989), CSH Press, pp. 15.3-15.108. The FPs encoded by mutant or derived nucleic acids may have the same fluorescent or biochemical properties as the initial FP. Alternatively, the mutant or derived nucleic acids may encode FPs with altered properties, e.g., they can have altered photostability, oligomerization state, excitation and emission spectra, quantum yield, extinction coefficient.

In addition, degenerate variants of the nucleic acids that encode the proteins of the present invention are also provided. Degenerate variants of nucleic acids are nucleic acids in which the amino-acid encoding codons are replaced with other codons encoding the same amino acids. For example, degenerate variants of a nucleic acid are generated to increase its expression in a host cell. In this embodiment, codons of the nucleic acid that are non-preferred or are less preferred in the host cell are replaced with the codons over-represented in coding sequences in genes in the host cell, wherein the replaced codons encodes the same amino acid.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest further may include 5' an 3' non-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region.

The nucleic acid molecules of the invention may encode all or a part of the FPs having amino acid sequences represented by SEQ ID NOs: 1-10 or mutants thereof. In certain embodiments, the nucleic acid molecules encodes complete or truncated (minimum) of the subject proteins that are capable to be fluorescent when expressed in vitro and\or in vivo.

Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length, about 100, about 200, about 300, about 400, about 500, about 600, about 700 contiguous nucleotides or greater in length. The DNA fragment may share 50%, 55%, 60%, 65%, 70%, 75% or more sequence identity with a fragment of the subject nucleic acid, e.g. 80%, 85%, or 90% or more identity, more often 92%, 95%, 96%, 97%, 99% or more, e.g. 100% identity with a fragment of the subject nucleic acid that is about 15 contiguous nucleotides in length, about 18 contiguous nucleotides in length, about 25 contiguous nucleotides in length, about 50 contiguous nucleotides in length, or about 100, about 200, about 300, about 400, about 500, about 600, or about 700 contiguous nucleotides or greater in length.

The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids, 214 amino acids; 215 amino acids; 217 amino acids; 218 amino acids; 219 amino acids; 220 amino acids; up to the full length protein.

The subject nucleic acids may be isolated and obtained in substantially purified form. Substantially purified form means that the nucleic acids are at least about 80% pure, usually at least about 90% pure and are typically "recombinant", i.e., flanked by one or more nucleotides with which they are not normally associated on a naturally-occurring chromosome in a natural host organism.

The nucleic acids of the present invention, e.g. the corresponding cDNAs, full-length genes and constructs can be generated synthetically by a number of different protocols known to those of skill in the art. Appropriate nucleic acid constructs are purified using standard recombinant DNA techniques as described in, for example, and Sambrook et al., Molecular Cloning: A Laboratory Manual, (1989), CSH Press, and under regulations described in, e.g., United States Dept. of HHS, National Institute of Health (NIH) Guidelines for Recombinant DNA Research.

Nucleic acids encoding shorter or longer variants of the SEQ ID Nos 1-8 or mutants thereof are also in the scope of the invention. As used herein, these protein variants comprise amino acid sequences of miRFPnano-related protein with modified C-, N-, or both termini. In longer variants, the C- or N-terminus of the protein may comprise additional amino acid residues. In shorter variants one or more (usually up to 30, more usually up to 22 and preferably up to 13) amino acid residues should be eliminated from the sequence or replaced by any other amino acid residues. Such modifications do not substantially alter fluorescent properties of the proteins, but can facilitate protein folding in host cells, decrease aggregation capacity or modulate other biochemical properties of the proteins, for example, cellular brightness. In some embodiments, these modifications do not modify biochemical properties of the protein. All types of modifications and mutations noted above are performed at the nucleic acid level.

The nucleic acid molecules of the invention may encode all or a part of the subject proteins. Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 nucleotides or greater in length. The subject nucleic acids may encode fragments of the subject proteins or the full-length proteins; e.g., the subject nucleic acids may encode polypeptides of about 25 amino acids, about 50, about 75, about 100, about 125, about 150, or about 200 amino acids up to the full length protein.

The subject nucleic acids may be isolated and obtained in substantially purified form. Substantially purified form means that the nucleic acids are at least about 50% pure, usually at least about 90% pure and are typically "recombinant", i.e., flanked by one or more nucleotides with which it is not normally associated on a naturally-occurring chromosome in its natural host organism.

Also provided are nucleic acids that encode fusion proteins comprising a FP of the present invention that are discussed in more details below.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject chromogenic or FPs or fusion proteins thereof or for replication of the subject nucleic acid molecules. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operatively linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g., co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus oocytes*, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

Proteins

Also provided by the subject invention are FPs, derivatives, and mutants thereof including full-length proteins, as well as portions or fragments thereof.

As discussed above, specific FPs of interest include the following FPs: miRFP670nano (SEQ ID NO:1), miRFP670nano3 (SEQ ID NO:2), miRFP704nano (SEQ ID NO:3), or miRFP718nano (SEQ ID NO:4) and circular permutated miRFP670nano (SEQ ID NO:5), circular permutated miRFP670nano3 (SEQ ID NO:6), circular permutated miRFP704nano (SEQ ID NO:7), circular permutated miRFP718nano (SEQ ID NO:8). Also of interest are mutants and fragments thereof.

Homologs that vary in sequence from the above provided specific amino acid sequences of the subject invention, i.e., SEQ ID NOs: 1-8 are also provided. By homolog is meant a protein having 50% or more, usually 55% or more and more usually 60% or more amino acid sequence identity to amino acid sequences of referred protein as determined using MegAlign, DNAstar clustal algorithm as described in (32) (using parameters ktuple 1, gap penalty 3, window 5 and diagonals saved 5). In many embodiments, homologs of interest have much higher sequence identity e.g., 70% or more, 75% or more, 80% or more, 85% or more, 90% or more (e.g., 92% or more, 93% or more, 94% or more), e.g., 95% or more, 96% or more, 97% or more, 98% or more, 99% or more, or 99.5%, particularly for the amino acid sequence that provides the functional regions of the protein.

Also provided are proteins that are substantially identical to the proteins of SEQ ID NOs: 1-8, where by substantially identical is meant that the full-length protein or fragment thereof has an amino acid sequence identity to the sequence of reference protein or fragment of 82% or more, in some instances, 92% or more, or 95% or more, where in some instances the identity may be much higher, e.g., at least 96%, at least 97%, at least 98%, at least 99% or higher.

As used herein, "82% or greater identity" with regard to a sequence (e.g. of amino acid residues) means a 82.0%-99.9% identity of sequence with the referenced SEQ ID NO. One skilled in the art is aware of the most conservative amino acid residue changes that can be made with an expectation of retention of function in the sequence having the 82% or greater identity, and these are encompassed by the present invention. The function retained is retained qualitatively (e.g. fluorescence under the same conditions) even though quantitatively the function may be less than, or in excess of, the level of that function in the referenced sequence. In addition, 82.0%-99.9% identity is understood to encompass every sub-range in between these two values to the first tenth of a percent, for example 91.0%-91.5%; 90.0%-97.2% etc., as well as every single value identity, for example, 95%, 96%, 97%, 98% or 99% or greater identity. Specifically excluded from this definition are sequences which possess a 90% or greater identity but which also are naturally occurring sequences, such as the cyanobacteriochrome NpR3784 domain (SEQ ID NO:9) on which miRFP670nano, miRFP670nano3, miRFP704nano and miRFP718nano, their circular permutants and insertions mutants are based.

In aspects of the invention, subject proteins and mutants thereof range in length from about 100 to 350 amino acids, more usually from about 105 to 350 amino acid residues. In aspects of the invention, the subject proteins and mutants thereof have a molecular weight ranging from about 11.6 to 38.5 kDa, more usually from about 17.0 to 38.5 kDa, where the molecular weight is the average molecular weight, i.e. the calculated molecular weight based upon the average weight for amino acids of 0.11 kDa per amino acid.

In aspects of the invention, the subject proteins are bright, where by bright is meant that they exhibit fluorescence that can be detected by common methods (e.g., visual screening, spectrophotometry, spectrofluorometry, fluorescence microscopy, by FACS machines, etc.) Fluorescence brightness of particular FPs is determined by its quantum yield multiplied by maximal extinction coefficient.

Additional mutations contemplated include N-terminal truncations or extensions, and/or C-terminal truncations or extensions. In an embodiment, the proteins comprising consecutive amino acid residues having 82% or greater identity to one of SEQ ID NO:1, SEQ ID NO:2, SEQ ID NO:3, SEQ ID NO:4, SEQ ID NO:5, SEQ ID NO:6, SEQ ID NO:7, SEQ ID NO:8 comprises a truncated or extended variants of these protein sequences.

Aspects of the invention include mutants and variants which retain biological properties of the initial proteins (e.g., proteins subjected for mutagenesis). In other aspects of the invention, mutants and variants have biological properties which differ from the initial proteins. The term "biological property" of the proteins of the present invention refers to, without limitation, spectral properties, such as absorbance maximum, emission maximum, maximum extinction coefficient, brightness, effective brightness in cells, and the like; and biochemical properties, such as in vivo and/or in vitro stability (e.g., half-life), aggregation/oligomerization tendency, and other such properties.

Also provided are proteins that comprise one or more substitutions that shifts the fluorescence of the protein spectrally, i.e. it has an absorbance maximum ranging from about 630 nm to 710 nm, usually from about 635 nm to 695 nm, while the maximum of emission spectra of the subject proteins typically ranges from about 660 nm to 750 nm, usually from about 665 nm to 720 nm while in many embodiments the maximum of emission spectra ranges from about 670 to 720 nm. In some embodiments, the substitution is at a position corresponding to residues 57 and/or 86 and/or 90, and/or 124 comparing to SEQ ID NO:9 (in non-limiting examples, T57R, T57C, C86S, L90F, V124S).

Also provided are proteins that are substantially the same as the above provided specific proteins, whereby substantially the same means that the protein has an amino acid sequence identity to the sequence of wild type protein of at least about 82% sequence identity, usually at least about 90% and more usually at least about 95%, (e.g. 95%; 96%, 97%; 98%: 99% or 100% sequence identity).

Mutants and derivates can be generated using standard techniques of molecular biology as described in details in the section "Nucleic acid molecules" above. Several mutants are described herein. Given the guidance provided in the Examples, and using standard techniques, those skilled in the art can readily generate a wide variety of additional mutants and test whether a biological (e.g., biochemical, spectral, etc.) property has been altered. For example, mutations that reduce oligomerization of a FP can be combined with mutations that improve protein folding and/or alter protein photostability, excitation/emission spectra and/or pH-stability, capability of photoactivation, etc.

For screening of mutant variants, nucleic acids encoding these variants are cloned into suitable expression vector (for example, pQE30 vector, Qiagen) and expressed in host cells (for example, in E. coli XL1 Blue strain, Invitrogen). Depending on the complexity of library, from 100 to 100,000 individual clones each expressing individual FP variant are screened using a fluorescence stereomicroscope equipped with the appropriate filter set (excitation filter 630-680 nm, emission filter 700 nm long-pass). Fluorescence intensity can be also measured using a spectrophotometer at various excitation wavelengths.

Proteins of interest can be also modified using standard techniques that includes RNA-editing, chemical modifications, posttranslational and posttranscriptional modifications and the like. For instance, derivatives of the proteins of interest can be generated by processes such as altered phosphorylation, or glycosylation, or acetylation, or lipidation, or by different types of maturation cleavage and the like.

The proteins of the subject invention are separated from their naturally-occurring environment. For example, purified protein is provided, where "purified" means that the protein is present in a mixture that is substantially free of non-chromogenic or FPs of interest, where "substantially free" means that less than 90%, usually less than 60% and more usually less than 50% of the mixture content is non-chromogenic or FPs or mutants thereof. The proteins of the present invention also may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In some embodiments, the proteins are present in substantially purified form, where by "substantially purified form" means at least 95%, usually at least 97% and more usually at least 99% pure.

The subject proteins and polypeptides may be synthetically produced. For example, wild type proteins may be derived from biological sources which express the proteins. The subject proteins may be derived from synthetic means, e.g. by expressing a recombinant nucleic acid coding sequence encoding the protein of interest in a suitable host, as described above. Any convenient protein purification procedures may be employed, where suitable protein purification methodologies are described in Guide to Protein Purification, M. P. Deutscher, ed., Academic Press, 1990, 894 pp. For example, a lysate may be prepared from the original source and purified using HPLC, exclusion chromatography, gel electrophoresis, affinity chromatography, and the like.

Also provided are fusion proteins comprising a protein of the present invention, fused, for example, to a sequence of subcellular localization (e.g. nuclear localization signal, protein with known subcellular localization, etc.), a signal peptide, or any protein or polypeptide of interest. Fusion proteins may include for example, a FP of the subject invention or mutant thereof and a second polypeptide ("the fusion partner") fused in-frame at the N-terminus C-terminus of the FP and/or as internal fusion. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the FP portion of the fusion protein.

Fusion proteins can be produced using recombinant technologies well known in the art. To generate fusion proteins, a nucleic acid encoding a subject protein is operatively linked with the nucleic acid encoding "fusion partner". In the resulted nucleic acid coding sequence of the FP and coding sequence of the "fusion partner" are covalently linked so that no frameshifts and stop codons are present between these coding sequences.

Transformants

The nucleic acids of the present invention can be used to generate transformants including transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g., *Escherichia coli, Streptomyces* sp., *Bacillus subtilis, Lactobacillus acidophilus*, etc) or eukaryotic host-cells. Transgenic organisms of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e., DNA) into such organisms are widely known and provided in references such as Sambrook et al., Molecular Cloning: A Laboratory Manual, 3rd edition (2001) CSH Press, Cold Spring Harbor, N.Y.

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) CSH Press, Cold Spring Harbor, N.Y.; and Ausubel et al., Current Protocols in Molecular Biology (1995) John Wiley & Sons.

In another embodiment, the transgenic organism can be a fungus, for example yeast. Yeast is widely used as a vehicle for heterologous gene expression (e.g., see Goodey et al., Yeast biotechnology, D R Berry et al., eds, (1987) Allen and Unwin, London, pp 401-429; and King et al., Molecular and Cell Biology of Yeasts, E. F. Walton and G. T. Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2003), Academic Press, San Diego; Gersenstein & Vintersten, Manipulating the Mouse Embryo: A Laboratory Manual, 3rd edition (2002), Nagy A. (Ed), Cold Spring Harbor; Blau et al., Laboratory Animal Medicine, 2nd edition (2002), Fox J. G., Anderson L. C., Loew F. M. & Quimby F. W. (Eds), American Medical Association, American Psychological Association; and Gene Targeting: A Practical Approach. 2nd edition (2000), Alexandra L. Joyner (Ed.) Oxford University Press. For example, transgenic animals can be obtained through homologous recombination, wherein the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see (33).

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Transformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in Plant Biochemistry and Molecular Biology, Lea and Leegood (Eds.), John Wiley & Sons) (1993), pp. 275-295 and in Plant Biotechnology and Transgenic Plants, Oksman-Caldentey and Barz (Eds.), (2002), 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The FPs of the present invention (as well as other components of the subject invention described herein) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

In a preferred embodiment relating to the method for labeling a biological molecule, cell or cell organelle, the subject proteins find use as in vivo labels (or reporter molecules) in cell and molecular biology assays. The assays of interest include but not limited to assays for gene expression, protein localization and co-localization, PPIs, protein-nucleic acid interactions, nucleic acid-nucleic acid interactions, cell and cell organelle localization and interactions, etc. The FPs of the present invention find use as a biomolecule labels, or cell organelle labels in living and fixed cells; as a markers in cell or organelle fusion, as a cell or organelle integrity markers, as a transfection markers (e.g., as labels for selection of transfected cells containing an expression vector encoding at least one FP of the invention), as real-time probes working at near physiological concentrations, etc.

Furthermore, the subject proteins may be used in a method for analyzing gene expression (e.g., promoter activity). In the other words, they find use for identifying and/or measuring the expression of a protein or polypeptide of interest in biological material. This method comprises: i) introducing into a cell a nucleic acid molecule comprising a nucleotide sequence encoding a FP according to the present invention wherein said nucleic acid molecule is operatively linked to and under the control of an expression control sequence which moderates expression of said protein or polypeptide of interest; ii) expression of said nucleic acid under suitable conditions; and iii) detecting the fluorescence emission of the FP as a means of measuring the expression of the protein of interest.

In particular, the subject proteins find use for identifying and/or measuring the expression of protein or polypeptide of interest in the biological material (e.g. host cells). This method comprises: i) introducing into a cell a nucleic acid molecule comprising a nucleotide sequence encoding a FP according to the present invention wherein the nucleic acid molecule is operably linked to and under the control of an expression control sequence which moderates expression of the protein or polypeptide of interest; ii) culturing the cell under conditions suitable for the expression of the protein of interest; and iii) detecting the fluorescence emission of the FP as a means of measuring the expression/localization of the protein of interest.

In particular, the subject proteins find use for identifying and/or localization of protein or polypeptide of interest in biological material. This method comprises: i) introducing into a cell a nucleic acid molecule comprising a nucleotide sequence encoding a FP according to the present invention wherein the nucleic acid molecule is operably linked with sequence encoding protein or polypeptide of interest and under the control of a promoter sequence; ii) culturing the cell under conditions suitable for the expression of the protein of interest; and iii) detecting the fluorescence emission of the FP as a means of measuring the expression/localization of the protein of interest.

The applications of interest include the use of the subject proteins in FRET methods. In these methods, the subject proteins serve as donor and/or acceptors in combination with a second FP or dye, e.g., a FP as described in (34); a mutants of green FP from *Aequorea victoria*, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference; or a monomeric FP provided by this invention (miRFP670nano (SEQ ID NO:1), miRFP670nano3 (SEQ ID NO:2), miRFP704nano (SEQ ID NO:3) and miRFP718nano (SEQ ID NO:4) or circular permutated miRFP670nano (SEQ ID NO:5), circular permutated miRFP670nano3 (SEQ ID NO:6), circular permutated miRFP704nano (SEQ ID NO:7), circular permutated miRFP718nano (SEQ ID NO:8), or other NIR FPs provided by U.S. Pat. No. 10,442,839B2, US20150353609A1 and U.S. Pat. No. 8,653,037B2.

The FPs of the present invention can advantageously be used in FRET experiments. This will produce a far-red or NIR FRET pairs suitable for imaging with the common FRET pairs based on GFP-like proteins and suitable for imaging in vivo. Consequently, the polypeptides of the present invention can be employed in studies, such as e.g. FRET, in which multiple, different FPs are used simultaneously.

Specific examples of the FRET pairs for miRFPnano-related FP are provided in FIGS. 15 and 16. The FRET pair was tested in sensors of protease activity. As one example a sensor for protease activity is provided that is based on the FRET pair between miRFP670nano and miRFP720 disclosed herein (FIG. 15). The two proteins are connected with a linker containing the protease cleavage site. Cleavage at the protease site separates the two proteins and eliminates FRET between them. Thereby the protease activity is detected. In several embodiments the protease site is a caspase-3 protease site, for example, including the amino acid sequence set forth as DEVD. In some examples the protease sensor is a caspase-3 protease sensor. The examples of sensors for detection of Protein Kinase A (PKA) and c-Jun N-terminal kinase (JNK) activities disclosed herein (FIG. 16). These NIR biosensors consisted of a miRFP670nano donor, a phosphoamino acid binding domain, a consensus peptide sequence of kinases substrates, and a miRFP720 acceptor. Phosphorylation of the substrate peptide by activated kinases leads to a conformation rearrangement of the biosensor and an increase of FRET between donor and acceptor. Thereby the kinases activity is detected.

Specific examples of where FRET assays employing the subject FPs may be used include, but are not limited to, the detection of PPIs, such as in a mammalian two-hybrid system, transcription factor dimerization, membrane protein multimerization, multiprotein complex formation; as a biosensor for a number of different events, where a peptide or protein covalently links a FRET fluorescent combination including the subject FPs and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has Ca2+ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The FPs of the present invention can advantageously be used in BRET (bioluminescence resonance energy transfer) experiments with fusion protein comprising (i) consecutive amino acid residues having the sequence set forth in miRFP670nano (SEQ ID NO:1), miRFP670nano3 (SEQ ID NO:2), miRFP704nano (SEQ ID NO:3), miRFP718nano (SEQ ID NO:4), and circular permutated miRFP670nano (SEQ ID NO:5), circular permutated miRFP670nano3 (SEQ ID NO:6), circular permutated miRFP704nano (SEQ ID NO:7), circular permutated miRFP718nano (SEQ ID NO:8). or a protein with 90% or greater identity to one of SEQ ID NOS:1-8, joined at a terminus thereof to Renilla luciferase (RLuc8). Using commercially available Prolum Purple I substrate, which bioluminesces around 400 nm, it is possible to induce bioluminescence resonance energy transfer (BRET) from RLuc8 to miRFPnanos. Indeed, the emission of Rluc supplemented with Prolum Purple I overlaps with the shorter wavelength Soret band absorbance peak of NIR FP containing BV as chromophore. Due to BRET from RLuc8 to miRFPnanos, the resulting NIR bioluminescence of the chimeras has maxima corresponding to the emission maxima of a miRFPnano-related FPs. This constructs can be used as a protein fusion for multimodality in vivo imaging and as a template for development of sensors of various designs, including Ca2+-sensor and monitoring of PPIs. Specific examples of where BRET assays employing the subject FPs may be used include, but are not limited to the specific examples of the FRET assay describes above.

The FPs of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The FPs find also use in a method to compare the activity of two or more expression control sequences in a cell in response to a test substance. Such methods may be performed in the presence and in the absence of a test substance whose effect on the process is to be measured.

The FPs of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular FPs/peptides or as markers alone. Examples of applications involving the automated screening of arrays of cells in which the subject FPs find use include U.S. Pat. No. 5,989,835; as well as WO 0017624; WO 00/26408; WO 00/17643; and WO 00/03246; the disclosures of which are herein incorporated by reference.

The subject proteins can be used as second messenger detectors by fusing the subject proteins to specific domains such as the PKCgamma Ca-binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject FP is used as a label to mark a population of cells and the resulting labeled population of cells is then sorted with a fluorescence activated cell sorting device, as is known in the art. FACS methods are described in U.S. Pat. Nos. 5,968,738 and 5,804,387; the disclosures of which are herein incorporated by reference.

The subject proteins also can be used as in vivo labels in transgenic animals. For example, expression of the subject protein can be driven by tissue-specific promoters, where such methods find use in research for gene therapy, such as testing efficiency of transgenic expression, among other applications. A representative application of FPs in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject FPs also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the FP by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescence activity, because parts of the functional chromophore are divided by the spacer. The spacer is framed by two identical protease-specific cleavage sites. Upon cleavage via the activated protease, the spacer would be cut out and the two residual "subunits" of the FP would be able to reassemble to generate a functional FP. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins.

The subject FPs also can be used as biosensors in prokaryotic and eukaryotic cells, such as a Ca. sup.2+ ion indicator; a pH indicator; a phosphorylation indicator; or as an indicator of other ions, such as magnesium, sodium, potassium, chloride and halides. Methods of using FPs as biosensors also include those described in U.S. Pat. Nos. 5,972,638; 5,824,485 and 5,650,135 (as well as the references cited therein) the disclosures of which are herein incorporated by reference.

The subject FPs also find use as biosensors, insertion modified FPs and biosensors thereof. The biosensors can be used in prokaryotic and eukaryotic cells, such as a Ca2+ ion indicators, a pH indicator, a phosphorylation indicator, other enzyme activity indicators, or as an indicator of ions, such as magnesium, sodium, potassium, chloride, halides, etc. Methods of using FPs as biosensors also include those described in U.S. Pat. Nos. 5,972,638, 5,824,485, and 5,650, 135 (as well as the references cited therein) the disclosures of which are herein incorporated by reference.

The subject FPs also can be used as labels for photoacoustic imaging. Upon provision of the light stimulus, the FPs of the invention are either excited and subsequently emit a fluorescence signal as described above, or they absorb the energy provided by the stimulus, which may be measured by detecting the temperature change associated with this absorption. Detecting the temperature change of the polypeptide or fusion protein upon absorption of the light stimulus is also known in the art under the term "photoacoustic or optoacoustic methods", and is based on absorption of the stimulus, which leads to a local heating and accompanying local expansion. This local expansion leads to ultrasonic pressure waves that can be recorded using high frequency pressure sensors (38-40).

Kits

The present invention also relates to kits for use in practicing one or more of the above-described applications. Kits typically include the protein of the invention as such, or a nucleic acid encoding the same preferably with the elements for expressing the subject proteins, for example, a construct such as a vector comprising a nucleic acid encoding the subject protein. In preferred embodiments kits may be used for monitoring of inflammation, cell cycle, apoptosis within living cells, subcellular structures or protein around. In other embodiments kits may be used for labeling of cells, subcellular structures or proteins.

The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following examples are offered by way of illustration and not by way of limitation.

EXPERIMENTAL DETAILS AND EXAMPLES

Introduction

Bacterial photoreceptors have absorbance spectra in the near-infrared range due to covalently attached heme-derived linear tetrapyrrole compounds and allow engineering NIR FPs (1). Several photoreceptors from a class of bacterial phytochrome photoreceptors (BphPs) were developed into bright monomeric NIR FPs, which efficiently bind endogenous biliverdin (BV) tetrapyrrole in mammalian cells (3-5). However, the BphP-derived NIR FPs minimally require two domains, a PAS and a GAF, to covalently attach a BV chromophore and also possess a complex 'figure-of-eight knot' structure topologically linking the GAF and PAS domains, which affects their folding (1). The only example of a single-domain BphP-based FP, 20-kDa monomeric GAF-FP is dim in mammalian cells (6). Another class of bacterial photoreceptors, allophycocyanins (APCs), was also used to engineer NIR FPs, such as smURFP from TeAPC and several BDFPs from ApcF. Although the APC-based NIR FPs are smaller, they have low efficiency of BV binding, resulting in significantly lower brightness in mammalian cells than the BphP-derived NIR FPs(7-9).

To overcome the drawbacks of the BphP- and APC-based NIR FPs, we turned our attention to a class of cyanobacteriochrome (CBCR) photoreceptors found in cyanobacteria (10). Typical CBCRs consist of one or more GAF domains and effector domains (1, 10). GAF domains of CBCRs have several unique properties to consider them for engineering of NIR FPs. First, a single CBCR GAF domain is sufficient for autocatalytic binding of tetrapyrrole chromophore (11), potentially allowing to engineer single-domain FPs, twice smaller than BphP-derived FPs. This binding occurs via a conserved Cys residue located in the GAF domain, in contrast to the Cys in the PAS domain in BphPs. Second, GAF domains of CBCRs are naturally monomeric (12, 13), unlike typically dimeric BphPs and oligomeric APCs (1). Third, in contrast to BphPs and APCs, various CBCR subclasses exhibit a large spectral diversity and, moreover, a variety of photocycles in which GAF domains reversibly photoconvert between UV/blue, blue/green, green/red and red/NIR absorbing forms (14, 15). Fourth, CBCR GAF domains are also found as components of complex signaling proteins (16), suggesting that their structural fold is naturally optimized to use in fusion constructs (15).

Despite these advantages, CBCRs utilize phycocyanobilin (PCB) tetrapyrrole as a chromophore. PCB is naturally present in plant and cyanobacteria but not in mammalian cells, which produce BV (3, 17, 18). Recently, however, three CBCR GAF domains from *Acaryochloris marina* were shown to bind both PCB and BV (20-22). Moreover, GAF domains in BphP-derived NIR FPs were adopted to covalently bind BV(41). Based on these findings, we hypothesized that CBCRs can be engineered into BV-binding NIR FPs.

Here a set of bright spectrally distinct monomeric CBCR-derived NIR FPs termed miRFP670nano, miRFP670nano3, miRFP704nano, miRFP718nano, which fully rely on endogenous BV to fluoresce in mammalian cells and mammals, are disclosed. We disclose the use of these miRFPnanos in a wide range of NIR protein tags, reporters and biosensors.

Characterization of the developed NIR FPs showed itheir numerous advantages over NIR FPs developed from other photoreceptors, including monomeric state, substantially smaller size, significantly higher protein stability in vitro and in mammalian cells, and possibility to be inserted inside of tagged proteins.

Results

Engineering of the CBCR GAF domain into BV-binding FP. To choose a template for engineering of BV-binding CBCR-based NIR FP, we evaluated GAF domains from ten different CBCRs (FIG. 1a). To facilitate protein production in mammalian cells, we first codon-optimized the CBCR genes for mammalian cell expression. To facilitate BV binding, we then introduced Leu residues at the position corresponding to Leu337 in AM1_1557g2, which was shown being important for the BV attachment (20, 22). To reduce size of the CBCR GAF domains, we next removed the N-terminal al helix, which does not participate in the formation of the tetrapyrrole-binding pocket (42).

Figures 2A, 2O:
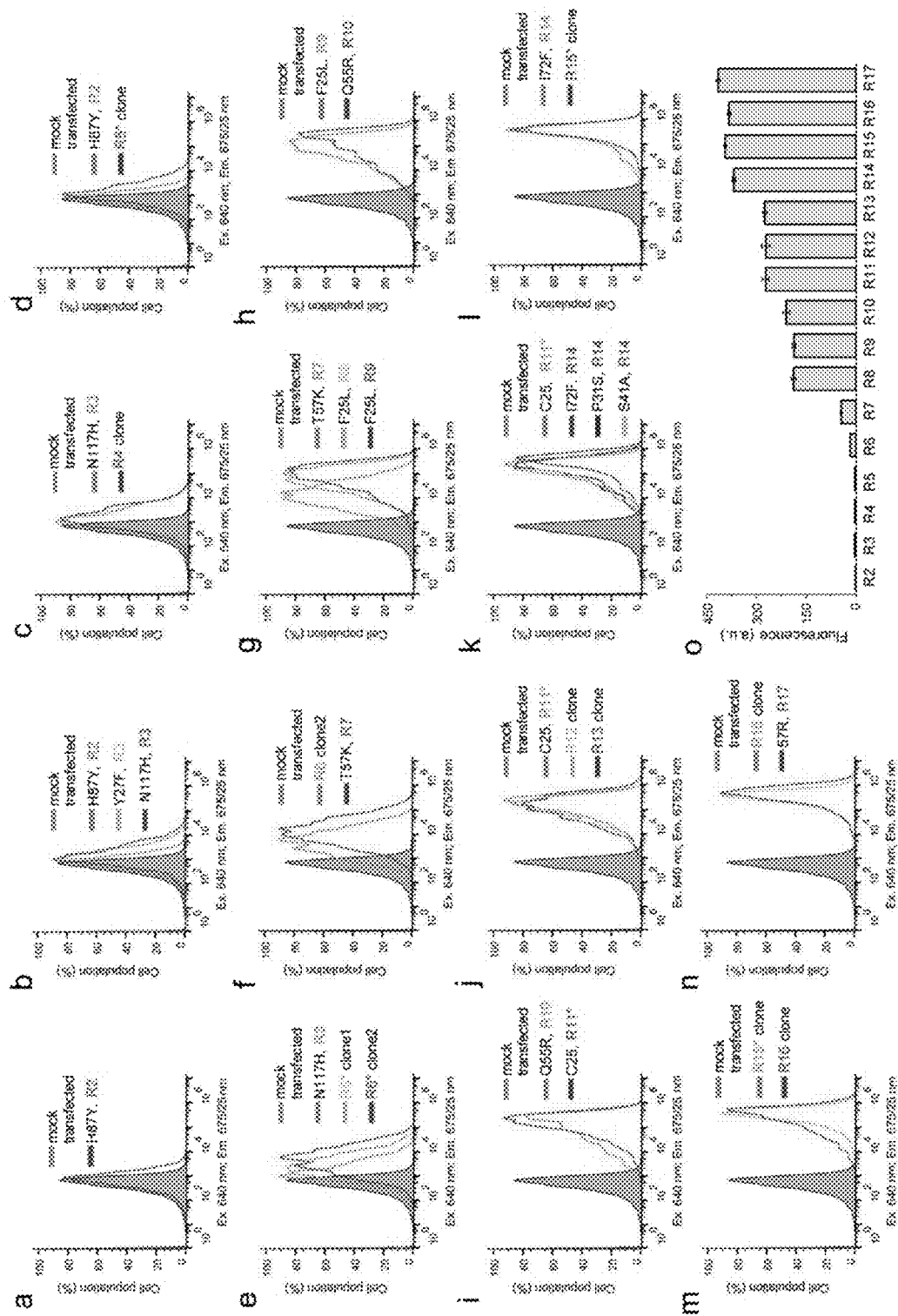
FIG. 2(a)-2(o). Molecular engineering of miRFP670nano. (a-n) Comparison of clones selected on each round of selection in HeLa cells. The main mutations are indicated. (o) Quantification of the data represented in a-n. Mean NIR fluorescence intensity was normalized to mean green fluorescence intensity of co-expressed EGFP and to mean fluorescence intensity of mock-transfected cells. Error bars, s.d. (n=3; transfection experiments)

These CBCRs were co-expressed in *E. coli* with heme oxygenase for BV production, however, exhibited very weak or no fluorescence. Interestingly, a NpR3784 GAF domain substantially outperformed the GAF domains of other CBCRs, including AM1_1557g2 and AM1_1870g3 that earlier were shown to bind BV (FIG. 1b,c). We subjected the NpR3784 GAF domain to several rounds of random mutagenesis, followed by saturating mutagenesis of the identified residues. After each round, we tested the best clones in mammalian cells and selected for the next molecular evolution only those, which exhibited the high fluorescence brightness in both bacteria and mammalian cells (FIG. 2). Totally, 17 rounds of the directed molecular evolution resulted in a NIR FP variant, termed miRFP670nano, consisting of 147 amino acid residues (17 kDa) and bearing 18 substitutions (numbering follows that for miRFP670nano sequence) relative to wild-type GAF from NpR3784: V7M, F25C, M26V, Y27F, P31E, S41A, A48S, N51K, Q55R, T57R, I72Y, G82N, H87Y, N99I, N117H, C119L, L136Q, and Q139V.

Figures 3A, 3B:
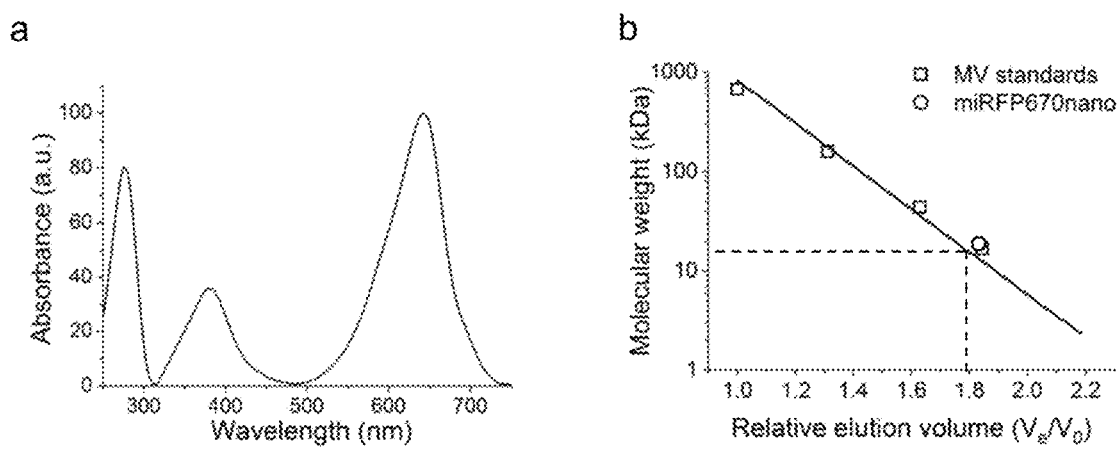
FIG. 3(a)-3(b). Biochemical and photochemical properties of miRFP670nano. (a) Absorbance spectrum of miRFP670nano (apoprotein $A^{01\%}_{280}$ value=1.79 AU). (b) Size exclusion chromatography calibration plot. $V_e$, elution volume; $V_o$, void volume of column.
Figures 4A, 4B, 4C, 4D, 4E, 4F, 4G, 4H, 4I:
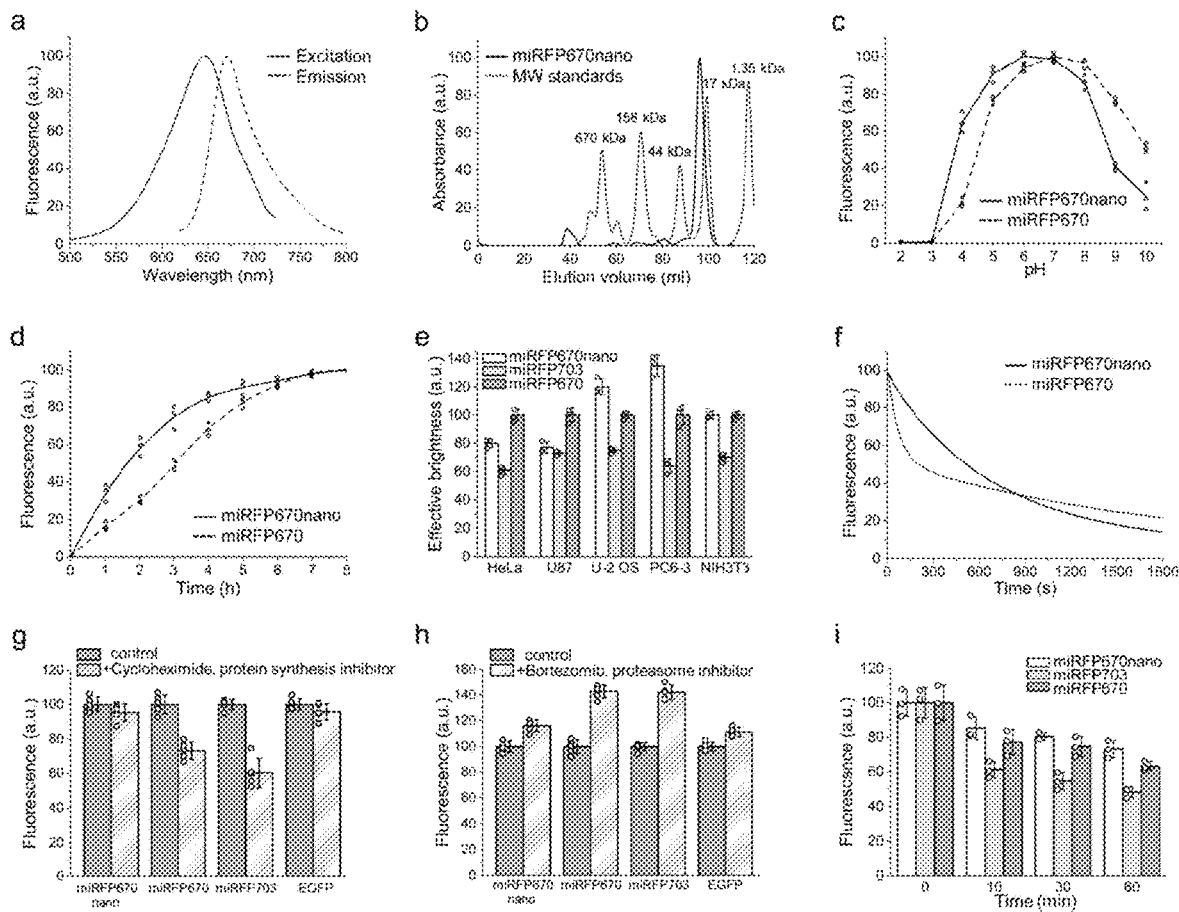
FIG. 4(a)-4(i). Characterization of miRFP670nano. (a) Fluorescence excitation and emission spectra of miRFP670nano. (b) Size-exclusion chromatography of miRFP670nano at concentration 10 mg ml$^{-1}$ and indicated molecular weight standards. miRFP670nano with polyhistidine tag and linker runs as a monomer with the apparent molecular weight of 18.8 kDa. (c) pH dependencies of NIR fluorescence for miRFP670nano and miRFP670. (d) Kinetics of miRFP670nano and miRFP670 maturation. Time "0" corresponds to the beginning of the 1-h-long pulse-chase induction of the protein expression in bacteria. (e) Effective (cellular) brightness of miRFP670nano, miRFP703, and miRFP670 in mammalian cells. Live HeLa, U87, U-2 OS, PC6-3, and NIH3T3 cells were transiently transfected with miRFP670nano, miRFP703, or miRFP670. Fluorescence was analyzed by flow cytometry 72 h after transfection. NIR fluorescence intensity was normalized to that of co-transfected EGFP (to account for differences in transfection efficiency), to excitation efficiency of each NIR FP by 640 nm laser, and to emission spectrum of each FP in the emission filter. Effective brightness of miRFP670 was assumed to 100% for each cell line. Error bars, s.d. (n=3; transfection experiments). (f) Photobleaching of miRFP670nano and miRFP670 in live HeLa cells. (g) Mean fluorescence intensity of HeLa cells transiently transfected with miRFP670nano, miRFP703, miRFP670, and EGFP before and after 4 h of incubation with 20 μg ml$^{-1}$ cycloheximide. Error bars, s.d. (n=5; transfection experiments). (h) Mean fluorescence intensity of HeLa cells transiently transfected with miRFP670nano, miRFP703, miRFP670, and EGFP before and after 4 h of incubation with 10 μM bortezomib. Error bars, s.d. (n=5; transfection experiments). (i) Tolerance of miRFP670nano to fixation in paraformaldehyde. HeLa cells transfected with miRFP670nano, miRFP670, and miRFP703 were incubated with 4% paraformaldehyde for 10-60 min. The fluorescence of cells treated with paraformaldehyde was normalized to fluorescence of non-fixed cells. Error bars, s.d. (n=3; transfection experiments).
Figure 5:
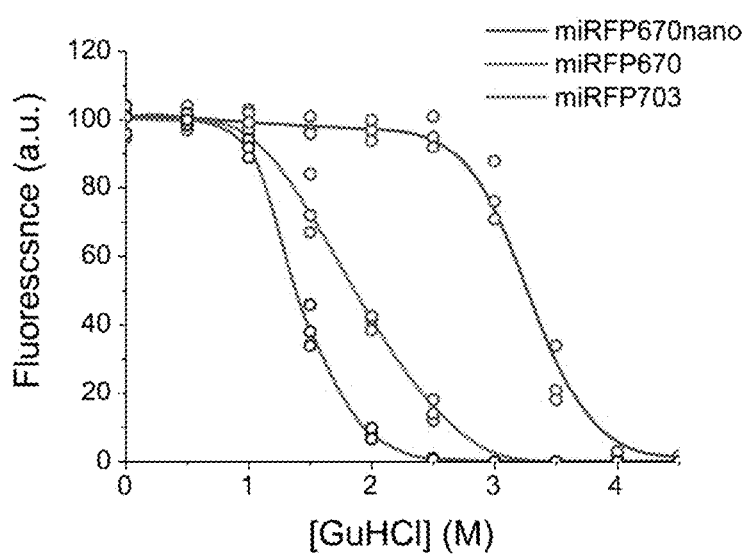
FIG. 5. Comparison of NIR FPs stabilities to denaturation condition. The fluorescence of NIR FPs after 24 h of incubation at different denaturant guanidine hydrochloride (GuHCl) concentrations. The data were normalized to the fluorescence of NIR FPs in buffered solution (n=3; transfection experiments). Calculated concentrations of guanidine hydrochloride, in which 50% fluorescence is retained, are 3.3 M for miRFP670nano, 1.85 M for miRFP670 and 1.4 M for miRFP703.

Characterization of miRFP670nano protein in vitro. Absorbance of miRFP670nano had a minor peak at 390 nm corresponding to the Soret band, characteristic for tetrapyrrole-binding proteins, and a major peak at 645 nm, suggestive of the efficient BV incorporation (FIG. 3a). miRFP670nano exhibited fluorescence excitation and emission maxima at 645 nm and 670 nm, respectively, which were close to those observed for blue-shifted two-domain BphP-based NIR FPs, like miRFP670 (FIG. 4a). miRFP670nano exhibited monomeric behavior in size exclusion chromatography at high concentration of 10 mg ml$^{-1}$ (FIG. 3b and FIG. 4b). Notably, with fluorescence quantum yield of 10.8% and extinction coefficient of 95,000 $M^{-1}cm^{-1}$ molecular brightness (a product of molar extinction coefficient and quantum yield) of miRFP670nano exceeded that of the most of BphP-based NIR FPs.

miRFP670nano had substantially higher protein stability than BphP-based NIR FPs. Studies of a pH dependence revealed that miRFP670nano fluorescence is stable between pH 4.0 and 8.0, with pk=3.7, which was notably acid-shifted than for BphP-derived NIR FPs, having $pK_a$=4.5 (FIG. 4c). Moreover, after 24 h incubation in 3.0 M guanidine hydrochloride miRFP670nano retained ~80% of its fluorescence, whereas miRFP670 and miRFP703 were stable up to 1.5 M guanidine hydrochloride concentration only (FIG. 5). Likely, the compact and tight structure enhanced the miRFP670nano resistance to denaturating conditions.

miRFP670nano maturation had a half-time of ~100 min (FIG. 4d), which was 1.8-fold faster than for spectrally similar two-domain miRFP670, suggesting that the single-domain structure and the absence of the characteristic for all BphP-based NIR FPs figure-of-eight knot structure accelerated the miRFP670nano folding.

Performance of miRFP670nano in mammalian cells. miRFP670nano efficiently binds endogenous BV in mammalian cells. The cellular (a.k.a. effective) brightness of miRFP670nano was comparable to that to miRFP670 and exceeded that of miRFP703 in all tested mammalian cells (FIG. 4e). The high effective brightness in the absence of exogenous BV in mammalian cells is an essential advantage of BphP-based NIR FPs over APC-derived FPs (3, 9). While BV is the major chromophore for BphPs, it is not the case for CBCRs for which PCB is the primary tetrapyrrole co-factor, emphasizing the efficiency of the applied molecular evolution resulted in miRFP670nano.

Figure 6:
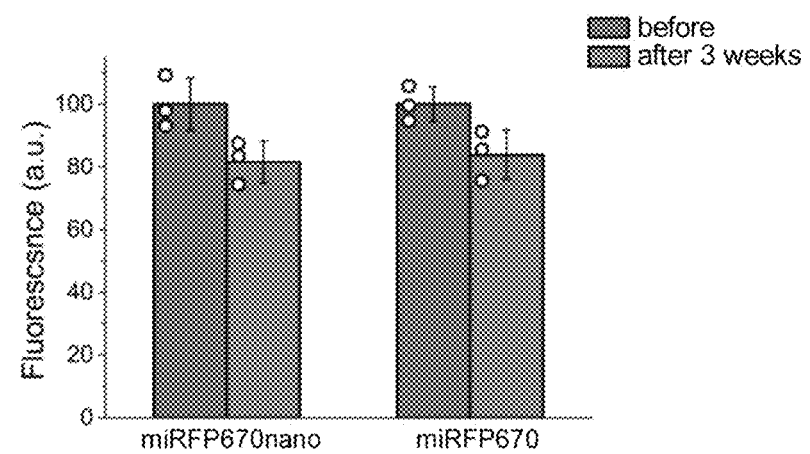
FIG. 6. Cytotoxicity assay. Mean fluorescence intensities of live HeLa cells stably expressing miRFP670nano and miRFP670 were analyzed by flow cytometry on day 14 (red) and day 35 (green) after transfection. Error bars, s.d (n=3 independent experiments).
Figure 7:
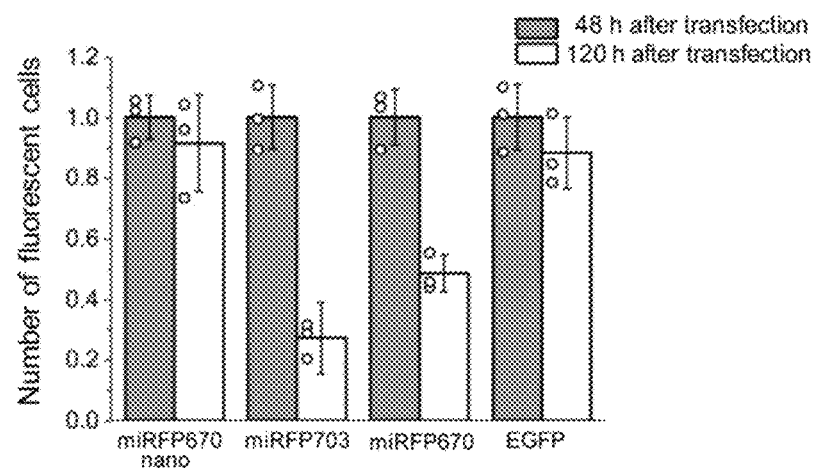
FIG. 7. Stability of miRFP670nano in transiently transfected HeLa cells. The number of FP expressing (fluorescent) HeLa cells transiently transfected with miRFP670nano, miRFP703, miRFP670 and EGFP was calculated 48 h and 120 h after transfection. The values were normalized to the percentage observed 48 h after transfection. Error bars, s.d. (n=3 transfection experiments).

In mammalian cells miRFP670nano exhibited 2.8-fold higher photostability than miRFP670 (FIG. 4f.). miRFP670nano also exhibited low cytotoxicity (FIG. 6). The high photostability, low cytotoxicity and high effective brightness make miRFP670nano a favorable NIR FP for imaging of long-term cellular events.

miRFP670nano is highly stable in mammalian cells. Protein degradation analysis showed that after 4 h incubation with a protein synthesis inhibitor cycloheximide miRFP670nano-expressing cells retained ~95% of their fluorescence (FIG. 4g). Similar cellular stability was observed for EGFP. In contrast, cells expressing miRFP670 or miRFP703 retained only ~70% and 60% of fluorescence, respectively. Furthermore, incubation with bortezomib, an inhibitor of proteasome-dependent protein degradation, just slightly increased brightness of the miRFP670nano- and EGFP-expressing cells (16% and 11%, respectively) (FIG. 4h). Contrary, the cellular brightness of BphP-based FPs was increased more than 40% after inhibition of proteosomal degradation. Moreover, a comparison of the number of fluorescent cells 48 h and 120 h after transfection for all these FPs confirmed the high miRFP670nano cellular stability (FIG. 7). While overall number of miRFP670- and miRFP703-expressing cells decreased more than twice 120 h after transfection, the number of miRFP670nano-expressing cells decreased ~10% only, which was similar to those with EGFP.

Live-cell imaging allows monitoring of dynamic events but some studies require cell fixation. We compared tolerance of miRFP670nano and BphP-based miRFP670 and miRFP703 to fixation with 4% paraformaldehyde. Again, the miRFP670nano-transfected cells demonstrated the highest stability and retained more than 80% of fluorescence after 30 min fixation (FIG. 4i). Overall, likely due to the compact and robust protein fold CBCR-derived miRFP670nano exhibits the high cellular brightness and significantly enhanced protein stability in vitro and in mammalian cells.

Figures 8A, 8B, 8C, 8D, 8E, 8F, 8G, 8H, 8I, 8J, 8K, 8L, 8M:
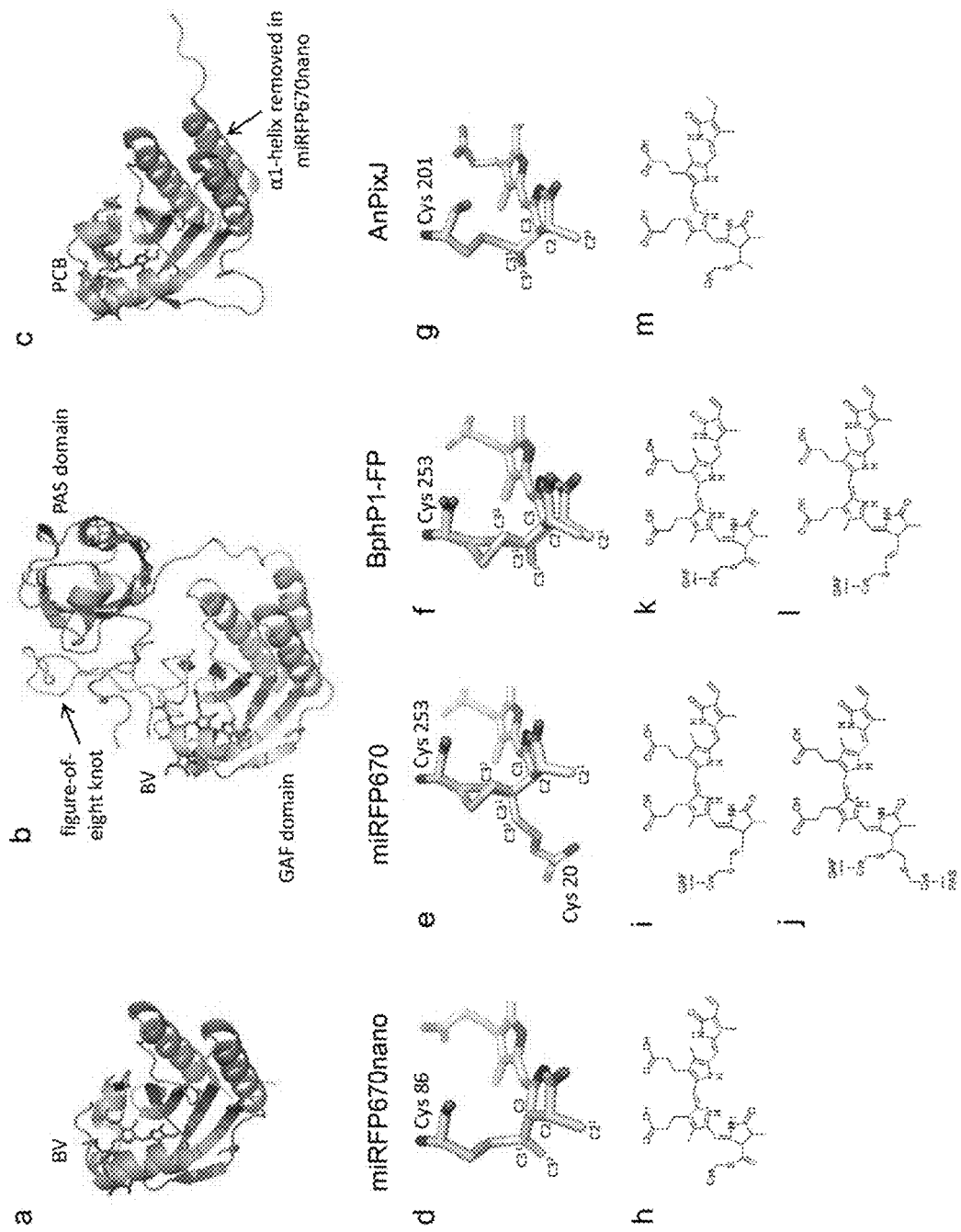
FIG. 8(a)-8(m). Comparison of miRFP670nano, miRFP670, BphP1-FP, and AnPixJ structures and chromophores. a-c Overall structures of (a) miRFP670nano, (b) miRFP670 (PDB ID: 5VIV), BphP1-FP (PDB ID: 4XTQ), and (c) AnPixJ (PDB ID: 3W2Z). The BV and PCB chromophores are in magenta. α1-Helix removed in miRFP670nano is indicated in AnPixJ structure. The PAS and GAF domains of miRFP670 are in cyan and yellow, respectively, and the figure-of-eight knot is indicated. Because of the very similar structures of miRFP670 and BphP1-FP, only the former one is shown. d-g Chromophores (rings A and B only) bound to Cys residues in (d) miRFP670nano, (e) miRFP670, (f) BphP1-FP, and (g) AnPixJ. Carbon, nitrogen, oxygen, and sulfur atoms are in white, blue, red, and yellow, respectively. Single chromophore species are observed in miRFP670nano and AnPixJ only. Two BV chromophore species are observed in miRFP670 and BphP1-FP. h-m Chemical formulas of the chromophores in (h) miRFP670nano, (i), (j) miRFP670, (k), (l) BphP1-FP, and (m) AnPixJ. In miRFP670nano, the BV chromophore (h) is bound to the Cys86 residue via the C3$^1$ atom. In miRFP670 the BV chromophore (i) is bound via the C3$^2$ atom to the Cys253 in the GAF domain, and the BV chromophore (j) is bound via the C3$^1$ atom to Cys253 in the GAF domain and also via the C3$^2$ atom to Cys20 in the PAS domain. In BphP1-FP the BV chromophore (k) is bound via the $C3^1$ atom to Cys253 in the GAF domain, and the BV chromophore (1) is bound via the $C3^2$ atom to Cys253 residue in the GAF domain. In AnPixJ the PCB chromophore (m) is bound to the Cys201 residues via the $C3^1$ atom FIG. 9(a)-9(e). miRFP670nano protein structure and its chromophore environment. (a) Overall structure of miRFP670nano. (b) The chromophore bound to Cys 86 in 2Fo-Fc electron density map countered at 1.0 σ. (c) Hydrogen bond network around the chromophore. (d) Stacking interactions between the chromophore and surrounding residues. BV adduct forms one parallel and one T-shaped stacking interaction with Y87 and F59, respectively. (e) Amino acid difference between miRFP670nano and parental CBCR NpR3784g. Residues that are different in miRFP670nano and NpR3784g are shown as sticks (both green and magenta). Residues that had the most impact on miRFP670nano spectral properties are shown in magenta.
Figures 9A, 9B, 9C, 9D, 9E:
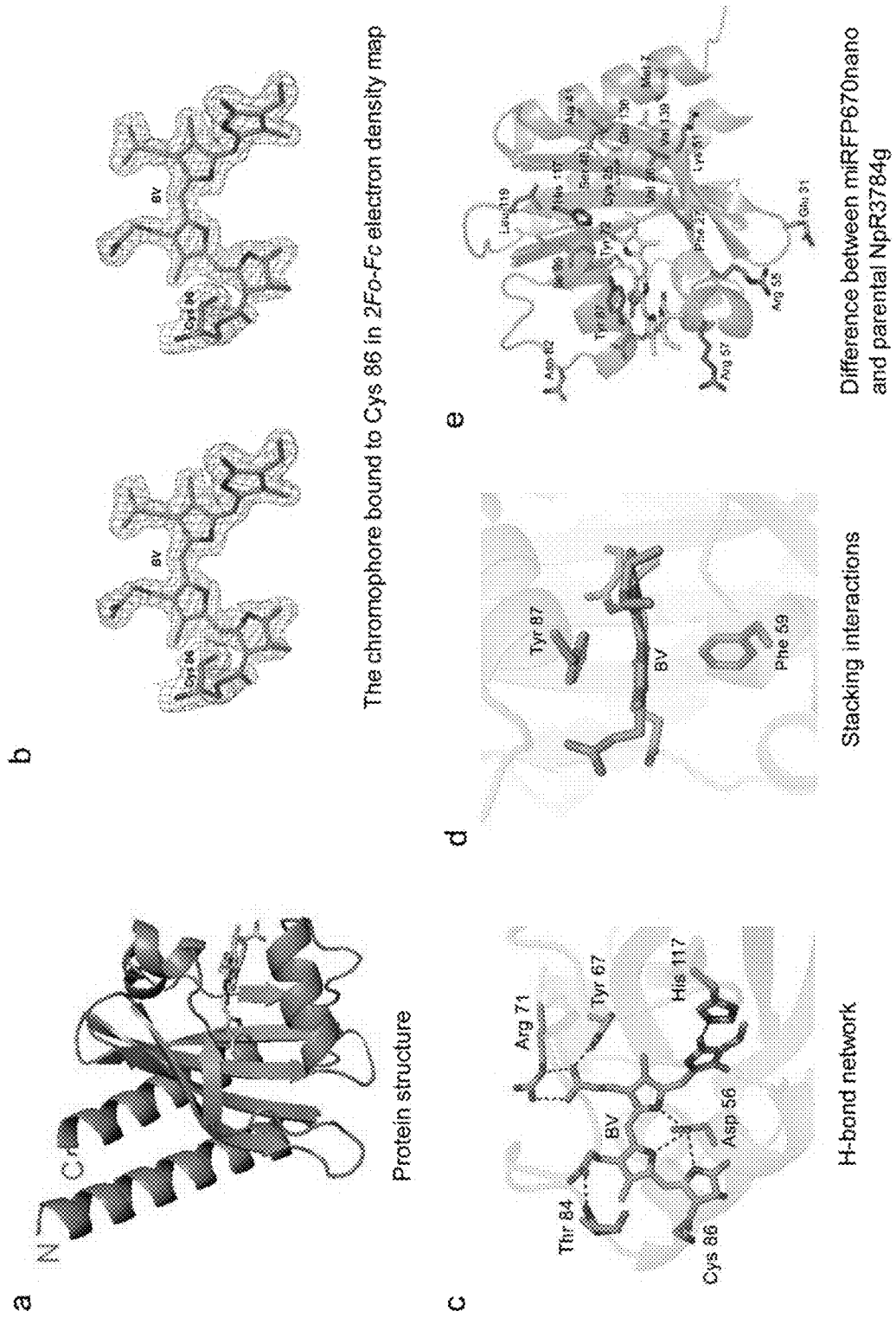

Structural basis of miRFP670nano properties. To reveal the structural basis of the protein stability, brightness and specificity to BV chromophore, we determined the crystal structure of miRFP670nano at 1.95 Å resolution (FIG. 8 and FIG. 9). miRFP670nano adopts a GAF-domain fold, but with the N- and C-termini located in the spatial proximity (FIG. 8a and FIG. 9a). The GAF domain of BphPs has the similar fold, however, it is topologically linked to the adjacent PAS domain via a loop in the figure-of-eight knot (FIG. 8b). The closest available structure of the GAF domain of CBCR is a structure of putative phototaxis regulator PixJs of *Anabaena* sp. PCC 7120, AnPixJ, in the red-absorbing state (42) (FIG. 8c).

BV is covalently attached by a thioether bond between the conserved for CBCRs Cys86 residue and the $C3^1$ atom of the ring A (FIG. 8d,h and FIG. 9b), similar to the native CBCR's PCB chromophore (FIG. 8g,m), but having a double bond between $C3^1=C3^2$. This mode of the BV binding is different than in natural BphPs and red-shifted BphP-derived NIR FPs in which BV is attached via the $C3^2$ atom of the ring A to a conserved Cys in the PAS domain. Recently, however, the unusual covalent binding of BV to Cys in the GAF domain was described for blue-shifted NIR FPs, such as miRFP670 and BphP1-FP, containing the engineered Cys residue in the GAF domain (41, 43, 44). While only one BV chromophore type is detected in the crystal structure of miRFP670nano (FIG. 8d), the blue-shifted BphP-based NIR FPs have two different chromophore types (41, 43) (FIG. 8e,f), resulting in two distinct protein species present in miRFP670, as well as in BphP1-FP. miRFP670nano chromophore has the same number of conjugated double bonds as the chromophores in blue-shifted BphP-based NIR FPs (FIG. 8h-l) that explains the similarity of spectra for these three NIR FPs (41).

Immediate chromophore environment is critical for BV binding and fluorescence of miRFP670nano. In the chromophore-binding pocket, BV is stabilized by eight hydrogen bonds with D56, Y67, T84, R71, and H117, π-π stacking with Y87, and T-stacking with F59 (FIG. 9c,d). A pyrrole water, a proton donor providing excited-state proton transfer (ESPT) in BphP-derived NIR FPs and natural BphPs, is absent in miRFP670nano, similar to CBCR AnPixJ (42). Its role is likely played by the side chain of D56, which forms H-bonds with pyrrole nitrogens of the rings A, B and C (42).

Of the 18 amino acid substitutions introduced into parental NpR3784g (FIG. 9e), F25C, Y27F, H87Y, N99I, and N117H are located within 3.6 Å of the chromophore and either directly stabilize it or provide for it favorable accommodation. One of the important substitutions, N117H makes a strong H-bond with the ring D, which is absent in NpR3784g, thus preventing rotation of this ring and non-radiative energy dissipation via photoswitching. Another critical mutation is H87Y, which introduced a perfect parallel π-π stacking with BV. F25C makes additional space in the chromophore-binding pocket, possibly enhancing BV accommodation. T57R substitution introduced a flexible positively charged residue near the chromophore binding site, enabling electrostatic attraction of BV and its additional shielding from solvent. Substitutions Y27F and N99I increased the hydrophobicity of the chromophore environment.

Such a favorable chromophore binding pocket within a compact single GAF-domain fold should make miRFP670nano a robust probe for various applications.

To develop spectrally distinct FPs, we analyzed miRFP670nano structure and applied the rational design strategy. By introducing mutations R57C and C86S we obtained FP with excitation/emission at 680 nm/704 nm. By introducing two additional mutations L90F and V115S we obtained more NIR-shifted FP with excitation/emission at 690 nm/718 nm. To improve FPs brightness, we next subjected them to additional rounds of random mutagenesis. We also performed saturating mutagenesis of the identified residues in miRFP670nano and both red-shifted FPs. After each round, we tested the best clones in mammalian cells and selected for the next molecular evolution only those, which exhibited the high fluorescence brightness in both bacteria and mammalian cells (FIG. 10).

Figures 11A, 11B, 11C, 11D:
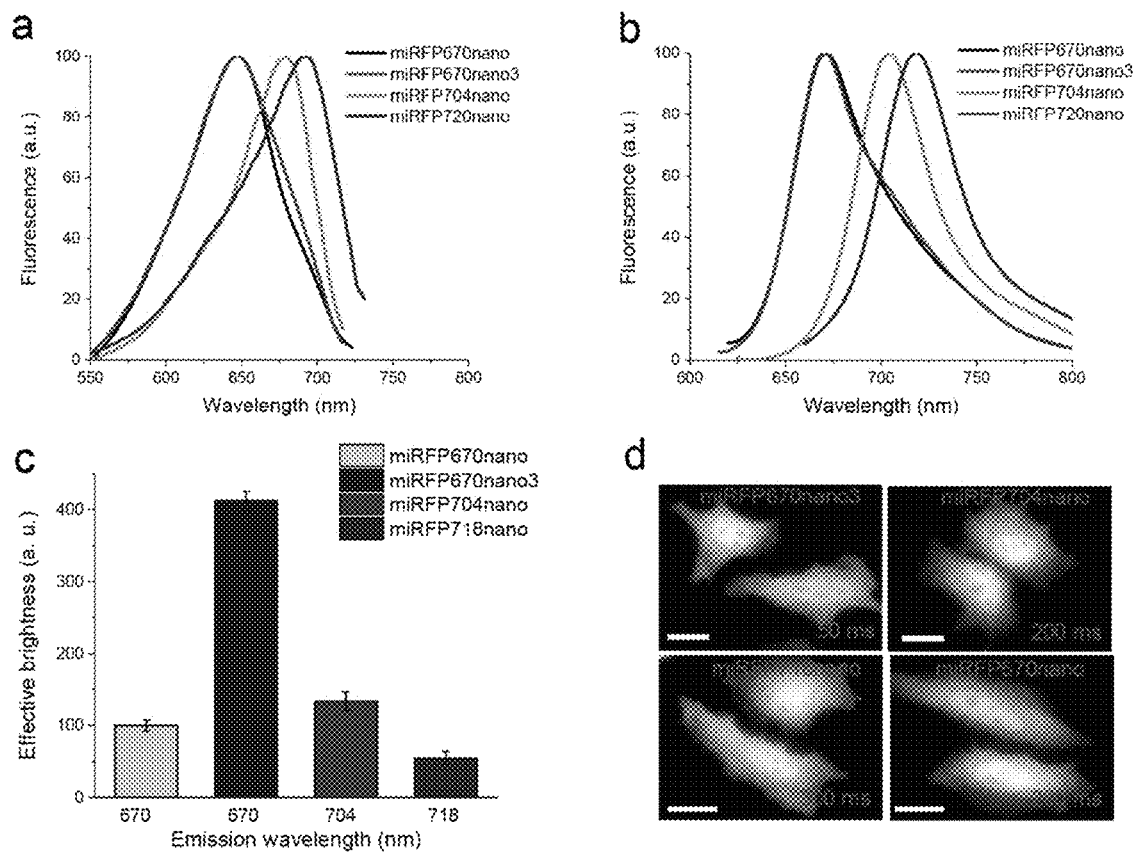
FIG. 11(a)-11(d). Characterization of miRFPnanos. (a) Fluorescence excitation spectra of engineered miRFP670nano, miRFP670nano3, miRFP704nano and miRFP718nano. (b) Fluorescence emission spectra of miRFPnano, miRFP670nano3, miRFP704nano and miRFP718nano. (c) Brightness of live HeLa cells transiently transfected with CBCR-based NIR FPs analyzed by flow cytometry. The NIR fluorescence intensity was normalized to transfection efficiency (fluorescence of co-transfected EGFP), to excitation efficiency of each FP with 640 nm laser, and to fluorescence signal of each FP in the emission filter. The NIR effective brightness of miRFP670nano was assumed to 100%. Error bars, s.d. (n=3; transfection experiments). (d) Representative fluorescence images of miRFPnanos in live HeLa cells. Scale bar, 10 µm.

As a result, we have obtained miRFP670nano3 (excitation/emission at 645 nm/670 nm) miRFP704nano (excitation/emission at 680 nm/704 nm) and miRFP718nano (excitation/emission at 690 nm/718 nm) (FIG. 11a,b and Table 1). All miRFPnanos brightly fluoresce in mammalian cells without supplementation of exogenous BV chromophore (FIG. 11c). Importantly, miRFP670nano3, having the same spectral properties, showed 4.1-fold increased brightness compared to miRFP670nano (FIG. 11c and Table 1). Cell images indicate homogenous distribution of miRFPnanos (FIG. 11d).

TABLE 1

Selected NIR FPs engineered from various bacterial photoreceptors.

| NIR FP | Parental bacterial photoreceptor | Ex, nm | Em, nm | Extinction coefficient, $M^{-1}cm^{-1}$ | Quantum yield, % | Oligomoic state | Photostability in HeLa cells, $t_{1/2}$, s | Brightness in mammalian cells vs. miRFP670-nano, %[a] | Ref. |
|---|---|---|---|---|---|---|---|---|---|
| miRFP670nano | NpR3784 CBCR | 645 | 670 | 95,000 | 10.8 | monomer | 505 | 100[b] | (45) |
| miRFP670nano3 | | 645 | 670 | 129,000 | 18.5 | monomer | 473 | 412 | here |
| miRFP704nano | | 680 | 704 | 93,000 | 9.9 | monomer | 4421 | 134 | here |
| miRFP718nano | | 690 | 718 | 79,000 | 5.6 | monomer | 920 | 55 | here |
| smURFP | TeAPCα APC | 642 | 670 | 180,000[b] | 18.0 | dimer | 570 | 1 | (7, 9) |
| BDFP1.5 | ApcF APC | 688 | 711 | 74,000 | 5.0 | monomer | 1310[c] | 0.5[c] | (8) |

[a]Unless otherwise stated, it is determined as effective NIR fluorescence in live HeLa cells 72 h after transfection with no supply of exogenous BV and after normalization to fluorescence of co-transfected EGFP.
[b]Determined for a dimer of smURFP molecules.
[c]Based on the comparison with smURFP in HEK293 cells in (8).

Figures 12A, 12B, 12C:
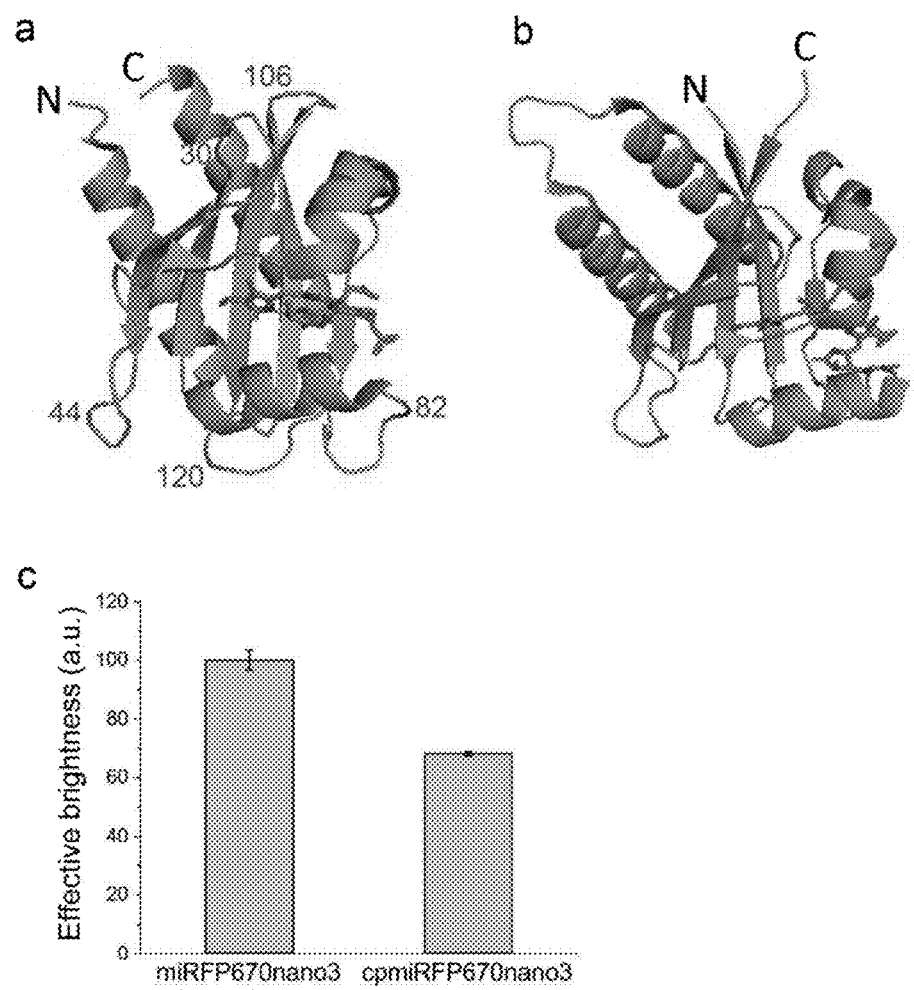
FIG. 12(a)-12(c). Development of circularly permutated mutants of miRFPnanos. (a) Positions selected for miRFPnano permutations (highlighted in red). (b) Structure of cpmiRFPnano, permutated at position 106. (c) Mean fluorescence intensities of live HeLa cells expressing miRFP670nano3 and cpmiRFPnano3 (miRFP670nano3 permutated at position Q106) analyzed by flow cytometry. Error bars, s.d (n=3 independent experiments).

By analysis of protein structure we next identified a sites that could be tolerate for circular permutations (FIG. 12a). We constructed mutants circularly permuted by positions 30, 44, 82, 106 and 120. We found that variants circularly permuted by position 106 displayed high brightness in mammalian cells without exogenous BV and retains 70% brightness of miRFP670nanos (FIG. 12b,c).

Figures 13A, 13Q:
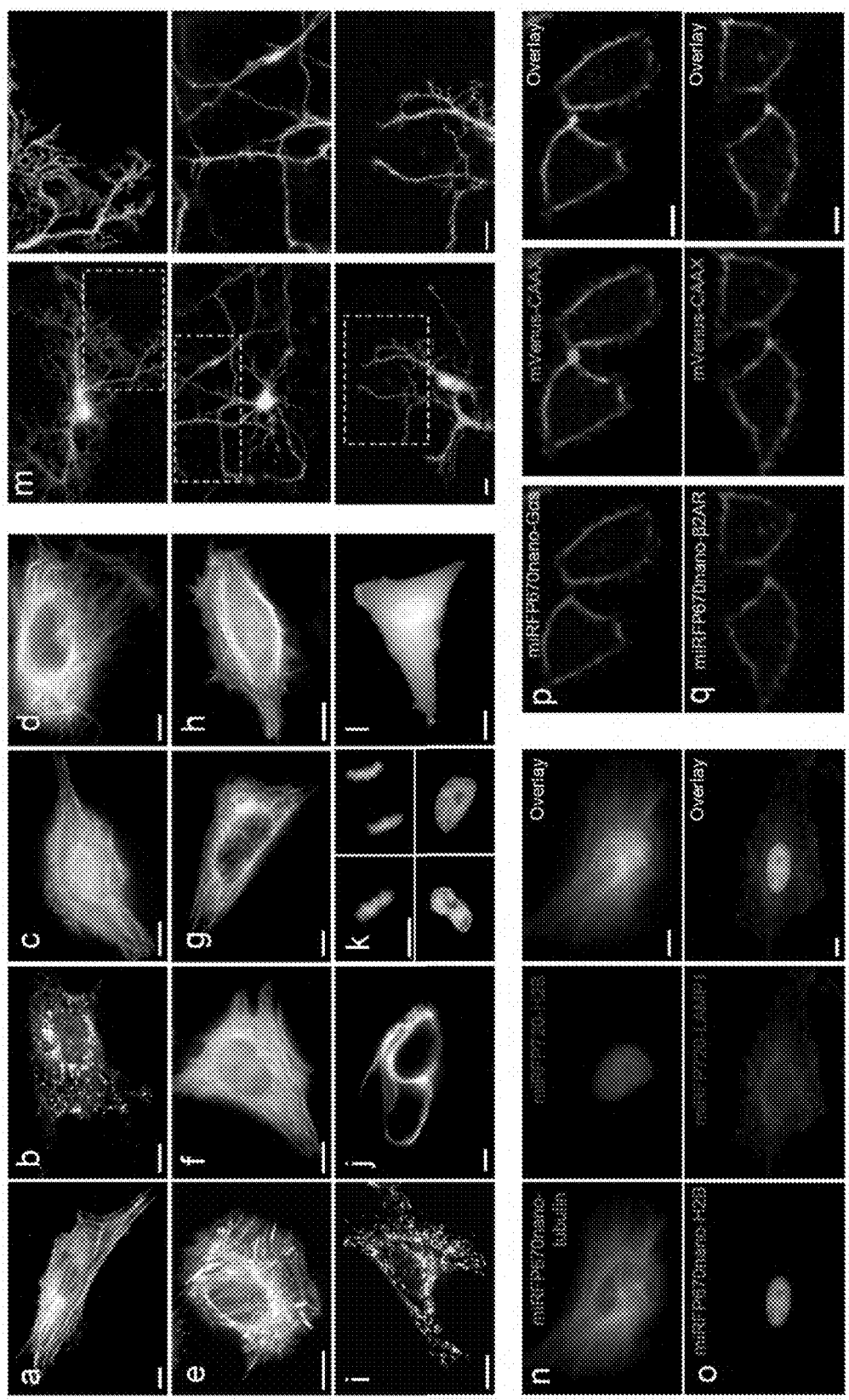
FIG. 13(a)-13(q). miRFP670nano fusions imaged using epifluorescence microscopy. Live HeLa cells transfected with the miRFP670nano N- and C-terminal fusion constructs. The C-terminal fusions are (a) actin; (b) vesicular protein clathrin; (c) myosin; (d) α-tubulin. The N-terminal fusions are (e) α-actinin; (f) microtubules-binding EB3; (g) keratin; (h) actin-binding LifeAct; (i) lysosomal membrane glycoprotein LAMP1; (j) vimentin; (k) histone H2B. (l) Cells expressing untagged miRFP670nano. (m) Dissociated rat cortical neurons transfected with miRFP670nano encoding plasmid at 3 days in vitro (DIV 3). Neurons were imaged 48 h after transfection. Left images are zoom-in of the indicated areas of the right images. (n) Two-color images of cells co-expressing α-tubulin tagged with miRFP670nano and H2B tagged with miRFP720. (o) Two-color images of cells co-expressing LAMP1 tagged with miRFP720 and H2B tagged with miRFP670nano. (p) miRFP670nano internally inserted between the helical and GTPase domains of the G-protein α subunit (Gαs). (q) miRFP670nano internally inserted into the intracellular loop 3 of the β2 adrenergic receptor (β2AR). mVenus with membrane targeting CAAX motif was used for membrane visualization. Scale bars, 10 µm.

Performance of miRFPnanos as protein fusion tag. To test performance of miRFPnanos as protein tags, we expressed several miRFPnano fusions in mammalian cells. In live mammalian cells these fusions exhibited proper localization, including the fusions associated with or forming filaments (FIG. 13). miRFPnano fusion with histone 2B localized properly in different phases of mitosis and did not affect cell division (FIG. 13k). Cell images showed homogenous distribution of miRFP670nano and absence of intracellular aggregates (FIG. 13l).

In number of cases, placing of a FP tag at the termini of proteins affects their function or leads to incorrect localization (46). Such proteins can be labeled with FP inserted in a middle of the sequence as an internal tag. For this, FP should have good folding properties and its N- and C-termini located close to each other, like in miRFP670nano (FIG. 8a and FIG. 9a).

To evaluate miRFPnanos as an internal tag, we constructed internally labelled G protein α-subunit ($G\alpha_s$) and β2-adrenergic receptor (β2AR) in which miRFP670nano or miRFP670 were inserted between the helical and GTPase domains of $G\alpha_s$ and into intracellular loop 3 of β2AR (47, 48). Both miRFP670nano internal fusions demonstrated perfect membrane localization, co-localizing with mVenus containing a CAAX-motif for membrane targeting. In contrast, the internal fusion constructs with two-domain miRFP670 did not exhibit membrane localization and formed aggregates (FIG. 13p,q and FIG. 14a-d). Most likely the complex structural organization of BphP-derived miRFP670 interfered with folding of internally tagged $G\alpha_s$ and β2AR. Notably, unlike BphPs, GAF domains of CBCRs are often found as modular components of complex signaling proteins (16), suggesting that miRFP670nano has naturally optimized structure for flexible design of fusion constructs.

We next evaluated applicability of miRFPnanos for imaging of primary cell cultures, such as neurons. Primary rat cortical neurons transfected with miRFP670nano exhibited bright homogenous fluorescence without supplying of exogenous BV (FIG. 13m).

To evaluate miRFP670nano in two-color NIR imaging with monomeric BphP-derived red-shifted miRFP720 (5), we imaged HeLa cells co-expressing different miRFP670nano and miRFP720 fusions (FIG. 13n,o). All fusions had proper localization and clear separation of miRFP670nano and miRFP720 fluorescence signals. Notably, endogenous BV concentration was sufficient to provide bright fluorescence to both NIR FPs co-expressed in the same cells.

Figures 15A, 15B, 15C, 15D, 15E:
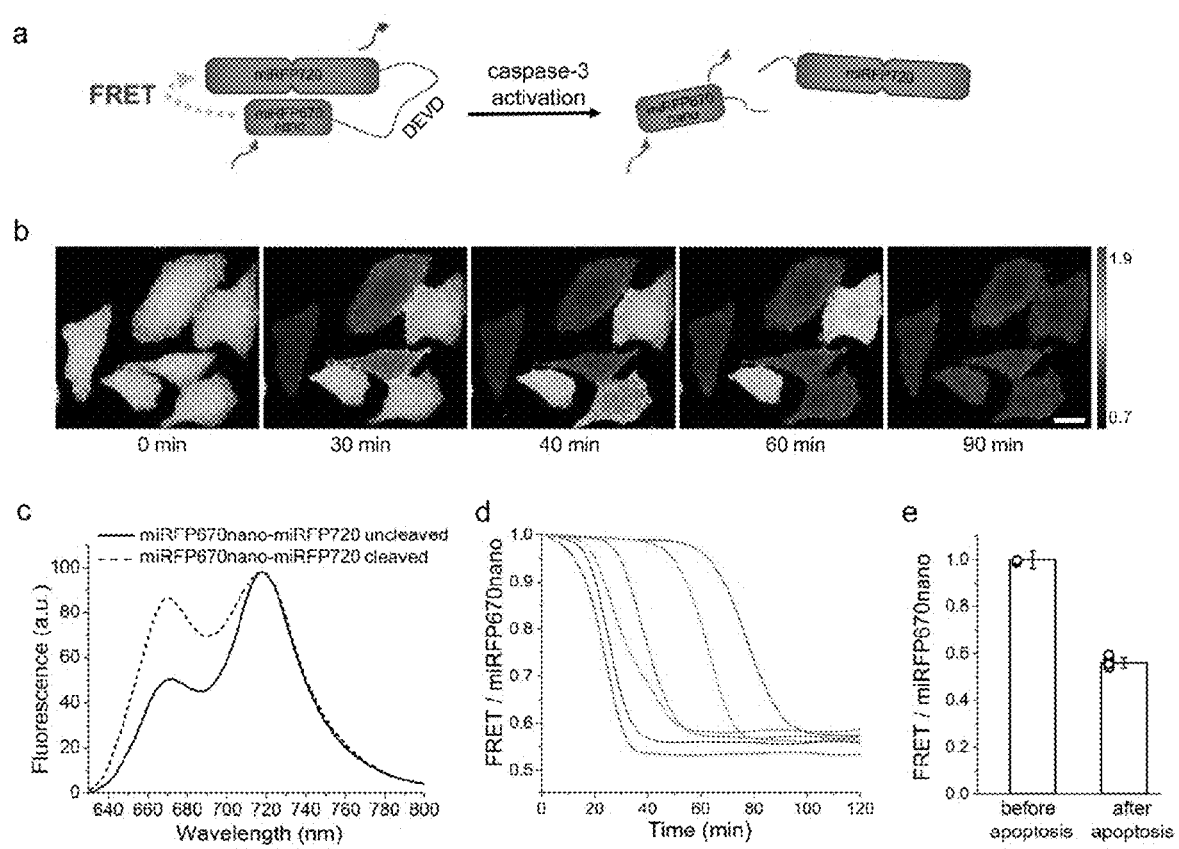
FIG. 15(a)-15(e). miRFP670nano-DEVD-miRFP720 FRET-based reporter for caspase-3 activity. (a) Schematic representation of the caspase-3 activity reporter consisting of miRFP670nano (FRET donor), 11 a.a. linker with DEVD caspase-3 cleavage site, and miRFP720 (FRET acceptor). (b) Time-lapse FRET/miRFP670nano ratio images of HeLa cell expressing miRFP670nano-DEVD-miRFP720 reporter upon apoptosis induced with 10 µM staurosporine, visualized using pseudocolor. (c) Emission spectra of miRFP670nano-DEVD-miRFP720 reporter before and after cleavage. (d) FRET/miRFP670nano ratio time courses of individual cells undergoing apoptosis. (e) FRET/miRFP670nano ratio before and after staurosporine-induced apoptosis. Error bars, s.d. (n=3; independent experiments). Scale bar, 10 µm.

NIR FRET biosensors of PKA and JNK kinases. The high photostability, small size, and relatively high quantum yield make miRFP670nano a promising FRET donor for red-shifted miRFP720 (5). To evaluate this FRET pair, we fused miRFP670nano and miRFP720 via linker with a cleavage site for caspase-3, the key protease in apoptosis (FIG. 15a). Upon apoptosis induced by staurosporine, we observed ~1.65-fold decrease in the FRET/miRFP670nano fluorescence ratio detected at 725 nm/667 nm in HeLa cells transfected with the miRFP670nano-miRFP720 caspase-3 reporter (FIG. 15b-e). These results suggested that miRFP670nano and miRFP720 can be successfully used to design fully NIR FRET biosensors.

Figures 16A, 16B, 16C, 16D, 16E:
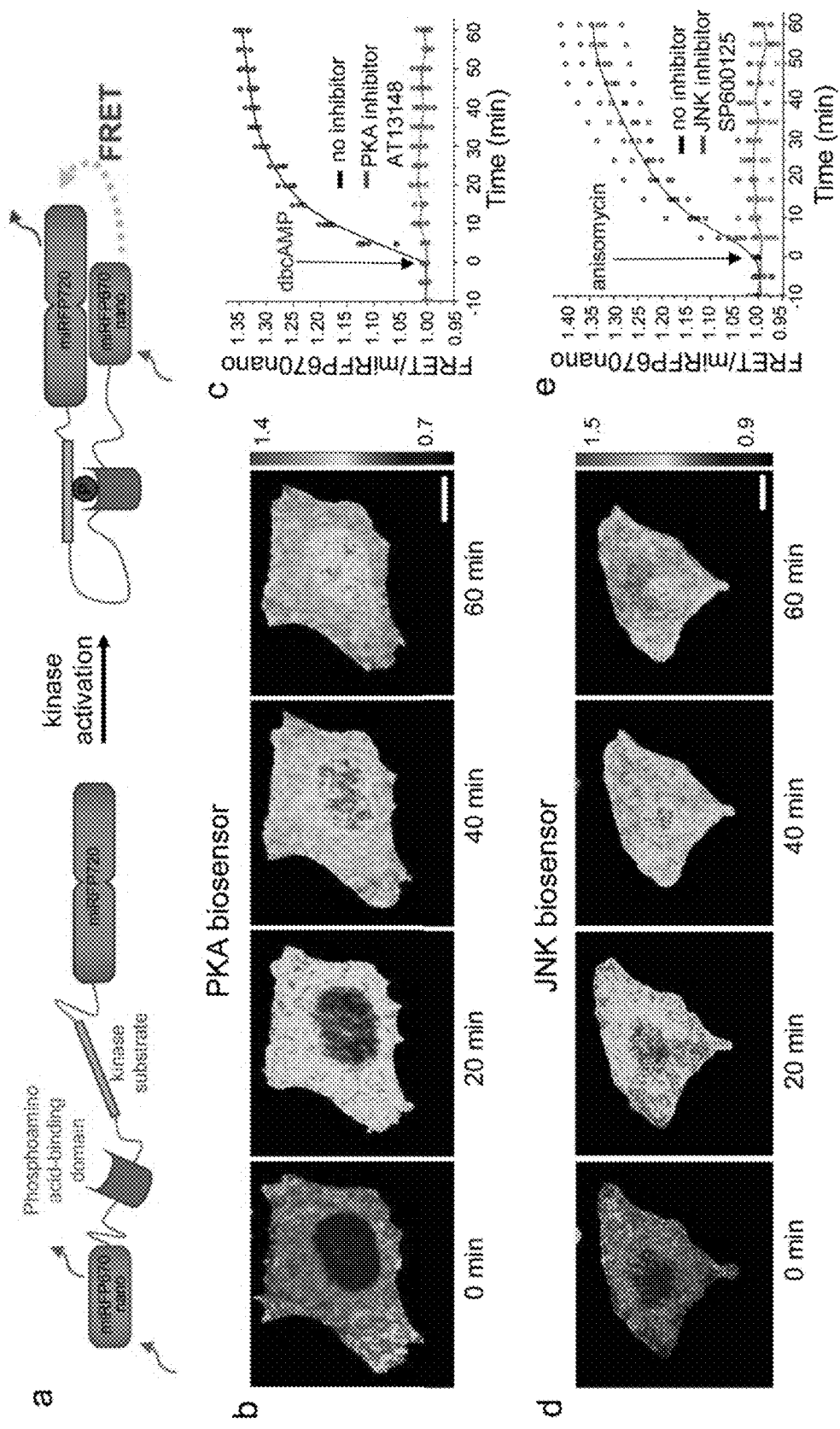
FIG. 16(a)-16(e). NIR biosensors for detection of PKA and JNK kinase activities. (a) Schematic representation of miRFP670nano-miRFP720-based NIR FRET biosensor for kinase activity. (b) Time-lapse FRET/miRFP670nano ratio images of HeLa cell expressing NIR PKA biosensor stimulated with 1 mM dbcAMP and visualized using pseudocolor. (c) FRET/miRFP670nano ratio time courses of HeLa cells expressing PKA biosensor stimulated with dbcAMP in the presence (red) and absence (black) of chemical PKA inhibitor, AT13148 (n=3 independent experiments). (d) Time-lapse FRET/miRFP670nano ratio images of HeLa cell expressing NIR JNK biosensor stimulated with 1 µg ml$^{-1}$ anisomycin and visualized using pseudocolor. (e) FRET/miRFP670nano ratio time courses of HeLa cells expressing JNK biosensor stimulated with anisomycin in the presence (red) and absence (black) of chemical JNK inhibitor, SP600125 (n=3 independent experiments). In b-e the miRFP670nano and FRET fluorescence signals were detected at 667 and 725 nm, respectively. Scale bars, 10 µm.

We next constructed biosensors for detection of Protein Kinase A (PKA) and c-Jun N-terminal kinase (JNK) activities (49). PKA is one of the key effectors of cAMP-mediated signaling pathway, while JNK regulates cellular responses to diverse environmental stress signals and inflammatory cytokines (50). The NIR biosensors consisted of a miRFP670nano donor, a phosphoamino acid binding domain, a consensus peptide sequence of kinases substrates, and a miRFP720 acceptor (FIG. 16a). Phosphorylation of the substrate peptide by activated kinases leads to a conformation rearrangement of the biosensor and an increase of FRET between donor and acceptor.

Stimulation of HeLa cells stably expressing NIR PKA biosensor with 1 mM dibutyryl cyclic adenosine monophosphate (dbcAMP) led to a fast increase in the FRET/miRFP670nano fluorescence ratio, which reached ~33% in 1 h. The response was not detected in the presence of PKA inhibitor AT13148 (FIG. 16b,c). Treatment of HeLa cells expressing the NIR JNK biosensor with 1 µg/ml anisomycin, a JNK agonist (51), led to an increase of the FRET/miRFP670nano fluorescence ratio with typical for JNK kinetics (52), which reached ~35% in 1 h. Incubation with JNK inhibitor SP600125 prevented the response to anisomycin (FIG. 16d,e). Both NIR biosensors exhibited the high dynamic range, similar to that for the PKA and JNK biosensors based on the ECFP-Venus and ECFP-Citrine pairs (52, 53).

Figures 17A, 17B, 17C:
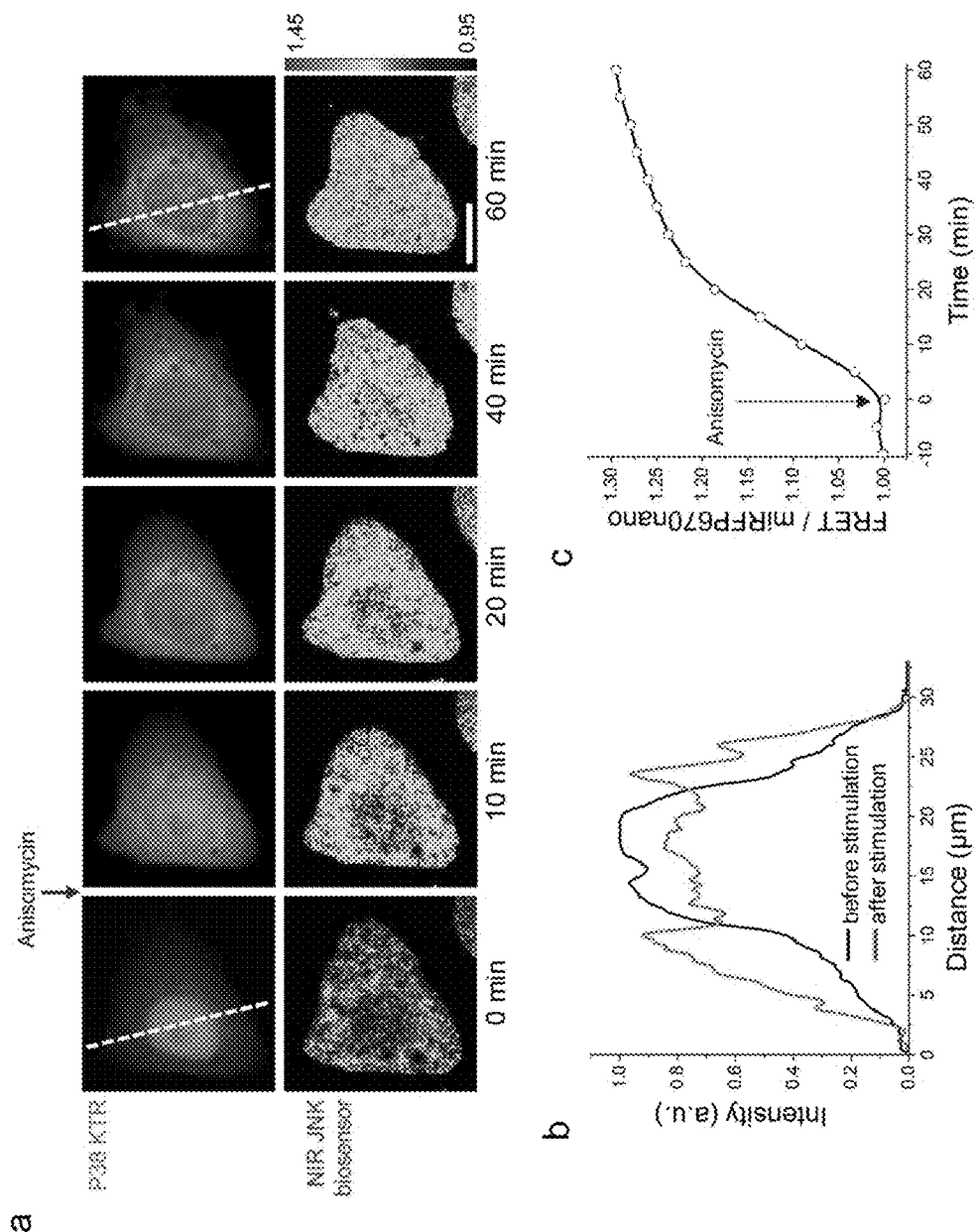
FIG. 17(a)-17(c). HeLa cell stably expressing NIR JNK biosensor co-transfected with p38 kinase translocation reporter (p38 KTR). (a) p38 KTR-EGFP translocation (top row) and FRET/miRFP670nano ratio changes (bottom row) upon stimulation with 1 µg ml$^{-1}$ anisomycin. Dashed line marks the region used for profile plotting. FRET/miRFP670nano ratio images are visualized using intensity pseudocolor. Scale bar, 10 µm. (b) Intensity profiles of p38 KTR-EGFP fluorescence before and after stimulation with anisomycin. (c) Kinetics of FRET/miRFP670nano ratio upon stimulation with anisomycin. The miRFP670nano and FRET fluorescence signals were detected at 667 and 725 nm, respectively.

Spectral multiplexing of NIR biosensors. Important advantage of fully NIR biosensors is their spectral compatibility with GFP-like FPs and common optogenetic tools activatable with blue light. We co-expressed NIR JNK biosensor and EGFP-based p38 kinase translocation reporter (p38 KTR) (54) in HeLa cells. Similarly to JNK, p38 kinase is activated by stress signals and inflammatory cytokines (50, 51). After treatment of cells with anisomycin, which induces activation of both kinases (51), we observed response of both biosensors, NIR JNK and p38 KTR (FIG. 17).

Figures 18A, 18B, 18C, 18D, 18E:
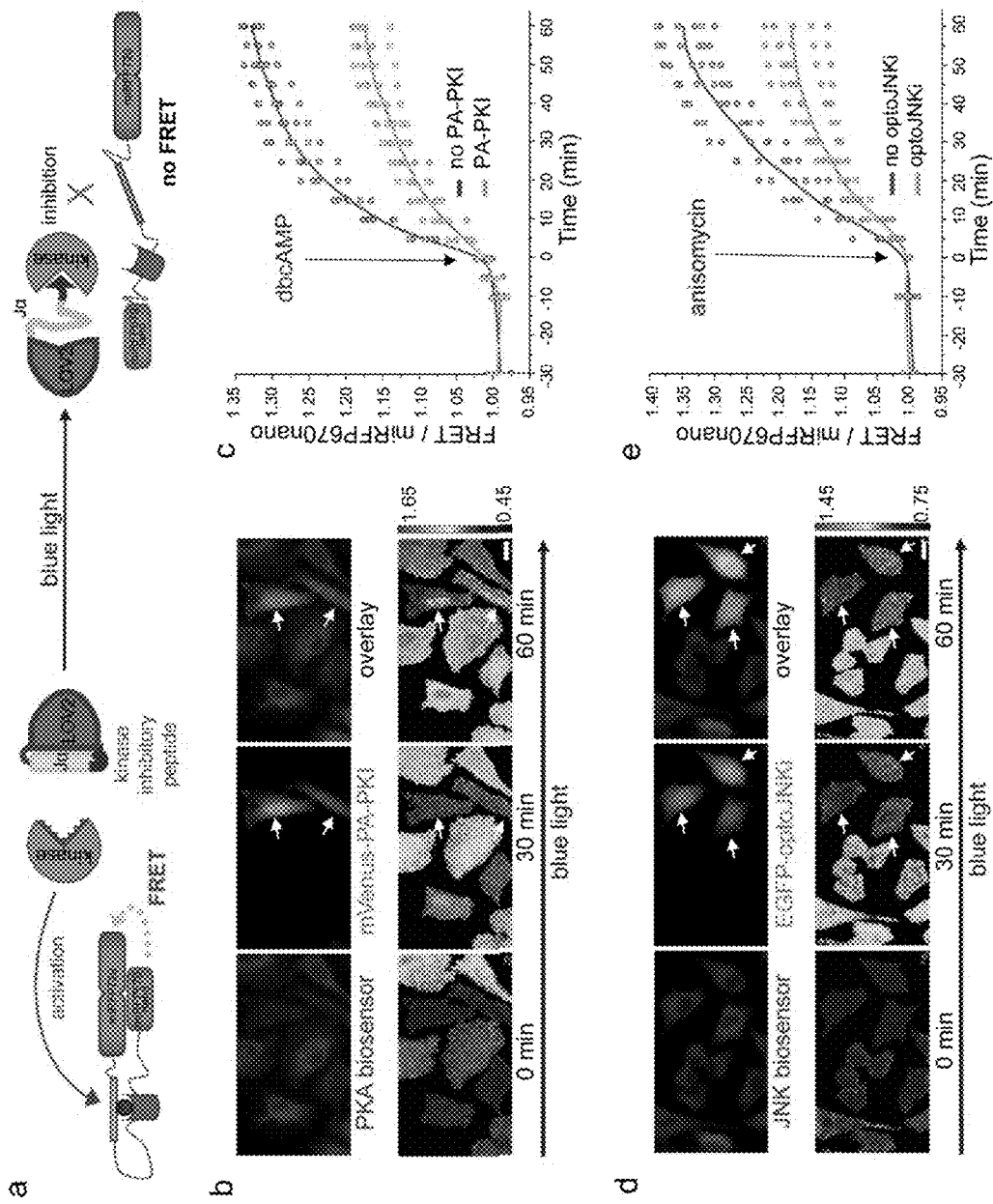
FIG. 18(a)-18(e). Multiplexing of NIR PKA and JNK biosensors with optogenetic kinase inhibitors. (a) Schematic representation of LOV2-domain-based blue-light-regulatable kinase inhibitor in combination with respective fully-NIR kinase biosensor. Upon illumination with blue light, the Jα helix of LOV2 unfolds, resulting in uncaging of a peptide, which inhibits kinase. (b) HeLa cells stably expressing NIR PKA biosensor co-transfected with optogenetic PKA inhibitor, PA-PKI, tagged with mVenus (top row). Upon simultaneous 460 nm illumination and stimulation with 1 mM dbcAMP, the changes in FRET/miRFP670nano ratio are shown in pseudocolor (bottom row). (c) FRET/miRFP670nano ratio time courses of HeLa cells expressing NIR PKA biosensor only (red) or NIR PKA biosensor with PA-PKI (green) upon simultaneous 460 nm illumination and stimulation with 1 mM dbcAMP (n=3 independent experiments). (d) HeLa cells stably expressing JNK biosensor co-transfected with optogenetic JNK inhibitor, optoJNKi, tagged with EGFP (top row). Upon simultaneous 460 nm illumination and stimulation with 1 µg ml$^{-1}$ anisomycin, the changes in FRET/miRFP670nano ratio are shown in pseudocolor (bottom row). (e) FRET/miRFP670nano ratio time courses of HeLa cells expressing NIR JNK biosensor only (red) or NIR JNK biosensor with optoJNKi (green) upon simultaneous 460 nm illumination and stimulation with anisomycin (n=3 independent experiments). White arrows indicate cells expressing optogenetic regulators. In b-e the miRFP670nano and FRET fluorescence signals were detected at 667 and 725 nm, respectively. Scale bars, 10 µm.
Figure 19:
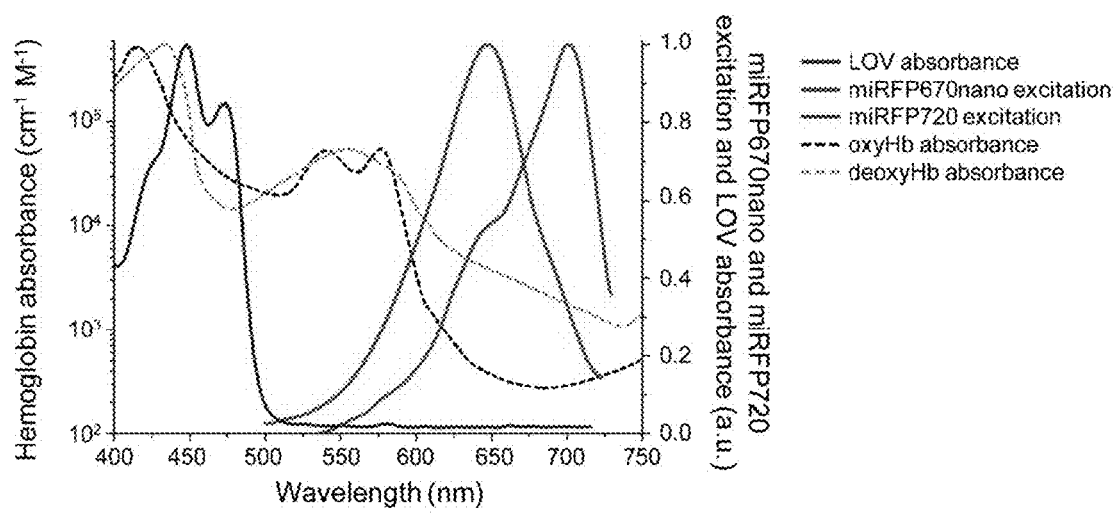
FIG. 19. Non-overlapping spectra of LOV2 domain and miRFP670nano-miRFP720 FRET pair. Spectra of miRFP670 nano and miRFP720 lie in the NIR tissue transparency window (650-900 nm) where the extinction coefficient of both oxyhemoglobin (oxyHb) and deoxyhemoglobin (deoxyHb) are 1-2 orders of magnitude lower than in the blue-green spectral range.

While the combination of several biosensors enables monitoring of several cell processes, a combination of biosensors with optogenetic tools should allow simultaneous detection and regulation of the processes. This is a powerful all-optical approach to study cell signaling in native environment. Recently, a blue-light controlled optogenetic JNK inhibitor (optoJNKi) and a photoactivatable PKA inhibitor (PA-PKI), based on the LOV2 domain from Avena sativa phototropin 1, were developed (55, 56). In these optogenetic tools, PKA or JNK inhibitory peptides are fused to a Jα helix of the LOV2 domain (FIG. 18a). In darkness, the peptides are sterically blocked from kinase interaction whereas blue light leads to unfolding of the Jα helix, uncaging the peptides and, consequently, to kinase inhibition (55, 56). Absorbance spectrum of LOV2 domain and excitation spectra of miRFP670nano donor and miRFP720 acceptor have minimal overlap (FIG. 19).

Figures 20A, 20B:
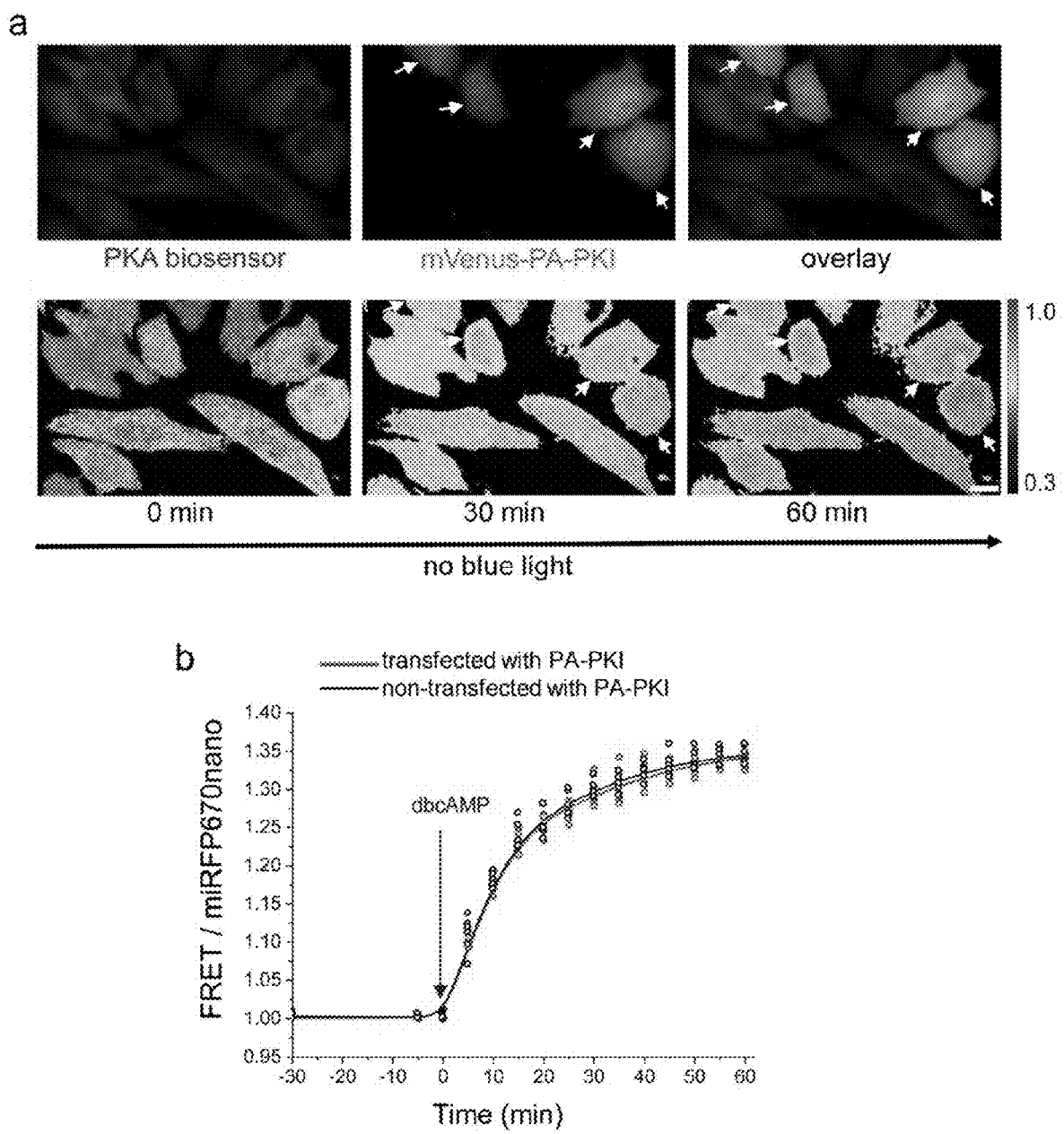
FIG. 20(a)-20(b). Control experiments to evaluate spectral compatibility of NIR PKA biosensor with optogenetic PKA inhibitor. (a) HeLa cells stably expressing NIR PKA biosensor co-transfected with photoactivatable PKA inhibitor, PA-PKI, tagged with mVenus (top row). Upon stimulation with 1 mM dbcAMP without illumination with blue light, the changes in the FRET/miRFP670nano ratio are shown in pseudocolor (bottom row). (b) FRET/miRFP670nano ratio time courses of HeLa cells expressing NIR PKA biosensor only (black) or NIR PKA biosensor with PA-PKI (red) upon stimulation with 1 mM dbcAMP without illumination with blue light (n=3 independent experiments). White arrows indicate cells expressing the optogenetic inhibitor. Scale bar, 10 µm.
Figures 21A, 21B:
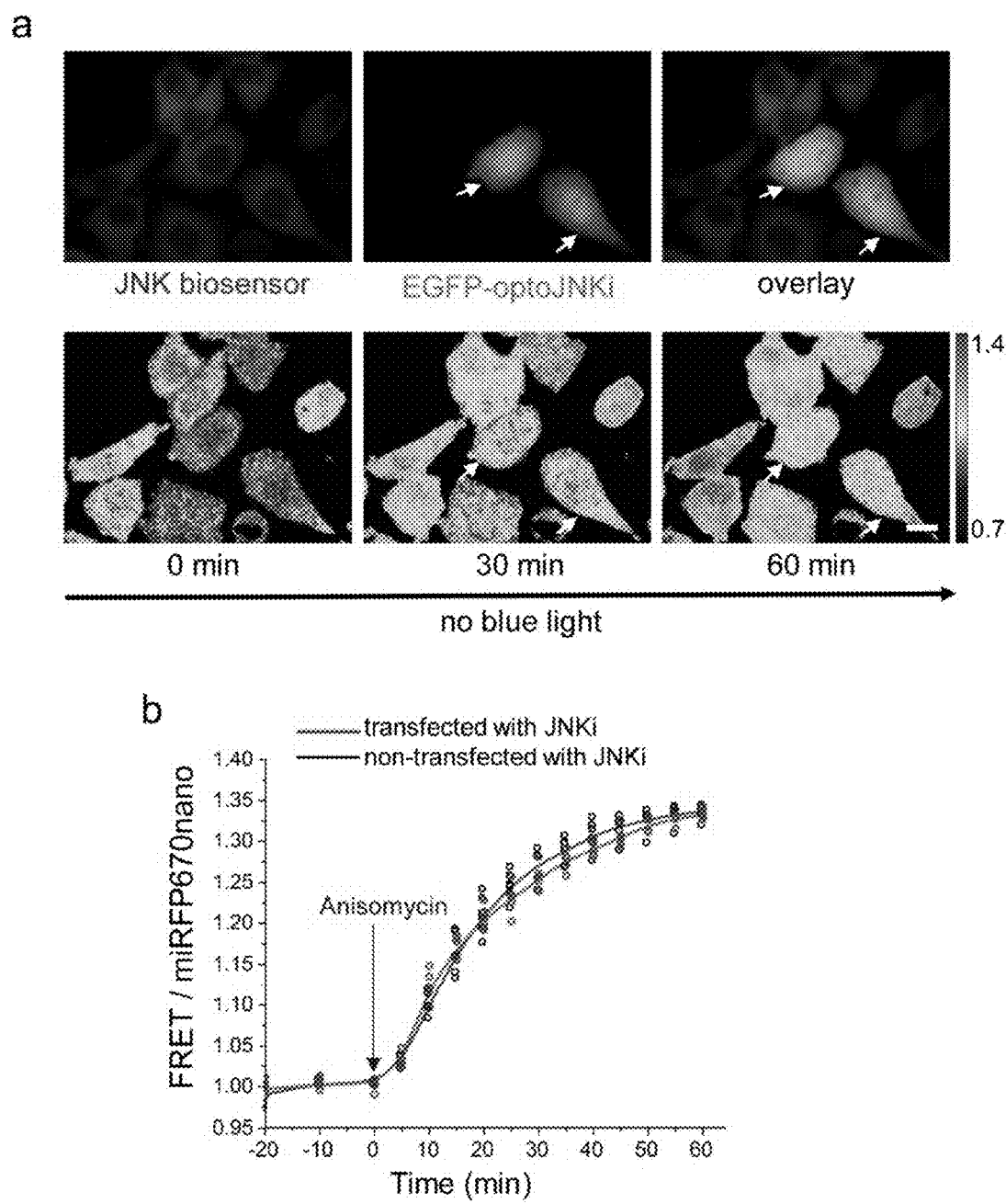
FIG. 21(a)-21(b). Control experiments to evaluate spectral compatibility of NIR JNK biosensor with optogenetic JNK inhibitor. (a) HeLa cells stably expressing NIR JNK biosensor co-transfected with optogenetic JNK inhibitor, optoJNKi, tagged with EGFP (top row). Upon stimulation with 1 µg/ml anisomycin without illumination with blue light, the changes in the FRET/miRFP670nano ratio are shown in pseudocolor (bottom row). (b) FRET/miRFP670nano ratio time courses of HeLa cells expressing NIR JNK biosensor only (black) or NIR JNK biosensor with optoJNKi (red) upon stimulation with 1 µg/ml anisomycin without illumination with blue light (n=3 independent experiments). White arrows indicate cells expressing the optogenetic inhibitor. Scale bar, 10 µm.

To evaluate compatibility of optoJNKi and PA-PKI with NIR biosensors, we transfected HeLa cells stably expressing JNK or PKA biosensors with the respective optogenetic inhibitors. Cells transfected with the optogenetic tools responded to stimuli similarly to the cells expressing the biosensors only (FIGS. 20 and 21). However, under blue light cells with the optogenetic constructs exhibited the substantial decrease in response to the stimuli (FIG. 18b-e). This demonstrated that the NIR JNK and PKA biosensors can be efficiently spectrally multiplexed with optogenetic tools in the same cells.

Figures 22A, 22B, 22C, 22D, 22E:
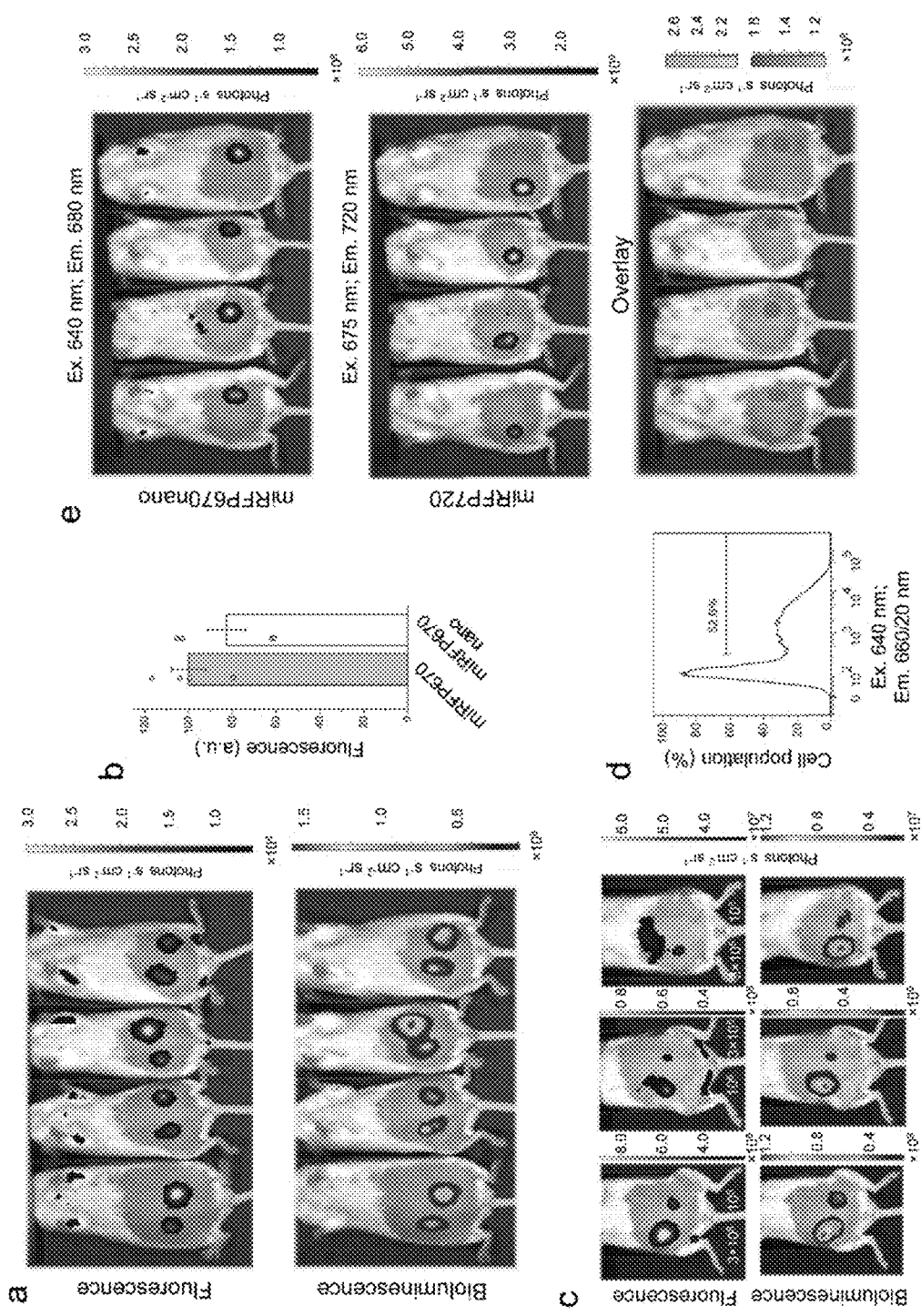
FIG. 22(a)-22(e). Characterization of miRFP670nano in vivo. (a) Comparison of miRFP670nano with miRFP670 in vivo. Fluorescence (top row) and bioluminescence (bottom row) images of living mice injected with 3×10$^6$ HeLa cells expressing miRFP670 (left) and miRFP670nano (right). Cells were co-transfected with Rluc8 (miRFPs:Rluc8 plasmid ratio is 10:1). The fluorescence images were obtained with excitation at 640 nm and emission at 680 nm using IVIS Spectrum instrument 72 h after cell transfection. (b) Brightness of injected HeLa cells expressing miRFP670 or miRFP670nano as shown in a. Mean fluorescence intensity was normalized to mean bioluminescence intensity. Error bars, s.d. (n=3 experiments). (c) Minimal amount of detectable miRFP670nano cells. Fluorescence (top row) and bioluminescence (bottom row) images of living mice injected with various quantity of HeLa cells expressing miRFP670nano. Left mouse was injected with 3×10$^6$ (left) and 10$^6$ (right) cells; middle mouse was injected with 10$^6$ (left) and 3×10$^5$ (right) cells; right mouse was injected with 3×10$^5$ (left) and 10$^5$ (right) cells. Cells were co-transfected with Rluc8 (miRFPs:Rluc8 plasmid ratio is 10:1). The fluorescence images were obtained with excitation at 640 nm and emission at 680 nm 72 h after cell transfection. (d) Transfection efficiency of injected HeLa cells obtained by FACS analysis. (e) Two-color imaging of miRFP670nano and miRFP720 in vivo. Fluorescence images of living mice injected with 3×10$^6$ HeLa cells expressing miRFP670nano (top row) and miRFP720 (middle raw) and its overlay (bottom raw) are shown. The fluorescence images were obtained with excitation at 640 nm and emission at 680 nm for miRFP670nano and with excitation at 675 nm and emission at 720 nm for miRFP720 72 h after cell transfection.

Characterization of miRFPnanos in vivo. To compare miRFP670nano with miRFP670 in in vivo imaging, we injected miRFP670nano- or miRFP670-expressing HeLa cells co-transfected with RLuc8 luciferase in mammary glands of mice. The miRFP670 and miRFP670nano fluorescence signals were normalized to Rluc8 bioluminescence to account for transfection efficiency. We found that in vivo brightness of miRFP670nano cells was comparable to that of miRFP670 cells (FIG. 22a,b). We then estimated the minimal detectable quantity of cells expressing miRFP670nano. For this, we injected in mammary glands various amounts of transiently transfected cells and found that we were able to detect ~$1.5 \times 10^5$ fluorescent cells (FIG. 22c,d). We next tested miRFP670nano in two-color whole-body imaging. Cells transfected with either miRFP670nano or miRFP720 were well spectrally distinguished in mice using two channels with ex./em. at 640 nm/680 nm and 675 nm/720 nm, respectively (FIG. 22e). Overall, these in vivo results showed that miRFP670nano performs well in whole-body imaging and can be used in combination with red-shifted NIR FPs.

Discussion

By applying 17 rounds of molecular evolution to the GAF domain of PCB-binding NpR3784 CBCR, we have developed the first CBCR-based NIR FP miRFP670nano, which efficiently binds endogenous BV and fluoresces in various mammalian cells (FIG. 4e). We next developed spectrally distinct NIR FPs miRFP704nano with excitation/emission at 680 nm/704 nm and miRFP718nano with excitation/emission at 690 nm/718 nm (FIG. 11). We also engendered miRFP670nano3 FP (excitation/emission at 645 nm/670 nm) with improved brightness (FIG. 11c). With molecular weight of only 17 kDa, miRFPnanos are the smallest monomeric NIR FPs that fluoresce in mammalian cells as bright as twice bigger state-of-art two-domain NIR FPs.

Comparing to BphP-based NIR FPs, miRFPnanos are characterized by high stability to acidic environment, denaturation conditions, cell fixation, and degradation in mammalian cells (FIG. 4c,g,h,i and FIG. 5, 6). Compact protein fold with N- and C-termini in a close proximity allows the use of miRFPnanos not only as a protein terminal tag but also as an insertion inside the loops of a protein of interest, as demonstrated for Gαs and β2AR (FIG. 13p,q and FIG. 14). In contrast, two-domain BphP-derived NIR FPs, which have the figure-of-eight knot in their structure and distant termini, are not suitable for internal tagging.

The crystal structure of miRFP670nano allows to visualize the chromophore and its immediate environment optimized during molecular evolution for BV binding and fluorescence (FIG. 9). Bound to the conserved Cys86 via its $C3^1$ atom, BV forms a chromophore, which lacks a double bond between C2 and C3, but has a double bond between $C3^1$ and $C3^2$. The number of conjugated double bonds in this chromophore is the same as in the chromophores of blue-shifted BphP-derived NIR FPs that explains their spectral similarity (FIG. 8h-l). However, the BphP-derived NIR FPs have two different chromophore types (FIG. 8e,f), which leads to heterogeneity of the protein species and, consequently, affects their properties. Likely, the presence of two protein species in miRFP670 explains its slightly sigmoidal maturation (FIG. 4d), bi-exponential photobleaching (FIG. 4f) and wider spread of denaturation dependence (FIG. 5). The chromophore homogeneity is another important advantage of CBCR-based miRFP670nano over blue-shifted BphP-based NIR FPs.

Relatively high quantum yield of miRFP670nano and miRFP670nano3 and good overlap of their emission with miRFP720 excitation make miRFP670nanos favorable FRET donors for red-shifted NIR FPs. That was demonstrated by the development of efficient fully-NIR biosensors of PKA and JNK activities (FIG. 16). JNK is key transducer of exogenous stress signals and is involved in regulation of a number of physiological and pathological processes including apoptosis, proliferation, embryonic development and inflammation. PKA mediates signals of G-protein-coupled receptors and regulates a plethora of downstream effectors involved in key cellular processes. The developed NIR PKA and JNK biosensors enable multiplexing with blue-green optogenetic tools for probing and monitoring of multiple cell processes for better understanding of mechanisms that mediate regulation and specificity of PKA and JNK kinases. Simultaneous detection and light-control of the PKA and JNK activities using the fully-NIR miRFP670nano-miRFP720-based biosensors and the respective blue-light-activatable kinase regulators (FIG. 18)

demonstrated the wide applicability of miRFP670nano and miRFP670nano-miRFP720 FRET pair in non-invasive all-optical assays in single cells and in vivo.

Although red-shifted monomeric miRFP704nano and miRFP718nano can be utilized in the same applications as described for RpBphP1-derived miRFPs, and are particularly advantageous for applications in FRET biosensors.

NIR fluorescence makes miRFPnanos a useful probe not only for crosstalk-free spectral multiplexing in microscopy, but also for deep-tissue imaging. In mice, miRFP670nano performed similarly to miRFP670 and could be used in multicolor tissue labeling with red-shifted NIR FP (FIG. 22).

To date, the large number of CBCRs has been cloned. Unlike natural BphPs, different subclasses of CBCRs exhibit the remarkable spectral diversity, sensing light from UV to NIR spectral ranges (1). The CBCR spectral tuning is mainly associated with the characteristic amino acid motifs (57), frequently containing Cys residues able to form thioether bonds with different carbon atoms of the PCB chromophore, hence, affecting degree of its electron conjugation. Directed mutagenesis allows changing of CBCR absorbing spectra, as we demonstrated for development of miRFP704nano and miRFP718nano. CBCRs can be used as a source of the whole new class of small and stable BV-binding FPs with spectral variety from UV to NIR.

In conclusion, the developed spectrally distinct small monomeric miRFPnanos and miRFPnano-based biosensors allow non-invasive multicolor visualization of biological processes across scales: from molecules to whole animals. The advantages of miRFPnanos make it the NIR FPs of choice for imaging applications in basic biology and biomedicine.

Materials and Methods

Mutagenesis and directed molecular evolution. The CBCR GAF genes were synthesized by GenScript Company. The DNA sequences were optimized with Optimum-Gene algorithm (GenSript), taking into account the codon usage bias (human cells), GC content, CpG dinucleotides content, mRNA secondary structure, and other parameters. For expression in bacteria, DNA sequences encoding the GAF domains were cloned into pBAD/His-B vector (Life Technologies/Invitrogen) by KpnI/EcoRI sites. BV synthesis in bacteria was facilitated by co-transformation with a pWA23h plasmid encoding heme oxygenase from *Bradyrhizobium* ORS278 (hmuO) under the rhamnose promoter (18, 58). LMG194 host cells (Invitrogen) were used for protein expression.

All oligonucleotides were purchased from Biomers. For simultaneous site-specific mutagenesis at several positions, an overlap-extension approach was applied. Random mutagenesis was performed with GeneMorph II random mutagenesis kit (Agilent Technologies) under conditions resulting in a mutation frequency of up to 16 mutations per 1,000 base pairs. After mutagenesis, a mixture of mutated genes was electroporated into LMG194 host cells containing the pWA23h plasmid. Typical mutant libraries consisted of more than $10^8$ independent clones. Bacterial cells were incubated overnight at 37° C. in LB medium supplemented with ampicillin and kanamycin.

To start protein expression 0.02% rhamnose and 0.004% arabinose were added. Cells were grown for 5 h at 37° C., then at 22° C. for 20 h. Before sorting, bacterial cells were washed with phosphate-buffered saline (PBS) and diluted with PBS to an optical density of 0.03 at 600 nm. Flow cytometry screening was performed on BD Influx cell sorter (BD Biosciences). 640 nm or 685 nm laser for excitation and a 670/30 nm or 725/40 nm emission filter were used for selection of positive clones. Collected cells were rescued in SOC medium for 1 h at 37° C., and then plated on LB/ampicillin/kanamycin Petri dishes supplemented with 0.004% arabinose and 0.02% rhamnose. Leica M205 FA fluorescence stereomicroscope equipped with a filter set ET CY5.5 (650/45 nm excitation and 710/50 nm emission filters) and a CCD camera (Tucsen) was used for screening of brightest clones. About 30 mutants selected in bacteria were then tested in HeLa cells, transfected with plasmids obtained after cloning of FPs genes into pcDNA3.1(+) plasmid (Invitrogen/Thermo-Fisher Scientific). A mixture of several selected mutants was then used as a template for the next round of mutagenesis.

Proteins expression and characterization. miRFPnanos with polyhistidine tag on the N termini were expressed in bacteria as described above for sorting of libraries of mutants. Proteins were purified with Ni-NTA agarose (Qiagen). For proteins elution PBS containing 100 mM EDTA was used. Then the samples were desalted using PD-10 desalting columns (GE Healthcare).

To perform size exclusion liquid chromatography a 2 ml volume of purified miRFP670nano was applied on the HiLoad 16/600 Superdex 200 column (GE Healthcare) equilibrated with 10 mM HEPES buffer pH 7.4 containing 50 µM EDTA, 10% glycerol, 150 mM NaCl, 1 mM DTT, 0.2 mM PMSF, 0.01% EP-40 and 0.2 mM benzodiazepin. A 1 ml/min flow rate was used. The column was calibrated using the gel filtration standards from Bio-Rad Cary Eclipse Fluorescence Spectrophotometer (Agilent Technologies) was used for recording of fluorescence spectra, Hitachi U-2000 spectrophotometer was used for absorbance measurements. The extinction coefficient was calculated as a ratio between the maximum absorbance of the main peak at Q-band and the side peak at Soret band and assumed that the extinction coefficient at Soret band corresponds to 39,900 $M^{-1}cm^{-1}$ [16]. To determine fluorescence quantum yield, we compared the fluorescence signal of a purified protein to that of an equally absorbing Nile blue dye. pH titrations were done using a series of Hydrion buffers (Micro Essential Laboratory).

To study protein folding and maturation, LMG194 bacterial cells expressing miRFP670nano and miRFP670 were grown overnight at 37° C. in LB medium. The next morning, 0.2% rhamnose was added for 2 h, subsequently 0.002% arabinose was added, and cells were cultured for 1 h. Then arabinose was washed out, and cells were cultured in LB medium with 0.2% rhamnose at 37° C. Fluorescence intensities of the equal aliquots of the cell suspension were measured at intervals after dilution to the same optical density of 0.2, and the obtained values were multiplied by the dilution factor.

Protein crystallization. For crystallization, purifed miRFP670nano was transferred to a buffer containing 20 mM Tris-HCl, 200 mM NaCl at pH 8.0 and concentrated to 28.4 mg $mL^{-1}$ using Amicon Ultra-15 centrifugal filter units with 10 kDa molecular weight cutoff cellulose membrane (Millipore). A search for crystallization conditions was carried out using a Mosquito robotic crystallization system (TTP Lab Tech). Potentially promising crystallization conditions were further optimized using Hampton Research additive screens. Successful conditions were further optimized manually. Large-scale crystallization trials were performed using the hanging drop vapor diffusion method. Typically, 2 µL of the protein solution was mixed with 2 µL of the reservoir solution and incubated over 500 mL of the same reservoir solution at 20° C. for 2 weeks. The best crystals of miRFP670nano were obtained from 0.1 M sodium acetate pH 4.0, 10 mM EDTA, 10% v/v isopropanol, 22% w/v PEG 6,000.

Diffraction data collection and processing. X-ray diffraction data were collected on SER-CAT 22-ID beamline (Advanced Photon Source, Argonne National Laboratory, Argonne, IL). Diffraction image intensities were registered on Rayonix MX300HS CCD detector. Prior to data collection the crystals were briefly soaked (5-10 s) in a cryoprotecting solution consisting of 20% glycerol and 80% of well solution and were flash-frozen in a 100 K nitrogen stream; throughout the diffraction experiment the cryogenic temperature was maintained by a CryoJetXL cooling device (Oxford Cryosystems). To minimize radiation damage of the crystals a helical data collection technique was used for all X-ray data acquisitions. Diffraction images were indexed, integrated and scaled with the HKL2000 software (59).

Structure solution, refinement and analysis. Initial phases for miRFP670nano were obtained by the molecular replacement method with MOLREP (60) using the structure of the GAF domain of putative phototaxis regulator PixJs of *Anabaena* sp. PCC 7120 (denoted as AnPixJ, PDB ID: 3W2Z, (42)) in its red-absorbing state as a search model. To increase the contrast of rotation function the search model was truncated to the residues 36-183. To remove model bias, the chains were rebuilt with the PHENIX.AUTOBUILD crystallographic molecular model building suite (61, 62). Real space model correction and the search for the ordered solvent molecules was performed with COOT (63). Maximum likelihood structure refinement was performed with REFMAC (64). Structure validation was carried out with COOT and PROCHECK (65). The volume of the chromophore binding pockets has been calculated with POCKDRUG (66).

Construction of mammalian plasmids. To construct mammalian expression plasmids, the respective genes of miRFP670nano or mutants were inserted in a pcDNA3.1 plasmid (Invitrogen/Thermo Fisher Scientific) by KpnI/EcoRI sites. For protein tagging and labeling of intracellular structures study, miRFP670nano was amplified, digested with restriction enzymes and then swapped with miRFP703 either as C- (for α-tubulin and clathrin) or N-terminal fusions (for keratin, α-actinin, LifeAct, EB3, myosin, vimentin, clathrin, LAMP1 and H2B).

To engineer caspase-3 activity NIR-reporter, fusion of miRFPP670nano and miRFP720, containing 11 amino acid linker with the caspase-3 recognition site (GGDEVDGP-VAT), was designed. For this, a miRFP670nano gene was PCR amplified using primers containing the linker sequence, NheI and AgeI sites and inserted into pcDNA3.1 plasmid (Invitrogen/Thermo Fisher Scientific), then miRFP720 gene was inserted by AgeI and NotI sites.

To create a JNK and PKA activity NIR-biosensor plasmids, we used a pJNKAREV-NES (3555NES) and pAKAR3EV-NES (3536NES) plasmids (49) kindly provided by K. Aoki. A YPet gene was replaced with miRFP670nano gene by EcoRI/XhoI sites. An ECFP gene was replased with miRFP720 gene by NotI/XbaI sites. Then, fragments encoding NIR-sensors were cut out with EcoRI and SalI restriction endonucleases and inserted into pcDNA3.1 plasmid (Invitrogen/Thermo Fisher Scientific). Fragment encoding p38m-KTR was cut out from pLentiPGK Puro DEST p38KTRClover (a gift from Markus Covert (Addgene plasmid #59152)) with EcoRI and AgeI restriction endonucleases and inserted into pEGFP-N1 (Clontech). Venus-PA-PKI was a gift from Klaus Hahn (Addgene plasmid #65456). OptoJNKi was cut out from OptopKCAG-mCherry-OptoJNKi (a gift from Michael Courtney (Addgene plasmid #89738)) with EcoRI and BamHI restriction endonucleases and inserted into pEGFP-C1 (Clontech).

Mammalian cells and transfection. HeLa, U87, U205, NIH3T3 and PC6-3 cells were purchased from the ATCC. Cells were grown in a DMEM medium supplemented with 10% FBS, 0.5% penicillin-streptomycin and 2 mM glutamine (Life Technologies/Invitrogen). For microscopy, cells were cultured in 35 mm glass-bottom Petri dishes (Greiner Bio-One International). Plasmid transfections were performed using polyethylenimine (67). Stably expressing cells were selected with 1 mg ml$^{-1}$ G418 antibiotic. Sorting of positive cells was performed using a BD Influx cell sorter (BD Biosciences) equipped with 640 nm laser for excitation and a 670/30 nm emission filter or 680 nm laser for excitation and a 725/40 nm emission filter.

Cell Fixation. HeLa cells transfected with miRFP670nano, miRFP670 and miRFP703 were dissociate from culture dishes with 0.25% trypsin (Gibco/Thermo Fisher Scientific), washed and re-suspended in PBS. For fixation 10$^6$ cells were incubated on ice with 1 ml of 4% paraformaldehyde solution for 10, 30 or 60 min and then washed. Fluorescence was measured using Cary Eclipse Fluorescence Spectrophotometer (Agilent Technologies).

Neuronal culture and transfection. Primary rat cortical neurons were prepared in Neuronal Cell Culture Unit, University of Helsinki. All animal work was performed in accordance with the ethical guidelines of the European convention and regulations of an Ethics committee for animal research of the University of Helsinki. Cells were plated at a density of 600,000-700,000 per glass bottom 35 mm dishes coated with Poly-L-Lysine (0.01 mg/ml) (Merck) in a neurobasal medium (Gibco) supplemented with B27 (Life Technologies/Invitrogen), L-glutamine (Invitrogen), and penicillin-streptomycin (Lonza). Cultured neurons were transfected at 2-3 days in vitro (DIV) with a pcDNA3.1 plasmid (Invitrogen/Thermo Fisher Scientific), encoding miRFP670nano using Effectene Transfection Reagent (Qiagen). Neurons were imaged 48 h after transfection.

Widefield fluorescence microscopy. Live cells were imaged with an Olympus IX81 inverted epifluorescence microscope 48 h after the transfection. The microscope was equipped with a 200 W metal halide arc lamp (Lumen220PRO, Prior), a 60×1.35 numerical aperture (NA) oil objective lens (UPlanSApo, Olympus) and an opiMOS sCMOS camera (QImaging). During imaging HeLa cells were incubated in a cell imaging medium (Life Technologies-Invitrogen) and kept at 37° C. The microscope was operated with a SlideBook v.6.0.8 software (Intelligent Imaging Innovations). To separately image miRFP670nano and miRFP720 in one cell (two NIR color imaging), the two filter sets (605/30 nm exciter and 667/30 nm emitter, and 685/20 nm exciter and 725/40 nm emitter) (Chroma) were used.

Photobleaching measurements of cytoplasmically expressed NIR FPs in live HeLa cells were performed with the 60×1.35 NA oil immersion objective lens (UPlanSApo, Olympus) and a 650/13 nm (exciter) and 684/24 nm (emitter) or 665/45 nm (exciter) and 725/50 nm (emitter) filter sets.

To obtain FRET images a 605/30 excitation filter and two emission filters (667/30 nm for miRFP670nano and 725/40 nm for miRFP720) were used. Emission ratios were obtained by calculating background-subtracted FRET intensities divided by background-subtracted miRFP670nano intensities for JNK and PKA NIR biosensors. For caspase-3 reporter FRET to donor intensities ratio was calculated. For caspase-3 reporter donor to FRET intensities ratio was calculated. FRET measurements were quantified using ImageJ (NIH). Intensity-modulated display mode was generated with a full-spectrum lookup table. Time-course ratio measurements were normalized to baseline prestimulation values. HeLa cells expressing JNK and PKA NIR-biosensors were starved for 6 h with DMEM medium (Gibco/Thermo Fisher Scientific) before imaging. To photoactivate PA-PKI and OptoJNKi, the transfected cells were continuously illuminated using 460/20 nm custom-assembled LED array (LED Engin) at the light power density of 0.5 mW $cm^{-2}$.

Flow cytometry. Flow cytometry analysis was performed using a BD Accuri C6 flow cytometer equipped with the 488 nm, and 640 nm lasers and a set of emission filters. Fluorescence of NIR FPs was detected with a 670 nm LP or 675/25 nm emission filters. EGFP was excited with a 488 nm laser, and its fluorescence was detected with a 510/15 nm emission filter. 20,000-50,000 events for each cell type were analyzed. To quantify cell fluorescence, a mean fluorescent intensity of the double-positive population in the NIR channel was divided by a mean fluorescence intensity of the same population in the green channel, thus normalizing NIR signal to transfection efficiency. The data were analyzed using a FlowJo v.7.6.2 software.

Imaging in mice. The Swiss Webster 2- to 3-month-old female mice (National Cancer Institute, NIH) with body weights of 22-25 g were used. To compare brightness of miRFP670nano with miRFP670 as well as to show possibility of two-color imaging HeLa cells were injected subcutaneously in the interscapular area of FVB mice. For better imaging, the fur on the bellies of the mice was removed using a depilatory cream. HeLa cells were co-transfected with the pcDNA3-miRFP670nano or pcDNA-miRFP670 and pRluc8 plasmids in a 10:1 ratio for comparison study. HeLa cells were transfected with the pcDNA3-miRFP670nano or pmiRFP720 and pRluc8 plasmids for two-color study. Various number of HeLa cells in 100 μl of RPMI-1640 media supplemented with 2 mM L-glutamine were injected subcutaneously 72 h after the transfection. For fluorescence and bioluminescence detection, 1 h after the HeLa cells injection the animals were imaged using an IVIS Spectrum instrument (PerkinElmer/Caliper Life Sciences). Fluorescence was detected with 640/20 nm excitation and 680/30 nm emission filters for miRFP670nano or 675/20 nm excitation and 720/30 nm emission filters for miRFP720. Bioluminescence was detected with an open emission filter. Throughout the imaging, animals were maintained under anesthesia with 1.5% vaporized isofluorane. Prior to imaging, 80 μg of Inject-A-Lume coelenterazine substrate for Rluc8 (NanoLight Technology) was intravenously injected through a retro-orbital vein. Data were analyzed using Living Image 3.0 software (Perkin Elmer/Caliper Life Sciences). All animal experiments were performed in an AAALAC-approved facility using protocols approved by the Albert Einstein College of Medicine Animal Usage Committee. 45 mice were used in this study.

REFERENCES

1. Oliinyk O S, Chernov K G, Verkhusha V V. 2017. *Int J Mot Sci* 18
2. Shcherbakova D M, Stepanenko O V, Turoverov K K, Verkhusha V V. 2018. *Trends Biotechnol* 36: 1230-43
3. Shcherbakova D M, Baloban M, Emelyanov A V, Brenowitz M, Guo P, Verkhusha V V. 2016. *Nat Commun* 7: 12405
4. Yu D, Baird M A, Allen J R, Howe E S, Klassen M P, et al. 2015. *Nat Methods* 12: 763-5
5. Shcherbakova D M, Cox Cammer N, Huisman T M, Verkhusha V V, Hodgson L. 2018. *Nat Chem Biol* 14: 591-600
6. Rumyantsev K A, Shcherbakova D M, Zakharova N I, Emelyanov A V, Turoverov K K, Verkhusha V V. 2015. *Sci Rep* 5: 18348
7. Rodriguez E A, Tran G N, Gross L A, Crisp J L, Shu X, et al. 2016. *Nat Methods* 13: 763-9
8. Ding W L, Miao D, Hou Y N, Jiang S P, Zhao B Q, et al. 2017. *Biochim Biophys Acta* 1864: 1877-86
9. Shemetov A A, Oliinyk O S, Verkhusha V V. 2017. *Cell Chem Biol* 24: 758-66 e3
10. Ikeuchi M, Ishizuka T. 2008. *Photochem Photobiol Sci* 7: 1159-67
11. Rockwell N C, Lagarias J C. 2010. *Chemphyschem* 11: 1172-80
12. Rockwell N C, Martin S S, Lim S, Lagarias J C, Ames J B. 2015. *Biochemistry* 54: 3772-83
13. Lim S, Rockwell N C, Martin S S, Dallas J L, Lagarias J C, Ames J B. 2014. *Photochem Photobiol Sci* 13: 951-62
14. Rockwell N C, Martin S S, Feoktistova K, Lagarias J C. 2011. *Proc Natl Acad Sci USA* 108: 11854-9
15. Rockwell N C, Martin S S, Lagarias J C. 2016. *Biochemistry* 55: 3907-19
16. Rockwell N C, Martin S S, Lagarias J C. 2015. *Photochem Photobiol Sci* 14: 929-41
17. Filonov G S, Piatkevich K D, Ting L M, Zhang J, Kim K, Verkhusha V V. 2011. *Nat Biotechnol* 29: 757-61
18. Shcherbakova D M, Verkhusha V V. 2013. *Nat Methods* 10: 751-4
19. Fischer A J, Lagarias J C. 2004. *Proc Natl Acad Sci USA* 101: 17334-9
20. Narikawa R, Nakajima T, Aono Y, Fushimi K, Enomoto G, et al. 2015. *Sci Rep* 5: 7950
21. Narikawa R, Fushimi K, Ni Ni W, Ikeuchi M. 2015. *Biochem Biophys Res Commun* 461: 390-5
22. Fushimi K, Nakajima T, Aono Y, Yamamoto T, Ni Ni W, et al. 2016. *Front Microbiol* 7: 588
23. Akerboom J, Rivera J D, Guilbe M M, Malave E C, Hernandez H H, et al. 2009. *J Biol Chem* 284: 6455-64
24. Subach O M, Barykina N V, Anokhin K V, Piatkevich K D, Subach F V. 2019. *Int J Mol Sci* 20
25. Altschul S F, Gish W, Miller W, Myers E W, Lipman D J. 1990. *J Mol Biol* 215: 403-10
26. Shcherbakova D M, Baloban M, Verkhusha V V. 2015. *Curr Opin Chem Biol* 27: 52-63
27. Wagner J R, Zhang J, von Stetten D, Gunther M, Murgida D H, et al. 2008. *J Biol Chem* 283: 12212-26
28. Lehtivuori H, Rissanen I, Takala H, Bamford J, Tkachenko N V, Ihalainen J A. 2013. *J Phys Chem B* 117: 11049-57
29. Gustin K E, Burk R D. 1993. *Biotechniques* 14: 22, 4
30. Barany F. 1985. *Gene* 37: 111-23
31. Colicelli J, Lobel L I, Goff S P. 1985. *Mol Gen Genet* 199: 537-9
32. Higgins D G, Sharp P M. 1989. *Comput Appl Biosci* 5: 151-3
33. Keown W A, Campbell C R, Kucherlapati R S. 1990. *Methods Enzymol* 185: 527-37
34. Matz M V, Fradkov A F, Labas Y A, Savitsky A P, Zaraisky A G, et al. 1999. *Nat Biotechnol* 17: 969-73

35. Filippin L, Magalhaes P J, Di Benedetto G, Colella M, Pozzan T. 2003. *J Biol Chem* 278: 39224-34
36. Nagai T, Sawano A, Park E S, Miyawaki A. 2001. *Proc Natl Acad Sci USA* 98: 3197-202
37. Nagai T, Yamada S, Tominaga T, Ichikawa M, Miyawaki A. 2004. *Proc Natl Acad Sci USA* 101: 10554-9
38. Ntziachristos V, Razansky D. 2010. *Chem Rev* 110: 2783-94
39. Razansky D, Buehler A, Ntziachristos V. 2011. *Nat Protoc* 6: 1121-9
40. Wang L V, Hu S. 2012. *Science* 335: 1458-62
41. Shcherbakova D M, Baloban M, Pletnev S, Malashkevich V N, Xiao H, et al. 2015. *Chem Biol* 22: 1540-51
42. Narikawa R, Ishizuka T, Muraki N, Shiba T, Kurisu G, Ikeuchi M. 2013. *Proc Natl Acad Sci USA* 110: 918-23
43. Baloban M, Shcherbakova D M, Pletnev S, Pletnev V Z, Lagarias J C, Verkhusha V V. 2017. *Chem Sci* 8: 4546-57
44. Stepanenko O V, Baloban M, Bublikov G S, Shcherbakova D M, Stepanenko O V, et al. 2016. *Sci Rep* 6: 18750
45. Oliinyk O S, Shemetov A A, Pletnev S, Shcherbakova D M, Verkhusha V V. 2019. *Nature Communications* 10
46. Tian G W, Mohanty A, Chary S N, Li S, Paap B, et al. 2004. *Plant Physiol* 135: 25-38
47. Hynes T R, Mervine S M, Yost E A, Sabo J L, Berlot C H. 2004. *J Biol Chem* 279: 44101-12
48. Nakanishi J, Takarada T, Yunoki S, Kikuchi Y, Maeda M. 2006. *Biochem Biophys Res Commun* 343: 1191-6
49. Komatsu N, Aoki K, Yamada M, Yukinaga H, Fujita Y, et al. 2011. *Mol Biol Cell* 22: 4647-56
50. Gerits N, Kostenko S, Shiryaev A, Johannessen M, Moens U. 2008. *Cell Signal* 20: 1592-607
51. Stadheim T A, Kucera G L. 2002. *Leukemia Research* 26: 55-65
52. Fosbrink M, Aye-Han N N, Cheong R, Levchenko A, Zhang J. 2010. *Proc Natl Acad Sci USA* 107: 5459-64
53. Allen M D, Zhang J. 2006. *Biochem Biophys Res Commun* 348: 716-21
54. Regot S, Hughey J J, Bajar B T, Carrasco S, Covert M W. 2014. *Cell* 157: 1724-34
55. Yi J J, Wang H, Vilela M, Danuser G, Hahn K M. 2014. *ACS Synth Biol* 3: 788-95
56. Melero-Fernandez de Mera R M, Li L L, Popinigis A, Cisek K, Tuittila M, et al. 2017. *Nat Commun* 8: 15017
57. Fushimi K, Ikeuchi M, Narikawa R. 2017. *Photochem Photobiol* 93: 903-6
58. Piatkevich K D, Subach F V, Verkhusha V V. 2013. *Nat Commun* 4: 2153
59. Otwinowski Z, Minor W. 1997. *Methods Enzymol* 276: 307-26
60. Vagin A, Teplyakov A. 1997. *Journal of Applied Crystallography* 30: 1022-5
61. Adams P D, Afonine P V, Bunkoczi G, Chen V B, Davis I W, et al. 2010. *Acta Crystallogr D Blot Crystallogr* 66: 213-21
62. Terwilliger T C, Grosse-Kunstleve R W, Afonine P V, Moriarty N W, Zwart P H, et al. 2008. *Acta Crystallogr D Biol Crystallogr* 64: 61-9
63. Emsley P, Lohkamp B, Scott W G, Cowtan K. 2010. *Acta Crystallogr D Biol Crystallogr* 66: 486-501
64. Murshudov G N, Skubak P, Lebedev A A, Pannu N S, Steiner R A, et al. 2011. *Acta Crystallogr D Biol Crystallogr* 67: 355-67
65. Laskowski R A, Macarthur M W, Moss D S, Thornton J M. 1993. *Journal of Applied Crystallography* 26: 283-91
66. Hussein H A, Borrel A, Geneix C, Petitjean M, Regad L, Camproux A C. 2015. *Nucleic Acids Res* 43: W436-42
67. Longo P A, Kavran J M, Kim M S, Leahy D J. 2013. *Methods Enzymol* 529: 227-40

SEQUENCES miRFP670nano protein sequence (SEQ ID NO: 1)

```
MANLDKMLNTTVTEVRQFLQVDRVCVFQFEEDYSGVVVVEAVDDRWISILKTQVRDR
YFMETRGEEYSHGRYQAIADIYTANLTECYRDLLTQFQVRAILAVPILQGKKLWGLLVA
HQLAAPRQWQTWEIDFLKQQAVVVGIAIQQS
``` miRFP670nano DNA sequence (SEQ ID NO: 10)

```
atggcaaacctggacaagatgctgaataccacagtaacagaggtgcggcagttcctgcaggtggacagagtgtgcgtgttccagtttgagg
aggattatagcggagtggtggtggtggaggccgtggacgataggtggatcctccatcctgaagacccaggtgcgggatagatacttcatgg
agacaaggggcgaggagtattctcacggccgctaccaggccatcgccgacatctacaccgcaaacctgacagagtgctacagggatctg
ctgacacagtttcaggtgagagcaatcctggccgtgccatcctgcagggcaagaagctgtggggcctgttggtggcacaccagctggcg
gcccctagacagtggcagacctgggagatcgactttctgaagcagcaggccgtggtggtgggcatcgccatccagcagagc
``` miRFP670nano3 protein sequence (SEQ ID NO: 2)

```
MANLDKMLNTTVTEVRKFLQADRVCVFKFEEDYSGTVSHEAVDDRWISILKTQVQDRY
FMETRGEEYVHGRYQAIADIYTANLVECYRDLLIEFQVRAILAVPILQGKKLWGLLVAH
QLAGPREWQTWEIDFLKQQAVVMGIAIQQS
``` miRFP670nano3 DNA sequence (SEQ ID NO: 11)

```
atggcaaacctggacaagatgctgaacaccaccgtgaccgaggtgcgcaagttcctgcaagcggacagagtgtgcgtgttcaagttcgag
gaagattactccggcaccgtctcgcacgaagccgtggacgacagatggattagcatcctgaagacccaggtgcaggacagatacttcatg
gaaaccagaggcgaggaatacgtccacggcagataccaggccatcgccgacatctacacagccaatctggtcgagtgctacagagacct
gctgatcgagtttcaggtgcgggccattctggctgtccccatcctgcaaggcaagaagctgtggggcctgctggtggcccaccaactggcc
ggccctcgggagtggcagacctgggaaatcgacttcctgaaacagcaagccgtggtgatgggcatcgccatccagcagagc
``` miRFP704nano protein sequence (SEQ ID NO: 3)

```
MANLDKMLNTIVTEVRQFLQVDRVCVFQFEEDYSGSVVVEAVDDRWNSILKTQVRDC
YFMETRGEEYLHGRYQAIADIYQANLLESYRDLLGQFQVRAILAVPIIKGKKLWGLLVA
HQLAAPRSWQTWEIEFLKQQAVVMGIAIQQS
``` miRFP704nano DNA sequence (SEQ ID NO: 12)

atggcaaacctggacaagatgctgaacaccatcgtgaccgaggtgcgccagttcctgcaagtggacagagtgtgcgtgttccagttcgag
gaagattactccggcagcgtcgtcgtggaagccgtggacgacagatggaacagcatcctgaagacccaggtgcgggactgctacttcatg
gaaaccagaggtgaggaatacttgcacggcagataccaggccatcgccgacatctaccaggccaatctgctggagagctacagagacct
gctgggccagtttcaggtgcgggccattctggctgtccccatcatcaagggcaagaagctgtggggcctgctggtggccaccaactggct
gcccctcggagctggcagacctgggaaatcgagttcctgaaacagcaagccgtggtgatgggcatcgccatccagcagagc miRFP718nano protein sequence (SEQ ID NO: 4)

MANLDKMLNTIVTEVRQFLQVDRLCVFKFEEDYSGNIIYEAVDDGWLSILKTHVRDCYF
METRGEEYLHGRYQAIADIHQANLAESYRDFLTQYQVRAIVAVPILKGKKLWGLFSAH
QLAAPRSWQAWEIEFLKQQAVVMGIAIQQS miRFP718nano DNA sequence (SEQ ID NO: 13)

atggcaaacctggacaagatgctgaacaccatcgtgaccgaggtgcgccagttcctgcaagtggacagactctgcgtgttcaagttcgagg
aagattactccggcaacatcatctacgaagccgtggacgacggatggttgagcatcctgaagacccacgtgcgggactgctacttcatgga
aaccagaggcgaggaatacctgcacggcagataccaggccatcgccgacatccaccaggccaatctggcggagagctatagagacttc
ctgacccagtaccaggtgcgggccattgtggctgtccccatcctgaagggcaagaagctgtggggcttgttcagcgcccaccaactggcc
gcccctcggagctggcaggcctgggaaatcgagttcctgaaacagcaagccgtggtgatgggcatcgccatccagcagagc circular permutated miRFP670nano protein sequence (SEQ ID NO: 5)

MASGKKLWGLLVAHQLAAPRQWQTWEIDFLKQQAVVVGIAIQQSGGGGSANLDKML
NTTVTEVRQFLQVDRVCVFQFEEDYSGVVVVEAVDDRWISILKTQVRDRYFMETRGEE
YSHGRYQAIADIYTANLTECYRDLLTQFQVRAILAVPILQGS circular permutated miRFP670nano DNA sequence (SEQ ID NO: 14)

atggcctccggcaagaagctgtggggcctgttggtggcacaccagctggggcccctagacagtggcagacctgggagatcgactttctg
aagcagcaggccgtggtggtgggcatcgccatccagcagagcggcggcggcggcagcgcaaacctggacaagatgctgaataccaca
gtaacagaggtgcggcagttcctgcaggtggacagagtgtgcgtgttccagtttgaggaggattatagcggagtggtggtggtggaggcc
gtggacgataggtggatctccatcctgaagacccaggtgcgggatagatacttcatggagacaagggggcgaggagtattctcacggccgc
taccaggccatcgccgacatctacaccgcaaacctgacagagtgctacagggatctgctgacacagtttcaggtgagagcaatcctggcc
gtgcccatcctgcagggcagc circular permutated miRFP670nano3 protein sequence (SEQ ID NO: 6)

MASGKKLWGLLVAHQLAGPREWQTWEIDFLKQQAVVMGIAIQQSGGGGSANLDKML
NTTVTEVRKFLQADRVCVFKFEEDYSGTVSHEAVDDRWISILKTQVQDRYFMETRGEE
YVHGRYQAIADIYTANL VECYRDLLIEFQVRAILAVPILQGS circular permutated miRFP670nano3 DNA sequence (SEQ ID NO: 15)

atggcctccggcaagaagctgtggggcctgctggtggcccaccaactggccggccctcgggagtggcagacctgggagaatcgacttcct
gaaacagcaagccgtggtgatgggcatcgccatccagcagagcggcggcggcggcagcgcaaacctggacaagatgctgaacaccac
cgtgaccgaggtgcgcaagttcctgcaagcggacagagtgtgcgtgttcaagttcgaggaagattactccggcaccgtctcgcacgaagc
cgtggacgacagatggattagcatcctgaagacccaggtgcaggacagatacttcatggaaaccagaggcgaggaatacgtccacggca
gataccaggccatcgccgacatctacacagccaatctggtcgagtgctacagagacctgctgatcgagtttcaggtgcgggccattctggct
gtccccatcctgcaaggcagc circular permutated miRFP704nano protein sequence (SEQ ID NO: 7)

MASGKKLWGLLVAHQLAAPRSWQTWEIEFLKQQAVVMGIAIQQSGGGGSANLDKMLN
TIVTEVRQFLQVDRVCVFQFEEDYSGSVVVEAVDDRWNSILKTQVRDCYFMETRGEEY
LHGRYQAIADIYQANLLESYRDLLGQFQVRAILAVPIIKGS circular permutated miRFP704nano DNA sequence (SEQ ID NO: 16)

atggcctccggcaagaagctgtggggcctgctggtggcccaccaactggctgcccctcggagctggcagacctgggaaatcgagttcct
gaaacagcaagccgtggtgatgggcatcgccatcagcagagcggcggcggcggcagcgcaaacctggacaagatgctgaacaccat
cgtgaccgaggtgcgccagttcctgcaagtggacagagtgtgcgtgttccagttcgaggaagattactccggcagcgtcgtcgtggaagc
cgtggacgacagatggaacagcatcctgaagacccaggtgcgggactgctacttcatggaaaccagaggtgaggaatacttgcacggca
gataccaggccatcgccgacatctaccaggccaatctgctggagagctacagagacctgctgggccagtttcaggtgcgggccattctgg
ctgtccccatcatcaagggcagc circular permutated miRFP718nano protein sequence (SEQ ID NO: 8)

MASGKKLWGLFSAHQLAAPRSWQAWEIEFLKQQAVVMGIAIQQSGGGGSMANLDKM
LNTIVTEVRQFLQVDRLCVFKFEEDYSGNIIYEAVDDGWLSILKTHVRDCYFMETRGEE
YLHGRYQAIADIHQANLAESYRDFLTQYQVRAIVAVPILKGS circular permutated miRFP718nano DNA sequence (SEQ ID NO: 17)

atggcctccggcaagaagctgtggggcttgttcagcgcccaccaactggccgcccctcggagctggcaggcctgggaaatcgagttcctg
aaacagcaagccgtggtgatgggcatcgccatccagcagagcggcggcggcggcagcatggcaaacctggacaagatgctgaacacc
atcgtgaccgaggtgcgccagttcctgcaagtggacagactctgcgtgttcaagttcgaggaagattactccggcaacatcatctacgaagc

```
NpR3784 GAF domain protein sequence                                        (SEQ ID NO: 9)

NLDKVLNTTVTEVRQFLQVDRVFMYQFEPDYSGVVVVESVDDRWIAILNTQVQDTYFM
ETRGEEYSHGRIQAIADIYTAGLTECHRDLLTQFQVRANLAVPILQGKKLWGLLVANQC
AAPRQWQTWEIDFLKQLAVQVGIAIQQS

NpR3784 GAF domain DNA sequence                                            (SEQ ID NO: 18)

aatttggacaaggttctcaacactaccgttactgaagtccgtcaattcctgcaagta-
gatcgagtgttcatgtatcagtttgaaccagactacag
tggggtggtggtggtagagtctgttgatgatcgttggattgctatcctgaatacc-
caagttcaagacacttatttcatggaaactcgcggcgag
gagtacagtcatgggcgcatccaagctattgcagatatttatacagcaggtctgact-
gaatgccatcgcgatttacttactcagtttcaagtcag
ggcaaacttggcggttccaattttgcaaggaaaaaaattgtggggattattagttgctaaccagtgtgcagcaccccgccagtggcagacgt
gggaaatcgatttctcaaacaattggcagtacaggtgggcattgccatccagcaatct
```

---

What is claimed is:

1. An isolated fluorescent protein comprising an amino acid sequence with at least 95% sequence identity to the amino acid sequence of SEQ ID NO:2.

2. The isolated fluorescent protein according to claim 1, wherein the protein comprises the amino acid sequence of SEQ ID NO: 2.

3. The isolated fluorescent protein according to claim 1, wherein the protein comprises at least one amino acid residue selected from the group consisting of M7, I11, K17, A21, L24, C25, V26, F27, K28, E31, T36, S36, N36, I37, I38, S38, Y39, H39, A41, G45, L47, N47, S48, K51, H53, R55, C57, R57, V68, L68, Y72, H79, Q80, N82, A84, L84, V84, S86, Y87, F90, G92, I92, E93, Y94, I99, V100, I105, K106, F114, S115, H117, L119, G121, S124, E124, E131, Q136, V139, and M140, and wherein the amino acid positions correspond to amino acid residue number positions in SEQ ID NO:2.

4. The isolated fluorescent protein according to claim 3, wherein the protein comprises at least one amino acid residue selected from the group consisting of C25, C57, R57, A84, L84, V84, Y87, F90, G92, F114, S115, H117, and M140, and wherein the amino acid positions correspond to amino acid residue number positions in SEQ ID NO:2.

* * * * *